United States Patent
Kassab et al.

(10) Patent No.: US 10,363,354 B2
(45) Date of Patent: Jul. 30, 2019

(54) UNITARY BODY SYSTEMS AND DEVICES AND METHODS TO USE THE SAME FOR RETROPERFUSION

(71) Applicants: CVDevices, LLC, San Diego, CA (US); Hyo Won Choi, San Diego, CA (US)

(72) Inventors: Ghassan S. Kassab, La Jolla, CA (US); Hyo Won Choi, San Diego, CA (US)

(73) Assignee: CVDevices, LLC, San Diego, CA (US)

( * ) Notice: Subject to any disclaimer, the term of this patent is extended or adjusted under 35 U.S.C. 154(b) by 575 days.

(21) Appl. No.: 14/908,597

(22) PCT Filed: Jul. 31, 2014

(86) PCT No.: PCT/US2014/049270
§ 371 (c)(1),
(2) Date: Jan. 29, 2016

(87) PCT Pub. No.: WO2015/017714
PCT Pub. Date: Feb. 5, 2015

(65) Prior Publication Data
US 2016/0166754 A1    Jun. 16, 2016

Related U.S. Application Data

(60) Provisional application No. 61/917,018, filed on Dec. 17, 2013, provisional application No. 61/866,280, (Continued)

(51) Int. Cl.
*A61M 1/36*    (2006.01)
*A61M 25/09*    (2006.01)
(Continued)

(52) U.S. Cl.
CPC ........ *A61M 1/3613* (2014.02); *A61M 1/3655* (2013.01); *A61M 25/09* (2013.01);
(Continued)

(58) Field of Classification Search
CPC ... A61M 1/3613; A61M 1/3655; A61M 39/24
See application file for complete search history.

(56) References Cited

U.S. PATENT DOCUMENTS 4,318,401 A    3/1982    Zimmerman
4,957,110 A    9/1990    Vogel et al.
(Continued)

FOREIGN PATENT DOCUMENTS

| JP | U-H06-021648 | 3/1994 |
|---|---|---|
| WO | WO 99/60941 | 2/1999 |
| WO | WO 08/144382 | 11/2008 |

OTHER PUBLICATIONS

PCT/US2008/037363, International Search Report (ISR), dated Feb. 13, 2009.
(Continued)

*Primary Examiner* — Leslie R Deak
(74) *Attorney, Agent, or Firm* — Reichel Stohry LLP; Mark C. Reichel; Natalie J. Dean

(57) ABSTRACT

Unitary body systems and devices and methods to use the same for retroperfusion. In an exemplary device embodiment of the present disclosure, the device comprises a unitary body having a wall and a lumen defined therethrough, a first portion terminating at a first end and configured for at least partial placement within a mammalian artery, a first one-way valve positioned at or near an end of the first portion opposite the first end, a second portion terminating at a second end and configured for at least partial placement within a mammalian vein, and a second one-way valve positioned at or near an end of the second portion opposite the second end.

20 Claims, 29 Drawing Sheets

Related U.S. Application Data filed on Aug. 15, 2013, provisional application No. 61/860,395, filed on Jul. 31, 2013.

(51) Int. Cl.
| | | |
|---|---|---|
| *A61M 29/02* | (2006.01) | |
| *A61M 39/24* | (2006.01) | |
| *A61F 2/06* | (2013.01) | |
| *A61F 2/24* | (2006.01) | |

(52) U.S. Cl.
CPC ............ *A61M 29/02* (2013.01); *A61M 39/24* (2013.01); *A61F 2/06* (2013.01); *A61F 2/2475* (2013.01)

(56) References Cited

U.S. PATENT DOCUMENTS

| | | | |
|---|---|---|---|
| 5,259,587 A | | 11/1993 | D'Alessio et al. |
| 5,273,534 A | | 12/1993 | Knoepfler |
| 5,494,822 A | | 2/1996 | Sadri |
| 5,511,553 A | | 4/1996 | Segalowitz |
| 5,655,548 A | * | 8/1997 | Nelson ........... A61B 17/320016 128/898 |
| 5,755,682 A | * | 5/1998 | Knudson ................ A61B 17/11 604/8 |
| 6,053,901 A | | 4/2000 | Finch et al. |
| 6,059,745 A | * | 5/2000 | Gelbfish ............. A61M 1/3621 604/6.09 |
| 6,110,139 A | | 8/2000 | Loubser |
| 6,186,972 B1 | | 2/2001 | Nelson et al. |
| 6,241,699 B1 | | 6/2001 | Suresh et al. |
| 6,726,651 B1 | | 4/2004 | Robinson et al. |
| 7,004,925 B2 | | 2/2006 | Navia et al. |
| 7,004,926 B2 | | 2/2006 | Navia et al. |
| 7,112,211 B2 | | 9/2006 | Gifford et al. |
| 7,473,237 B2 | | 1/2009 | Navia et al. |
| 7,819,856 B2 | | 10/2010 | Bates |
| 8,313,452 B2 | | 11/2012 | Franco Nardo et al. |
| 8,784,355 B2 | | 7/2014 | Criado et al. |
| 8,945,039 B2 | | 2/2015 | Kassab |
| 8,979,786 B2 | | 3/2015 | Kassab |
| 9,108,000 B2 | | 8/2015 | Kassab et al. |
| 2001/0007058 A1 | | 7/2001 | Jonsson et al. |
| 2001/0021817 A1 | | 9/2001 | Brugger et al. |
| 2003/0125798 A1 | | 7/2003 | Martin |
| 2003/0181843 A1 | | 9/2003 | Bibber et al. |
| 2004/0249334 A1 | | 12/2004 | Cull |
| 2004/0249335 A1 | | 12/2004 | Faul et al. |
| 2005/0059931 A1 | | 3/2005 | Garrison et al. |
| 2005/0154250 A1 | | 7/2005 | Aboul-Hosn et al. |
| 2005/0267323 A1 | | 12/2005 | Dorros et al. |
| 2006/0184088 A1 | | 8/2006 | Van Bibber et al. |
| 2006/0224232 A1 | | 10/2006 | Chobotov |
| 2007/0010781 A1 | | 1/2007 | Vijay |
| 2008/0109069 A1 | | 5/2008 | Coleman et al. |
| 2008/0234658 A1 | | 9/2008 | Kassab et al. |
| 2010/0022940 A1 | | 1/2010 | Thompson |
| 2010/0056978 A1 | | 3/2010 | Machan et al. |
| 2011/0196282 A1 | | 8/2011 | Kassab |
| 2014/0039538 A1 | | 2/2014 | Kassab et al. |
| 2014/0148751 A1 | | 5/2014 | Kassab |

OTHER PUBLICATIONS

PCT/US2008/037363, Written Opinion of the International Searching Authority, dated Feb. 13, 2009.
PCT/US2014/049270, International Search Report (ISR), dated Feb. 10, 2015.
PCT/US2014/049270, Written Opinion of the International Searching Authority, dated Feb. 10, 2015.
Extended European Search Report, European Patent Application Serial No. 14831373.7, dated Feb. 24, 2017.

* cited by examiner

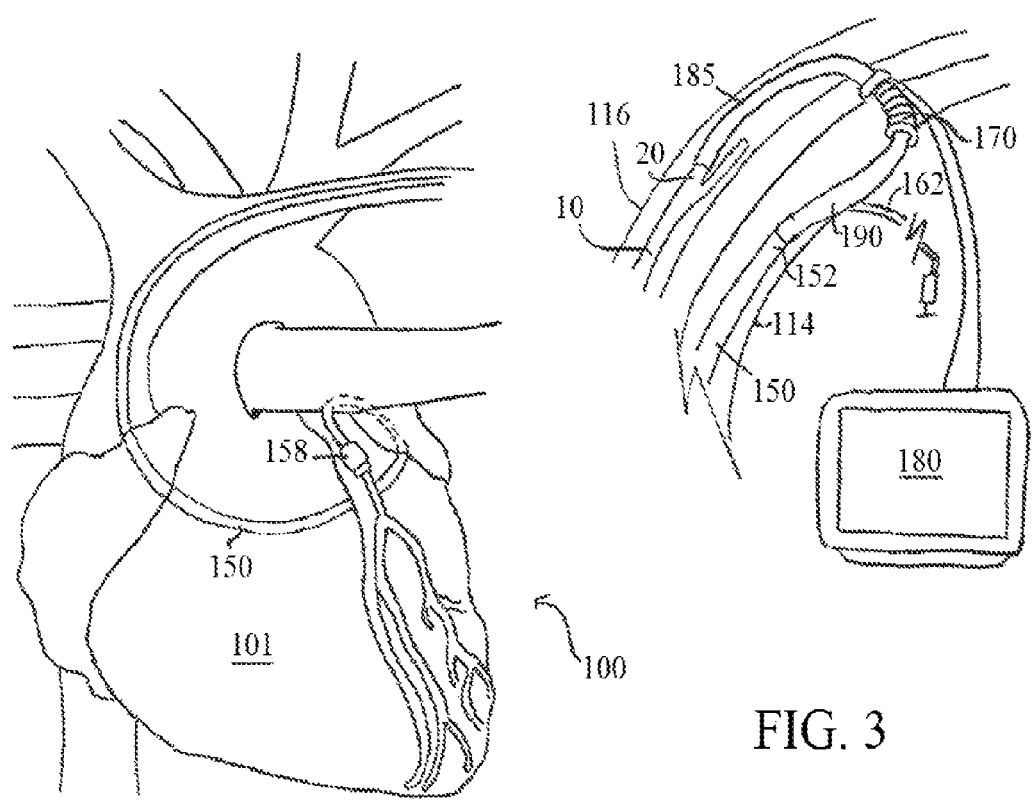
FIG. 3
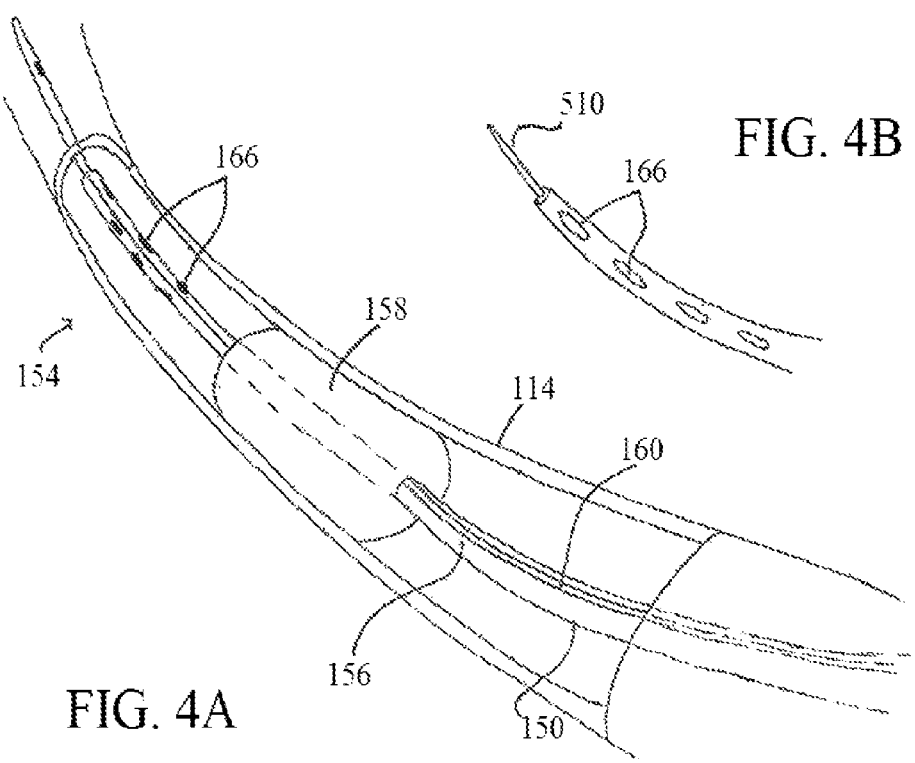
FIG. 4B
FIG. 4A

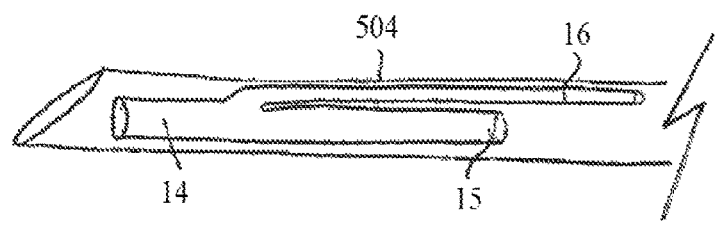
FIG. 8A
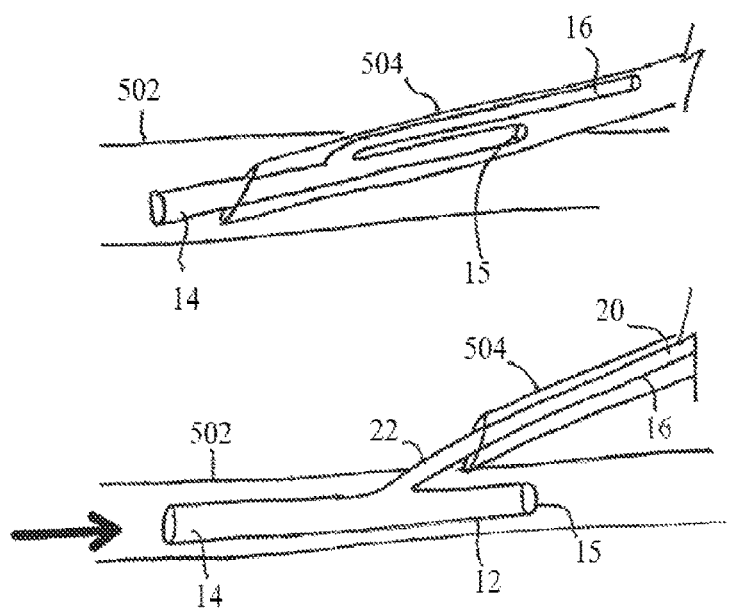
FIG. 8B
FIG. 8C
FIG. 8D
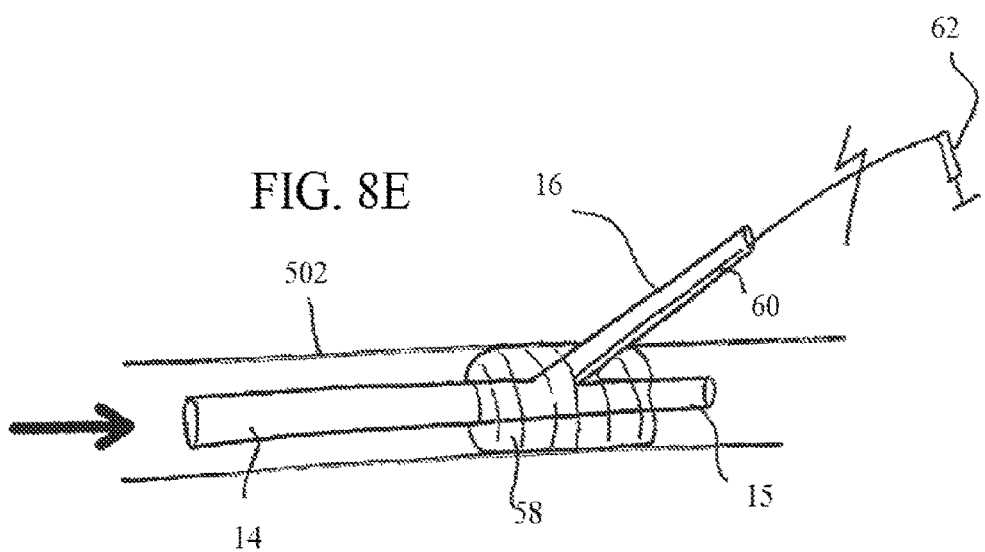
FIG. 8E

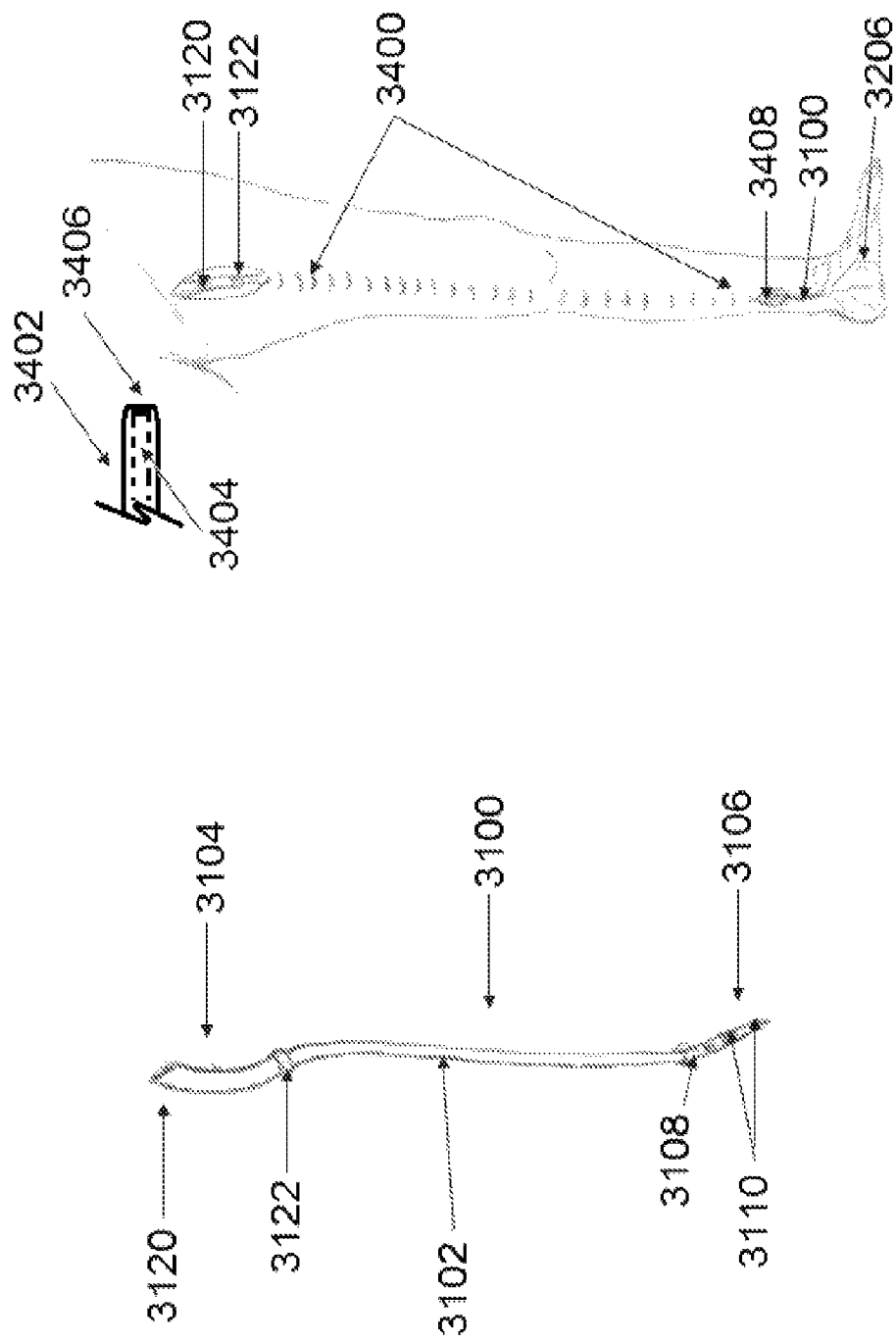

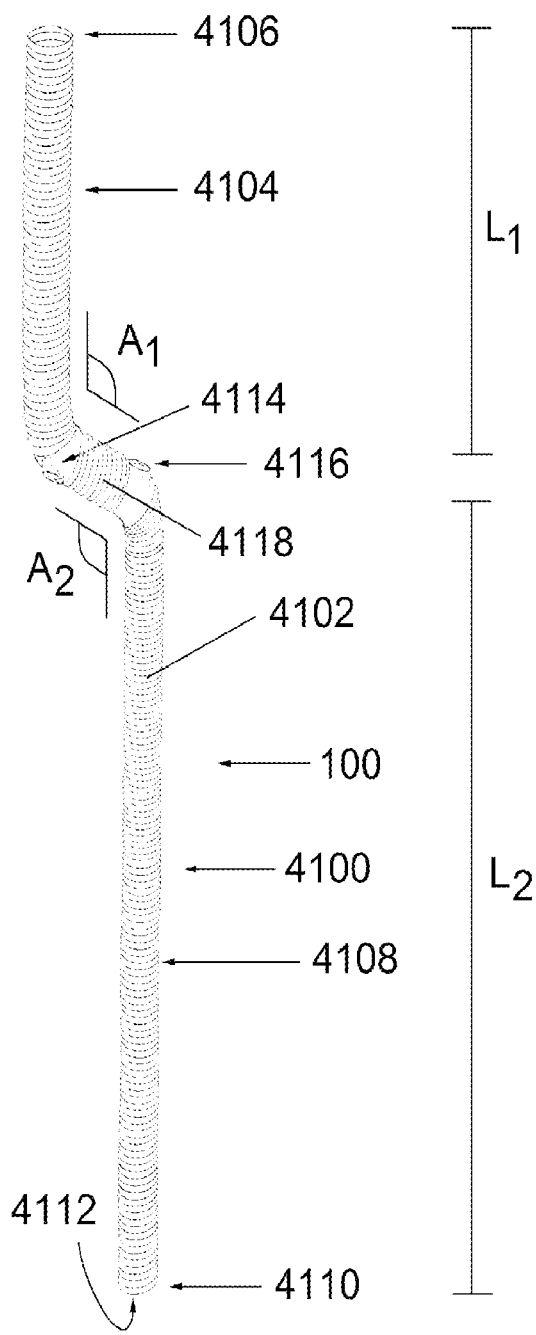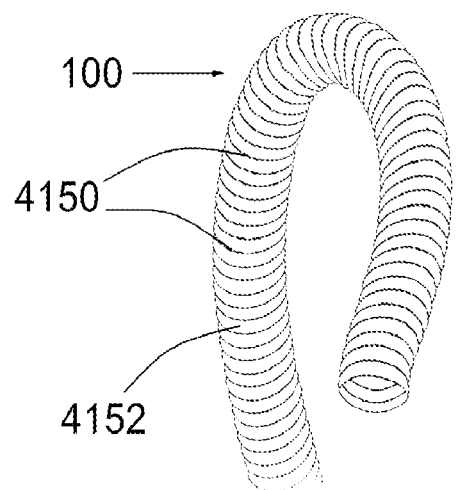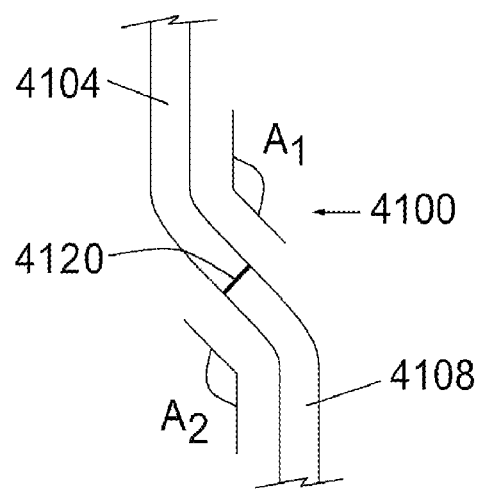
FIG. 27A
FIG. 27B
FIG. 27C

UNITARY BODY SYSTEMS AND DEVICES AND METHODS TO USE THE SAME FOR RETROPERFUSION

PRIORITY

The present application is related to, claims the priority benefit of, and is U.S. 35 U.S.C. 371 national stage patent application of, International Patent Application Serial No. PCT/US14/49270, filed Jul. 31, 2014, which is related to, and claims the priority benefit of, U.S. Provisional Patent Application Ser. No. 61/860,395, filed Jul. 31, 2013, U.S. Provisional Patent Application Ser. No. 61/866,280, filed Aug. 15, 2013, and U.S. Provisional Patent Application Ser. No. 61/917,018, filed Dec. 17, 2013. The contents of each of these applications are hereby incorporated by reference in their entirety into this disclosure.

INCORPORATION BY REFERENCE

The contents of the following patent applications are hereby incorporated by reference in their entirety into this disclosure: (a) U.S. patent application Ser. No. 13/705,101, filed Dec. 4, 2012, (b) U.S. patent application Ser. No. 13/965,548, filed Aug. 13, 2013, and (c) U.S. patent application Ser. No. 14/093,300, filed Nov. 29, 2013.

BACKGROUND

Peripheral arterial disease involves inadequate blood supply to the peripheral limbs due to arterial damage, defect, or blockage. In view of the same, devices, systems, and methods of using the same to facilitate adequate blood supply to the peripheral limbs would be well appreciated in the marketplace.

BRIEF SUMMARY

The present disclosure includes disclosure of various perfusion and/or retroperfusion devices and systems and methods of using the same, configured for use in connection with various coronary, peripheral, and other retroperfusion methods/procedures and/or to treat various conditions of ischemia and/or to facilitate/promote local venous arterialization.

In at least one embodiment of a perfusion device of the present disclosure, the perfusion device comprises a unitary body having a wall and a lumen defined therethrough, a first portion terminating at a first end and configured for at least partial placement within a mammalian artery, and a second portion terminating at a second end and configured for at least partial placement within a mammalian vein. In another embodiment, the first portion is relatively shorter than the second portion. In yet another embodiment, the first portion has a first length, wherein the second portion has a second length, and wherein the first length is less than the second length. In an additional embodiment, the device further comprises a first one-way valve positioned at or near an end of the first portion opposite the first end. In yet an additional embodiment, the device further comprises a second one-way valve positioned at or near an end of the second portion opposite the second end.

In at least one embodiment of a perfusion device of the present disclosure, the device further comprises an optional segment between the first one-way valve and the second one-way valve. In an additional embodiment, the first one-way valve and the second one-way valve are each sized and shaped to be immediately adjacent to one another. In yet an additional embodiment, the one-way valve is sized and shaped to receive at least part of a first guidewire therethrough. In another embodiment, the second one-way valve is sized and shaped to receive at least part of a second guidewire therethrough.

In at least one embodiment of a perfusion device of the present disclosure, and when in use, at least part of the first portion could be positioned within a subclavian artery or axiallary artery, and wherein at least part of the second portion could be positioned within a subclavian vein or an axillary vein for use and/or treatment at or near the heart. In another embodiment, in use at least part of the first portion could be positioned within an iliac artery, and wherein at least part of the second portion could be positioned within a saphenous vein or a femoral vein. In yet another embodiment, the entire body is flexible or one or more portions of the body is/are flexible. In an additional embodiment, the body is able to deform easily without collapsing so that the lumen remains open to allow blood to flow from the first end, through the body, and out of the second end when in use.

In at least one embodiment of a perfusion device of the present disclosure, the body comprises a coil-reinforced wall having one or more coils. In an additional embodiment, the one or more coils are used in connection with an impermeable coating. In yet an additional embodiment, the device further comprises a balloon positioned within or coupled to the second portion. In another embodiment, the device further comprises a balloon tube having a balloon port, the balloon tube coupled to the balloon. In at least one embodiment of a perfusion device of the present disclosure, introduction of a gas and/or a liquid into the balloon port can be used to inflate the balloon, and removal of the gas and/or the liquid via the balloon port can be used to deflate the balloon. In an additional embodiment, the balloon is used to ensure retrograde flow of blood. In yet an additional embodiment, at least a portion of the device is sized and shaped to fit within a splittable introducer sheath.

In at least one embodiment of a perfusion device of the present disclosure, the device further comprises a flarable tip defined at or coupled to the second end of the device. In another embodiment, the flarable tip is configured to shift from a first configuration to a second configuration and back to the first configuration. In yet another embodiment, the first configuration is generally tapered or unflared, and wherein the second configuration is generally flared. In an additional embodiment, the first configuration is not expanded, and wherein the second configuration is expanded. In at least one embodiment of a perfusion device of the present disclosure, the first configuration exists under typical venous blood pressure, and wherein the second configuration exists due to a relatively higher arterial blood pressure. In an additional embodiment, the flarable tip is generally configured so that the second end distends to a luminal perimeter of a portion of a vein having the second end positioned therein so that blood flow therethrough is retrograde. In yet an additional embodiment, the flarable tip comprises a membrane reinforced by a plurality of struts. In another embodiment, the membrane comprises a material selected from the group consisting of polytetrafluoroethylene, mammalian tissue, and/or one or more other biologically-compatible thin or relatively thin materials. In yet another embodiment, the struts comprise a material selected from the group consisting of nitinol, stainless steel, and/or one or more other biologically-compatible rigid compositions.

In at least one embodiment of a perfusion device of the present disclosure, the second portion comprises a first tapered portion. In another embodiment, the first tapered portion comprises part of the second portion. In yet another embodiment, the first tapered portion comprises all or substantially all of second portion. In an additional embodiment, the second portion is sized and shaped to conform to dimensions of the mammalian vein. In yet an additional embodiment, the device is configured so that the second portion is sized and shaped to facilitate implantation within the mammalian vein. In at least one embodiment of a perfusion device of the present disclosure, the device is configured so that the second portion is sized and shaped to reduce a risk of rupture of the mammalian vein. In an additional embodiment, the tapered portion tapers distally from a first diameter to a second diameter, wherein the first diameter is greater than the second diameter. In yet an additional embodiment, the second portion comprises a second tapered portion. In another embodiment, the second portion comprises one or more additional tapered portions. In yet another embodiment, the first tapered portion is the only tapered portion.

In at least one embodiment of a perfusion device of the present disclosure, a degree, number, and length of tapered portions can be selected to regulate the degree of pressure drop along the device in order to reduce the transmission of arterial pressure to the venous system and to generally avoid over-pressurization of the venous system. In another embodiment, a blood pressure is decreased during blood flow through the device. In yet another embodiment, the decrease in blood pressure is facilitated at the first tapered portion. In at least one embodiment of a perfusion device of the present disclosure, when the first portion is immediately adjacent to the second portion, the first portion meets the second portion at a central junction. In another embodiment, part of the first portion adjacent to the central junction is flexible. In yet another embodiment, part of the second portion adjacent to the central junction is flexible. In an additional embodiment, the first portion is configured to bend at a first amount, the first amount having a range of above 0° to 180°. In yet an additional embodiment, the second portion is configured to bend at a second amount, the second amount having a range of above 0° to 180°. In at least one embodiment of a perfusion device of the present disclosure, the device is configured so that a first angle ranging from above 0° to 180° can be formed within the first portion and/or a second angle ranging from above 0° to 180° can be formed within the second portion. In an additional embodiment, when the device comprises a segment between the first one-way valve and the second one way-valve, the device is configured so that a first angle ranging from above 0° to 180° can be formed relative to the first portion and the segment and/or a second angle ranging from above 0° to 180° can be formed relative to the second portion and the segment. In yet an additional embodiment, the bend at the first amount corresponds to the first angle in various embodiments and wherein the bend at the second amount corresponds to the second angle in various embodiments.

In at least one embodiment of a perfusion device of the present disclosure, a pressure drop along the device can vary depending upon the bend at the first amount, the first angle, the bend at the second amount, and/or the second angle. In another embodiment, the pressure drop can be regulated up to at least 32% due to an extent of the first amount, the first angle, the bend at the second amount, and/or the second angle. In yet another embodiment, the pressure drop is a function of a device length, a device diameter, a flow friction factor, and a relative flow condition between two vessels which are connected by the device. In at least one embodiment of a retroperfusion system of the present disclosure, the system comprises an exemplary retroperfusion device of the present disclosure, and at least one other item, such as, for example, one or more of a first guide wire, a second guide wire, a splittable introducer sheath, and/or a data wire.

The various device and systems referenced herein may be configured for use in connection with various coronary, peripheral, and other retroperfusion methods/procedures and/or to treat various conditions of ischemia and/or to facilitate/promote local venous arterialization, depending on device and/or system configuration. In at least one embodiment of a method of the present disclosure, the method comprises, one or more of the steps of, in any order, (a) implanting an exemplary retroperfusion device of the present disclosure into a patient so that a first part of the device is in communication with an artery and that a second part of the device is in communication with a vein and so that blood can flow from the artery, through the device, and into the vein; (b) bending the device so that one or more desired angles and/or bends are present along at least part of the device, so to obtain a desired pressure drop through the device; (c) configuring one or more lengths and/or one or more diameters of the device and/or of parts of the device based upon use within the patient, a height of the patient, a blood pressure of the patient, and/or a flow of blood through the artery and/or the vein of the patient; and/or (d) selecting a suitable device from a plurality of available devices, the suitable device selected based upon the one or more lengths and/or the one or more diameters of the device and/or of parts of the device based upon use within the patient, the height of the patient, the blood pressure of the patient, and/or the flow of blood through the artery and/or the vein of the patient. In at least one method, the method comprises the steps of positioning a first portion of a perfusion device within an artery, wherein a first guidewire is positioned through part of the first portion of the device into the artery, and positioning a second portion of a perfusion device within an vein, wherein a second guidewire is positioned through part of the second portion of the device into the vein, and removing the first guidewire from the first part of the device and removing the second guidewire from the second part of the device. In another embodiment, the part of the first portion is the first one-way valve, and the part of the second portion is the second one-way valve. In various embodiments, blood can flow from the artery, through the perfusion device, and into the vein. In another method, the method further comprises the step of bending the perfusion device to form a desired angle within the device. In an exemplary method embodiment, the method comprises the step of positioning a device of the present disclosure within a mammalian patient so that the first portion is positioned within an artery and so that the second portion is positioned within a vein. In another embodiment, the positioning step is performed by positioning a first portion of a perfusion device within the artery, wherein a first guidewire is positioned through part of the first portion of the device into the artery, and positioning a second portion of a perfusion device within the vein, wherein a second guidewire is positioned through part of the second portion of the device into the vein. In another embodiment, the positioning step is further performed by advancing a first dilator over the first guidewire before positioning the first portion of the perfusion device into the artery and by advancing a second dilator over the second guidewire before positioning the second portion of the perfusion device into the vein.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 3 shows a side view of an autoretroperfusion system positioned to deliver retroperfusion therapy to a heart, according to at least one embodiment of the present disclosure;

FIGS. 4A and 4B show perspective views of the distal end of a venous catheter used in the autoretroperfusion system of FIG. 3, according to at least one embodiment of the present disclosure;

FIG. 8A shows a side view of the catheter of FIG. 1 in a collapsed position within an introducer, according to at least one embodiment of the present disclosure;

FIG. 8B, shows a side view of the catheter of FIG. 1 being introduced via an introducer into an arterial vessel, according to at least one embodiment of the present disclosure;

FIGS. 8C and 8D show side views of the introducer of FIG. 8A being removed from an arterial vessel, thereby deploying the projection cannula of the catheter of FIG. 1, according to at least one embodiment of the present disclosure;

FIG. 8E shows a side view of the catheter of FIG. 1 anchored within an arterial vessel through the use of an expandable balloon, according to at least one embodiment of the present disclosure;

FIG. 24A shows an intravenous arterialization catheter, according to an exemplary embodiment of the present disclosure;

FIG. 24B shows an embodiment of a catheter positioned subcutaneously and into a vein and connected to a graft in communication with an artery, according to an exemplary embodiment of the present disclosure;

FIG. 27A shows a retroperfusion device, according to an exemplary embodiment of the present disclosure;

FIG. 27B shows a portion of a retroperfusion device according to an exemplary embodiment of the present disclosure;

FIG. 27C shows part of a retroperfusion device, according to an exemplary embodiment of the present disclosure;

DETAILED DESCRIPTION

Figure 1:
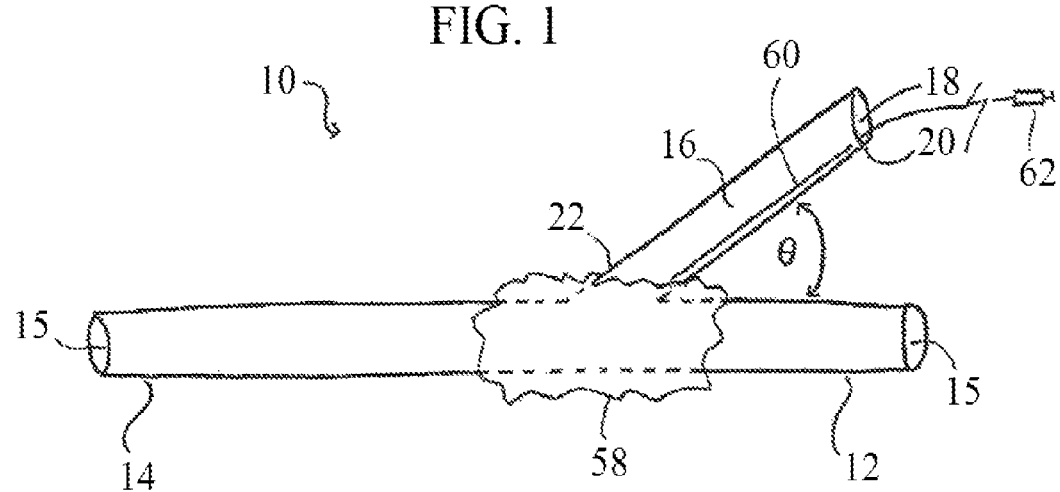
FIG. 1 shows a side view of a catheter for placement within an arterial vessel and that may be used to deliver retroperfusion therapy, according to at least one embodiment of the present disclosure.

The embodiments discussed herein include devices, systems, and methods useful for providing selective autoretroperfusion to the venous system. In addition, and with various embodiments of devices and systems of the present disclosure, said devices and/or systems can also be used to achieve a controlled arterialization of the venous system. For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The devices, systems and methods disclosed herein can be used to safely and selectively arterialize venous vessels in order to decrease the stress thereon and prevent rupture of the same. Accordingly, through the use of the devices, systems and methods disclosed herein, long-term autoretroperfusion of oxygenated blood through the coronary venous system can be achieved, thereby providing a continuous supply of oxygen-rich blood to an ischemic area of a tissue or organ. While the devices, systems and methods disclosed herein are described in connection with a heart, it will be understood that such devices, systems and methods are not limited in their application solely to the heart and the same may be used in connection with any ischemic tissue and/or organ in need of an oxygen-rich blood supply.

Selective auto-retroperfusion (SARP) can be indicated for both chronic and acute applications, and exemplary catheters 10 and/or systems 100 of the present disclosure (and as referenced in further detail herein) can be used in connection therewith. References to "acute" for SARP applications are used generally to indicate the amount of time that an exemplary catheter 10 and/or system 100 of the present disclosure may be in use on a given patient. In at least one embodiment, catheter 10 and/or system 100, or portions thereof, will be sterile and intended for disposal after a single use. In at least one embodiment of a system 100 useful in connection with an acute indication, use of system 100 could be limited to less than 24 hrs.

Now referring to FIG. 1, a side view of a catheter 10 is shown. The catheter 10 is configured to be placed within an arterial vessel and comprises a flexible, elongated tube having a proximal end 12, a distal end 14 and at least one lumen 15 extending between the proximal end 12 and the distal end 14. The dimensions of the catheter 10 may vary depending on the particulars of a specific patient or with respect to the artery to be cannulated. For example and without limitation, where the catheter 10 is used to in a system for autoretroperfusion of the coronary sinus, the catheter 10 may comprise a diameter of about 2.7 millimeters to about 4 millimeters (about 8 Fr to about 12 Fr). Furthermore, the at least one lumen 15 of the catheter 10 comprises a sufficient diameter such that blood can flow therethrough. In addition, the catheter 10 may be comprised of any appropriate material, including without limitation, polyurethane or silicone rubber. Furthermore, the catheter 10 may be coated with heparin or any other suitable anticoagulant such that the catheter 10 may be placed within a vessel for an extended period of time without inhibiting blood flow due to coagulation. The distal end 14 of the catheter 10 is configured to allow arterial blood to flow therethrough and into the at least one lumen 15 of the catheter 10. Similarly, the proximal end 12 of the catheter 10 is configured to allow blood within the at least one lumen 15 to flow out of the catheter 10. Accordingly, when the catheter 10 is positioned within an arterial vessel, the oxygenated blood is allowed to flow into the catheter 10 through the distal end 14 of the catheter 10, through the at least one lumen 15, and out of the catheter 10 through the proximal end 12 of the catheter 10. In this manner, placement of the catheter 10 within a vessel does not inhibit the flow of blood through the vessel or significantly affect the pressure of the blood flow within the vessel.

As shown in FIG. 1, the catheter 10 further comprises a projection cannula 16 that extends from the proximal end 12 of the catheter 10 and forms a Y-shaped configuration therewith. The projection cannula 16 comprises a flexible tube of material that is appropriate for insertion within a vessel and placement within an opening in a vessel wall. Furthermore, the projection cannula 16 comprises at least one lumen 18, a proximal end 20, and a distal end 22. The distal end 22 of the projection cannula 16 is coupled with the body of the catheter 10 and configured to allow the lumen 18 of the projection cannula 16 to communicate with at least one of the at least one lumens 15 of the catheter 10. Accordingly, when blood flows through the at least one lumen of the catheter 10, a portion of the blood flow enters the lumen 18 of the projection cannula 16 through the distal end 22 thereof and flows out through the proximal end 20 of the projection cannula 16. In this manner, the catheter 10 is capable of bifurcating the flow of blood through the vessel in which it is inserted and routing some of that blood flow out of the vessel and to another location. This bifurcation can be exploited to modify the pressure of the blood flowing through the projection cannula 16 and/or through the proximal end 12 of the catheter 10 by manipulating the dimensions of the projection cannula 16 and the body of the catheter 10. For example, and without limitation, if the diameter of the projection cannula 16 is less than the diameter of the at least one lumen 15 of the catheter 10, the majority of the blood will flow through the proximal end 12 of the catheter 10 and the pressure of the remaining blood that flows through the smaller projection cannula 16 will necessarily be reduced. Predictably, the smaller the diameter of the lumen 18 of the projection cannula 16, the greater the pressure drop that can be achieved in the blood flowing through the lumen 18 of the projection cannula 16. Accordingly, with respect to the catheter's 10 application to autoretroperfusion therapies, the projection cannula 16 can be used to re-route blood flow from an artery to a vein while simultaneously achieving the necessary pressure drop in the re-routed blood between the arterial system and unarterialized venous system. Moreover, the catheter 10 is capable of maintaining substantially normal blood flow through the artery in which it is housed as the arterial blood not re-routed through the projection cannula 16 is allowed to flow through the open proximal end 12 of the catheter 10 and back into the artery in the normal antegrade fashion.

Figure 2A:
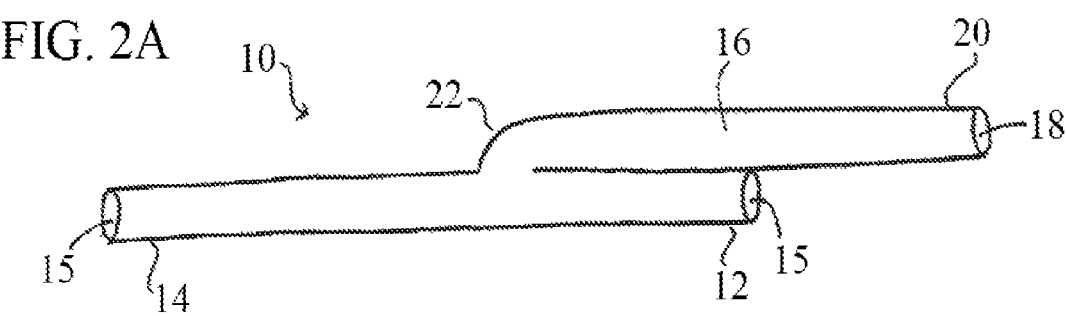
FIG. 2A shows a side view of the catheter of FIG. 1 in a collapsed position, according to at least one embodiment of the present disclosure.
Figure 2B:
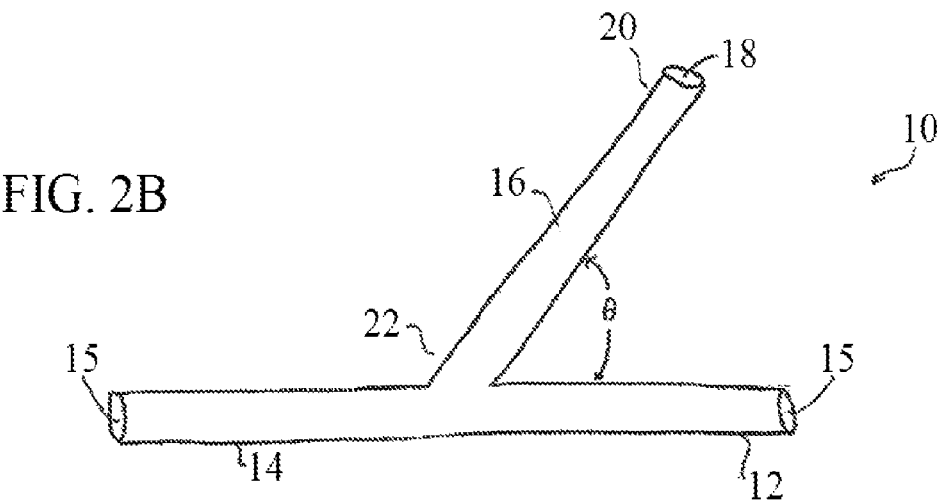
FIG. 2B shows a side view of the catheter of FIG. 1 in an extended position, according to at least one embodiment of the present disclosure.

Due to the configuration of the projection cannula 16 and the material of which it is comprised, the projection cannula 16 is capable of hingedly moving relative to the body of the catheter 10 between a collapsed position and an extended position. Now referring to FIGS. 2A and 2B, the projection cannula 16 is shown in the collapsed position (FIG. 2A) and in the extended position (FIG. 2B). When the projection cannula 16 is in the collapsed position, the projection cannula 16 is positioned substantially parallel with the body of the catheter 10. Alternatively, when the projection cannula 16 is in the extended position, the projection cannula 16 is positioned such that the projection cannula 16 forms an angle θ with the proximal end 12 of the catheter 10. The value of angle θ may be selected depending on the desired application of the catheter 10. For example, in at least one embodiment, the angle θ may comprise any value ranging between about 15° and about 90°. In another example, the angle θ may comprise about 45° when the projection cannula 16 is in the extended position. The projection cannula 16 is biased such that, when it is not subject to a downward force, the projection cannula 16 rests in the expanded position. Conversely, when a downward force is applied to the projection cannula 16 by way of an introducer or otherwise, the projection cannula 16 moves into and remains in the collapsed position until the downward force is removed. In this manner, the projection cannula 16 may be introduced into a vessel in the collapsed position through the use of an introducer or shaft and thereafter move into the expanded position when the catheter 10 is properly positioned within the vessel and the introducer or shaft is removed.

Optionally, as shown in FIG. 1, the catheter 10 may further comprise an expandable balloon 58 coupled with an intermediary portion of the external surface of the catheter 10 such that the expandable balloon 58 encases the catheter 10 and the distal end 22 of the projection cannula 18. The expandable balloon 58 may be any expandable balloon 58 that is appropriate for insertion within a vessel and may comprise any material suitable for this function, including without limitation, polyethylene, latex, polyestherurethane, polyurethane, sylastic, silicone rubber, or combinations thereof. In operation, the expandable balloon 58 can be used to anchor the catheter 10 in a desired position within a vessel wall and prevent leakage from the opening in the vessel wall through which the projection cannula 16 traverses. The expandable balloon 58 is capable of being controlled by a clinician such that it can inflate and/or deflate to the proper size. The sizing of the expandable balloon 58 will differ between patients and applications. The expandable balloon 58 may be in fluid communication with a balloon inflation port 62 through a secondary lumen 60 within the lumen 18 of the projection cannula 16. Alternatively, the expandable balloon 58 may be in fluid communication with the balloon inflation port 62 through a tube or other means that is positioned within the lumen 18 of the projection cannula 16 as shown in FIG. 1. The balloon port 62 may be positioned subcutaneously or otherwise such that a clinician can easily access the balloon port 62 when the catheter 10 is positioned within a vessel. In this manner the balloon port 62 can be accessed by a clinician, subcutaneously, percutaneously or otherwise, and used to inflate or deflate the expandable balloon 58 with no or minimal invasion to the patient.

Now referring to FIG. 3, an autoretroperfusion system 100 is shown positioned to allow arterial blood to irrigate the coronary sinus of a heart 101. With respect to the heart 101, the autoretroperfusion system 100 may be used for treatment of myocardial infarctions by injecting arterial blood into the coronary sinus in synchronism with the patient's heartbeat. Furthermore, the autoretroperfusion system 100 is capable of controlling the pressure of the arterial blood flow as it enters the venous vessel such that when the arterial blood flow is first introduced into the venous system, the pressure of the re-routed arterial blood flow is reduced to protect the thinner venous vessels. In this manner, the venous system is allowed to gradually arterialize. Further, after the selected venous vessel has sufficiently arterialized, the autoretroperfusion system 100 is capable of reducing or ceasing its influence on the pressure of the re-routed arterial blood flow such that the standard arterial blood flow pressure is thereafter allowed to flow into the arterialized venous vessel.

Autoretroperfusion system 100 comprises the catheter 10, a second catheter 150, and a connector 170. The catheter 10 is for placement within an arterial vessel and is configured as previously described in connection with FIGS. 1-2B. The second catheter 150 is configured for placement within the venous system. The connector 170 is configured to form an anastomosis between the catheter 10 and the second catheter 150 and further functions to monitor various data points on the blood flow flowing therethrough. In addition, in at least one embodiment, the connector 170 is capable of controlling the pressure of arterial blood flowing therethrough. The second catheter 150 is configured for placement within a venous vessel wall 114 and comprises a flexible tube having a proximal end 152, a distal end 154 and at least one lumen 156 extending between the proximal end 152 and the distal end 154. Both the proximal end 152 and the distal end 154 of the second catheter 150 are open and in communication with the at least one lumen 156 of the second catheter 150, thereby allowing blood to flow into the at least one lumen 156 through the proximal end 152 and out of the distal end 154 back into the venous vessel 114. The second catheter 150 may be any catheter known in the art that is capable of intravascular insertion and advancement through the venous system and may comprise any appropriate material, including without limitation, polyurethane or silicone rubber. In at least one embodiment, the second catheter 150 is configured to receive a guidewire 510 (see FIGS. 4A and 4B) through the at least one lumen 156 to facilitate the intravascular delivery of the distal end 154 of the second catheter 150 into the desired location of the venous vessel 114. Furthermore, similar to the catheter 10, the second catheter 150 may be coated with heparin or any other suitable anti-coagulant prior to insertion in order to facilitate the extended placement of the second catheter 150 within the venous vessel 114. Accordingly, the autoretroperfusion system 100 may be used to deliver chronic retroperfusion treatment to an ischemic area of a body.

FIGS. 4A and 4B show side views of the distal end 154 of the second catheter 150 positioned within the venous vessel wall 114. As shown in FIG. 4A, the distal end 154 of the second catheter 150 may further comprise an expandable balloon 158 coupled with the external surface of the second catheter 150. In operation, the expandable balloon 158 can be used to anchor the distal end 154 of the second catheter 150 in the desired location within the venous vessel wall 114. The expandable balloon 158 may be any expandable balloon that is appropriate for insertion within a vessel and can be formed of any material suitable for this function, including without limitation, polyethylene, latex, polyestherurethane, polyurethane, sylastic, silicone rubber, or combinations thereof.

The expandable balloon 158 is capable of being controlled by a clinician such that it can inflate and/or deflate to the proper size. The sizing of the expandable balloon 158 will differ between patients and applications and it is often important to determine the proper sizing of the expandable balloon 158 to ensure the distal end 154 of the second catheter 150 is securely anchored within the desired location of the vessel wall 114. The accurate size of the expandable balloon 158 can be determined through any technique known in the art, including without limitation, by measuring the compliance of the expandable balloon 158 ex vivo or in vivo. In addition, the distal end 154 of the second catheter 150 may further comprise a plurality of electrodes that are capable of accurately measuring the cross-sectional area of the vessel of interest as is known in the art. For example, the plurality of electrodes may comprise a combination of excitation and detection electrodes as described in detail in the currently pending U.S. patent application Ser. No. 11/891,981 entitled System and Method for Measuring Cross-Sectional Areas and Pressure Gradients in Luminal Organs, and filed on Aug. 14, 2007, which is hereby incorporated by reference in its entirety. In at least one embodiment, such electrodes may comprise impedance and conductance electrodes and may be used in connection with ports for the suction of fluid from the vessel and/or the infusion of fluid therein. The expandable balloon 158 may be in fluid communication with a secondary lumen 160 disposed within the at least one lumen 156 of the second catheter 150. In this example, the secondary lumen 160 is coupled with a balloon port 162 that extends from the proximal end 152 of the second catheter 150 (see FIG. 3). Accordingly, when the autoretroperfusion system 100 is positioned within a patient, the balloon port 162 can be easily accessed by a clinician, subcutaneously, percutaneously or otherwise, and used to inflate or deflate the expandable balloon 158 with no or minimal invasion to the patient.

As shown in FIGS. 4A and 4B, the distal end 154 of the second catheter 150 may further comprise at least one sensor 166 coupled therewith. In at least one embodiment, the at least one sensor 166 is disposed on the distal end 154 of the second catheter 150 distally of the expandable balloon 158; however, it will be understood that the at least one sensor 166 may be disposed in any location on the distal end 154 of the second catheter 150. The at least one sensor 166 may be used for monitoring purposes and, for example, may be capable of periodically or continuously monitoring the pressure of the blood flow flowing through the at least one lumen 156 of the first catheter 150 or the venous vessel 14 in which the second catheter 150 is inserted. Additionally, one of the at least one sensors 166 may be used to monitor the pH or the concentrations of carbon dioxide, lactate, or cardiac enzymes within the blood. Furthermore, the at least one sensor 166 is capable of wirelessly communicating the information it has gathered to a remote module through the use of telemetry technology, the internet, or other wireless means, such that the information can be easily accessed by a clinician on a real-time basis or otherwise.

Now referring back to FIG. 3, the autoretroperfusion system 100 further comprises a connector 170. The connector 170 comprises any connector or quick connector known in the medical arts that is capable of forming an anastomosis between an artery and a vein such that oxygenated blood from the arterial system can flow into the venous system. For example, the connector 170 may comprise an annular connector that is capable of coupling with the proximal end 20 of the projection cannula 16 of the catheter 10 and with the proximal end 152 of the second catheter 150 such that arterial blood can flow continuously from the at least one lumen 15 of the catheter 10 to the at least one lumen 156 of the second catheter 150. The connector 170 may be formed of any suitable material known in the art including, but not limited to, silicon rubber, poly(tetrafluoroethene), and/or polyurethane. The connector 170 of the autoretroperfusion system 100 may comprise a pressure/flow regulator unit that is capable of measuring the flow rate of the blood moving therethrough, the pressure of the blood moving therethrough, and/or other data regarding the blood flowing through the anastomosis. The connector 170 may also be capable of transmitting such gathered data to a remote module 180 through a lead placed intravascularly or, in the alternative, through telemetry or another wireless means. The remote module 180 may comprise any device capable of receiving the data collected by the connector 170 and displaying the same. For example, and without limitation, the remote module 180 may comprise any display device known in the art or a computer, a microprocessor, hand-held computing device or other processing means.

Additionally, the connector 170 may further comprise a means for regulating the blood flow through the anastomosis. One of the main challenges of successfully delivering retroperfusion therapies is that the arterial blood pressure must be reduced prior to being introduced into a vein due to the thinner and more fragile anatomy of venous walls. Indeed, subjecting a non-arterialized venous vessel to the high pressures of arterial blood flow typically results in rupture of the venous vessel. Accordingly, with retroperfusion therapies, it is critical to ensure that the pressure of the arterial blood flow is at least initially controlled such that the venous vessel can arterialize prior to being subjected to the unregulated pressure of the arterial blood flow. In at least one embodiment the connector 170 may comprise an external compression device to facilitate the control of the flow rate of the blood moving through the anastomosis. Alternatively, other means that are known in the art may be employed to regulate the blood flow and pressure of the blood flowing through the anastomosis formed by the connector 170. In at least one embodiment, the means for regulating the blood flow through the anastomosis formed by the connector 170 is capable of regulating the pressure and/or flow velocity of the blood flowing through the anastomosis. For example, the means for regulating blood flow can be adjusted to ensure that about a 50 mg Hg pressure drop occurs in the blood flow between the arterial vessel and the venous vessel.

The connector 170 is capable of not only transmitting data to the remote module 180, but also receiving commands from the remote module 180 and adjusting the means for regulating blood flow pursuant to such commands. Accordingly, when the autoretroperfusion system 100 is positioned within a patient for retroperfusion therapy, a clinician can use the remote module 180 to view the blood flow data collected by the connector 170 and non-invasively adjust the connector 170 to achieve the desired pressure and/or flow through the anastomosis. Such remote control of the connector 170 is particularly useful as a clinician may incrementally decrease the connector's 170 regulation of the blood flow without surgical intervention during the venous arterialization process and/or after the venous vessel arterializes. Further, where the remote module 180 comprises a computer or other processing means, the remote module 180 is also capable of being programmed to automatically analyze the data received from the connector 170 and, based on the results thereof, suggest how to adjust the means of regulating the blood flow of the connector 170 and/or automatically adjust the means of regulating the blood flow of the connector 170 to achieve the optimal result. For example, and without limitation, when the autoretroperfusion system 100 is implanted into a patient and the anastomosis is first performed, the remote module 180 can automatically adjust the means for regulating the blood flow of the connector 170 based on the initial blood flow data received by the remote module 180. In this manner, the desired pressure drop between the arterial system and the venous system is immediately achieved and the risk of venous rupture is significantly reduced.

Alternatively, where the connector 170 of the autoretroperfusion system 100 does not comprise a means for regulating blood flow, the gradual arterialization of the venous vessel can be achieved through other techniques known in the art. For example, in at least one embodiment, the autoretroperfusion system 100 further comprises a coil designed to at least partially occlude the vein of interest. In this manner, the pressure is allowed to build in front of the portion of the vein at least partially occluded by the coil and the vein gradually arterializes. In this at least one embodiment, the coil may comprise a metallic memory coil (made of nitinol, stainless steel or other acceptable materials that are radioopaque) and is covered with polytetrafluorethylene, polyethylene terephthalate, polyurethane or any other protective covering available in the medical arts. Additionally, gradual arterialization can be performed by the second catheter 150. In this embodiment of autoretroperfusion system 100, the at least one lumen 156 of the second catheter 150 is designed to provide an optimal stenosis geometry to facilitate the desired pressure drop as the arterial blood flows therethrough and into the venous system. For example, and without limitation, the at least one lumen 156 may further comprise an internal balloon or resorbable stenosis as disclosed in International Patent Application No. PCT/US2006/029223, entitled "Devices and Methods for Controlling Blood Perfusion Pressure Using a Retrograde Cannula," filed Jul. 28, 2006, which is hereby incorporated by reference herein.

In at least one embodiment, the stenosis comprises an internal expandable balloon (not shown) positioned within the lumen 156 of the second catheter 150. In this at least one embodiment, the internal expandable balloon can be used to provide a pressure drop between the arterial and venous systems as is required to achieve the gradual arterialization of the target vein. The internal expandable balloon and the external expandable balloon 158 of the second catheter 150 may positioned concentrically or, alternatively, the internal expandable balloon and the expandable balloon 158 may be coupled with distinct portions of the second catheter 150. The internal expandable balloon may comprise any material suitable in the medical arts, including, without limitation, polyethylene, latex, polyestherurethane, polyurethane, sylastic, silicone rubber, or combinations thereof. Further, the internal expandable balloon may be in fluid communication with a tertiary lumen (not shown) disposed within the at least one lumen 156 of the second catheter 150. In this embodiment, the tertiary lumen is also in fluid communication with an internal balloon port that extends from the proximal end 152 of the second catheter 150. Accordingly, the internal balloon port can be easily accessed by a clinician, subcutaneously, percutaneously or otherwise, and the internal balloon port can be used to inflate or deflate the internal expandable balloon with minimal or no discomfort to the patient when the system 100 is in operation. Alternatively, the internal expandable balloon may be in fluid communication with the at least one lumen 156 of the second catheter 150. In this example, the arterial blood flow through the at least one lumen 156 functions to inflate and deflate the internal expandable balloon in conjunction with the systolic and diastolic components of a heartbeat.

The internal expandable balloon may be sized to a specific configuration in order to achieve the desired stenosis. In one embodiment, the size of the desired stenosis may be obtained by measuring the pressure at the tip of the distal end 156 of the second catheter 150 with the at least one sensor 166 while the internal expandable balloon is being inflated. Once the desired intermediate pressure is obtained, the internal expandable balloon volume may then be finalized and the vein is thereafter allowed to arterialize at the modified pressure for a defined period of time. At the end of the defined period (typically about 2-3 weeks), the internal expandable balloon may be removed from the at least one lumen 156 of the second catheter 150. Insertion and/or removal of the internal expandable balloon from the system 100 may be achieved through the internal balloon port and the related tertiary lumen of the second catheter 150. For example, if the internal expandable balloon is no longer necessary to control the pressure on the venous system because the arterialization of the vein is substantially complete, the internal expandable balloon can be deflated through use of internal balloon port and withdrawn from the system 100 through the tertiary lumen and the internal balloon port.

Other embodiments of the system 100 may comprise other suitable means for providing a stenosis within the at least one lumen 156 of the second catheter 150 such that a pressure drop is achieved in blood flowing therethrough. For example, while a stenosis can be imposed by inflation of the internal expandable balloon, it may also be imposed through positioning a resorbable material within the at least one lumen 156 of the second catheter 150. The resorbable stenosis may be comprised of a variety of materials including, for example and without limitation, magnesium alloy and polyols such as mannitol, sorbitol and maltitol. The degradation rate of the resulting resorbable stenosis will be dependent, at least in part, upon on what type of material(s) is selected to make-up the resorbable stenosis and the same may be manipulated to achieve the desired effect.

In addition to the aforementioned components of the autoretroperfusion system 100, the autoretroperfusion system 100 may further include a first graft 185 and a second graft 190 as shown in FIG. 3. In this embodiment, the first graft 185 is coupled with the proximal end 20 of the projection cannula 16 (that extends through the exterior arterial wall 116) and the connector 170. Further, the second graft 190 is coupled with the proximal end 152 of the second catheter 150 (positioned within the venous vessel wall 114) and the connector 170. Accordingly, in this at least one embodiment, the second graft 190 is capable of traversing the venous vessel wall 114 in such a manner that the anastomosis is sealed and no blood flow is allowed to leak from the anastomosed vein 114. In this manner, the first and second grafts 185, 190 facilitate the formation of an elongated anastomosis between the venous and arterial vessels 114, 116 and thereby relieve any pressure that may be applied to the two vessels 114, 116 due to the anastomosis formed therebetween. For example and without limitation, in at least one embodiment the combined length of the grafts 185, 190 and the connector 170 is about 6 centimeters. However, it will be understood that the grafts 185, 190 may comprise any length(s) so long as the dimensions allow for an anastomosis to form between the applicable vessels and a fully developed blood flow is achieved from the artery to the venous vessel of interest.

Alternatively, the autoretroperfusion system 100 may only comprise the second graft 190 in addition to the catheter 10, the second catheter 150 and the connector 170. In this embodiment, the connector 170 is coupled with the proximal end 20 of the projection cannula 16 and the second graft 190. Furthermore, the second graft 190 is further coupled with the proximal end 152 of the second catheter 150 such that the second graft 190 traverses an opening within the venous vessel wall 114 (see FIG. 5). The grafts 185, 190 may comprise any biocompatible, non-resorbable material having the necessary strength to support the surrounding tissue and withstand the pressure asserted by the blood flow therethrough. Furthermore, the grafts 185, 190 must exhibit the necessary flexibility to form an anastomosis between the vein and the artery within which the catheter 10 and the second catheter 150 are respectively housed. For example, and without limitation, the grafts 185, 190 may comprise any conventional implant including synthetic and natural prosthesis, grafts, and the like. The grafts 185, 190 may also comprise a variety of suitable materials, including those conventionally used in anastomosis procedures, including, without limitation, natural and synthetic materials such as heterologous tissue, homologous tissue, polymeric materials, Dacron, fluoropolymers, and polyurethanes. For example, and without limitation, the first and second grafts 185, 190 may comprise a material such as GORE-TEX (polytetraflouroethylene). The grafts 185, 190 may be coated with heparin or any other suitable anti-coagulant. Accordingly, the first graft 185 and the second graft 190 may be placed within a vessel or have blood flow therethrough for an extended period of time without inhibiting blood flow due to coagulation.

In at least one embodiment of the autoretroperfusion system 100, the components of the system 100 are available in a package. Here, the package may also contain at least one sterile syringe containing the fluid to be injected into the balloon port 62 to inflate the expandable balloon 58 of the catheter 10 and/or the balloon port 162 to inflate the expandable balloon 158 of the second catheter 150. Furthermore, the package may also contain devices to facilitate delivery of the autoretroperfusion system 100 such as venous and arterial access devices, a delivery catheter, a guidewire and/or mandrel, an introducer to maintain the catheter 10 in the collapsed position during delivery and, in those embodiments where a coil is used to arterialize the vein of interest, a pusher bar as is known in the art. The guidewire used to facilitate the delivery of the autoretroperfusion system 100 into a vessel by providing support to the components thereof. The guidewire may comprise any guidewire known in the art. Furthermore, the distal end of the guidewire may comprise a plurality of impedance electrodes that are capable of taking measurements of the size the vessel in which the guidewire is inserted through the use of impedance technology. Additionally, in at least one embodiment, the impedance electrodes may be further capable of communicating such measurements to the remote module 180 through telemetry or other wireless means in a manner similar to the at least one sensor 166 of the distal end 154 of the second catheter 150. In at least one embodiment, the distal end of the guidewire may comprise two tetrapolar sets of impedance electrodes disposed on its distal-most tip.

Based on the information gathered by the impedance electrodes, a clinician can obtain accurate measurements of a selective region of a vessel. In this manner, the expandable balloon 158 coupled with the distal end 154 of the second catheter 150 may be properly sized and the amount of fluid or gas needed to inflate the expandable balloon 158 can be determined prior to introducing the second catheter 150 into the vein of interest. For example, a clinician can use the plurality of impedance electrodes on the guidewire to obtain measurements of the size and shape of the sub-branches of the coronary sinus. Now referring to FIG. 5, components of a simultaneous selective autoretroperfusion system 300 are shown. The simultaneous selective autoretroperfusion system 300 (the "SSA system 300") are configured identically to the autoretroperfusion system 100 except that the SSA system 300 further comprises a third catheter 350 and a Y connector 320, both configured for placement within the venous vessel wall 114. Specifically, the SSA system 300 comprises the catheter 10, the second catheter 150, the third catheter 350, the connector 170, and the Y connector 320. It will be understood that the SSA system 300 can also further comprise the first graft 185 and/or the second graft 190, and the remote module 180 as described in connection with autoretroperfusion system 100. The third catheter 350 is configured for placement within the venous vessel wall 114 adjacent to the second catheter 150. The third catheter 350 is configured identically to the second catheter 150 and comprises a flexible tube having a proximal end 352, a distal end 354 and at least one lumen 356 extending between the proximal end 352 and the distal end 354. Both the proximal end 352 and the distal end 354 of the third catheter 350 are open and in communication with the at least one lumen 356 of the third catheter 350, thereby allowing blood to flow into the at least one lumen 356 through the proximal end 352 and out of the distal end 354 back into the venous vessel 114. The third catheter 350 may be any catheter known in the art that is capable of intravascular insertion and advancement through the venous system. The third catheter 350 may comprise any appropriate material, including without limitation, polyurethane or silicone rubber. In at least one embodiment, the third catheter 350 is configured to receive a guidewire 310 (see FIGS. 5 and 6) through the at least one lumen 356 in order to facilitate the intravascular delivery of the distal end 354 of the third catheter 350 into the desired location of the venous vessel 114. Furthermore, the third catheter 350 is coated with heparin or any other suitable anti-coagulant prior to insertion in order to facilitate the extended placement of the third catheter 350 within the venous vessel 114.

Figure 5:
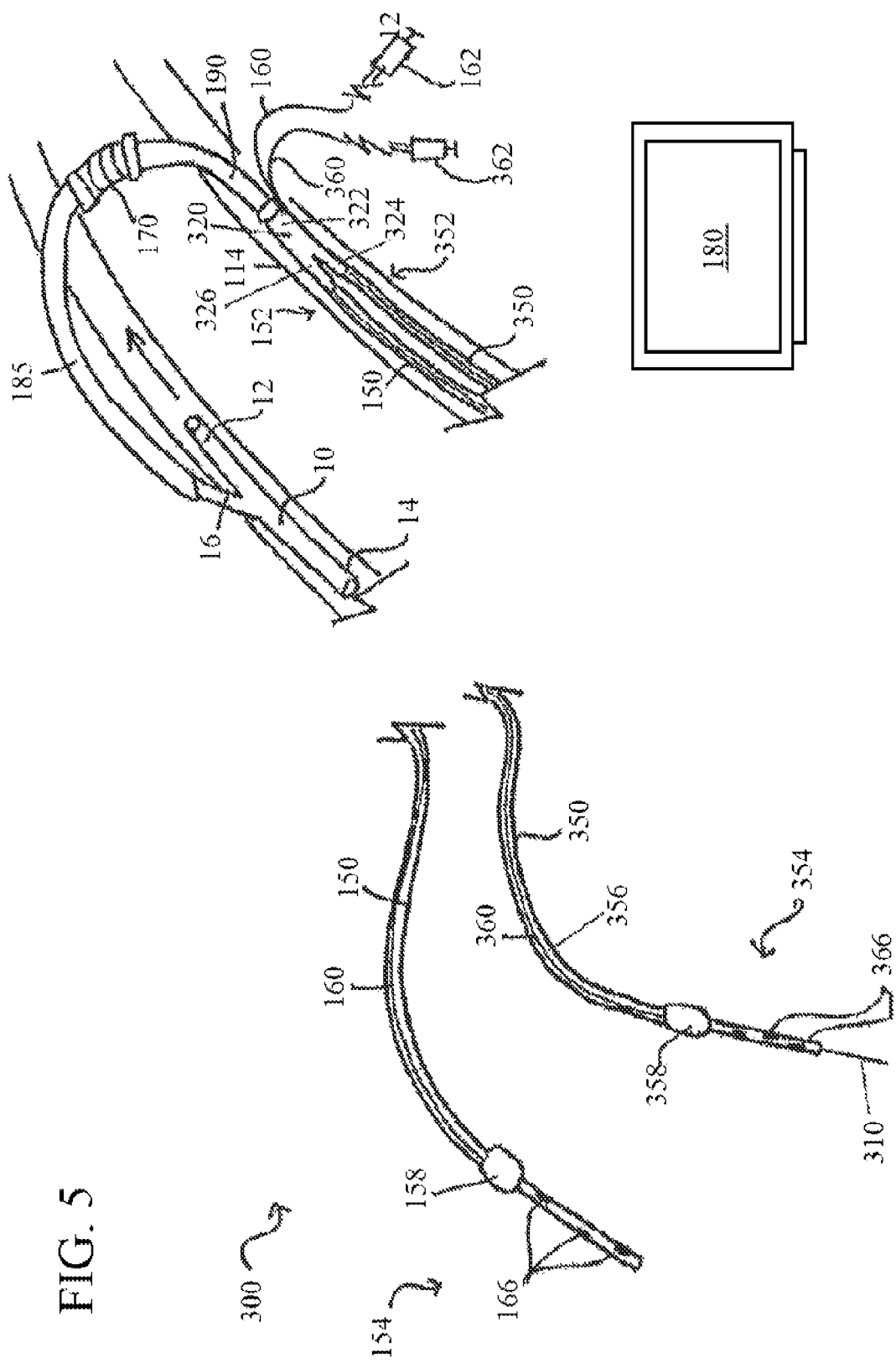
FIG. 5 shows the components of an autoretroperfusion system that can be used to deliver retroperfusion therapy to ischemic tissue, according to at least one embodiment of the present disclosure.

As shown in FIG. 5, the distal end 354 of the third catheter 350 further comprises an expandable balloon 358 coupled with the external surface of the third catheter 350. In operation, the expandable balloon 358 can be used to anchor the distal end 354 of the third catheter 350 in the desired location within the venous vessel wall 114. The expandable balloon 358 may be any expandable balloon that is appropriate for insertion within a vessel and can be formed of any material suitable for this function, including without limitation, polyethylene, latex, polyestherurethane, polyurethane, sylastic, silicone rubber, or combinations thereof. Similar to the expandable balloon 158 of the second catheter 150, the expandable balloon 358 is capable of being controlled by a clinician such that it can inflate and/or deflate to the proper size. The appropriate size of the expandable balloon 358 can be determined through any technique known in the art, including without limitation, by measuring the compliance of the expandable balloon 358 ex vivo or in vivo. Furthermore, when the guidewire 310 is used to facilitate the delivery of the distal end 354 of the third catheter 350 into the desired location within the venous vessel wall 114, the electrodes on the distal end of the guidewire 310 may be used to accurately measure the cross-sectional area of the venous vessel 114 such that the expandable balloon 358 can be precisely sized prior to insertion into the vein 114. In this at least one embodiment, the expandable balloon 358 is in fluid communication with a secondary lumen 360 disposed within the at least one lumen 356 of the third catheter 350. In this example, the secondary lumen 360 is coupled with a balloon port 362 that extends from the proximal end 352 of the third catheter 350. Accordingly, when the SSA system 300 is positioned within a patient, the balloon port 362 can be easily accessed by a clinician, subcutaneously, percutaneously or otherwise, and used to inflate or deflate the expandable balloon 358 with no or minimal invasion to the patient.

Similar to the second catheter 150, the distal end 354 of the third catheter 350 may further comprise at least one sensor 366 coupled therewith. The at least one sensor 366 may be configured identically to the at least one sensor 166 of the second catheter 150 and, accordingly, the at least one sensor 366 may be used to monitor the pressure of blood flow through the at least one lumen 356 of the third catheter 350 or the venous vessel 114 or to monitor the pH or the concentrations of carbon dioxide, lactate, or cardiac enzymes within the blood. Furthermore, the at least one sensor 366 is capable of communicating the data it gathers to the remote module 180 through the use of a wireless technology such that a clinician can easily access the gathered information on a real-time basis or otherwise. In at least one embodiment, the at least one sensor 366 is disposed on the distal end 354 of the third catheter 350 distally of the expandable balloon 358; however, it will be understood that the at least one sensor 366 may be disposed in any location on the distal end 354 of the third catheter 350. The Y connector 320 of the SSA system 300 comprises flexible material and has a proximal end 322, a distal end 324 and at least one lumen 326 extending between the proximal and distal ends 322, 324. The proximal end 322 of the Y connector 322 is open and configured to be securely coupled with the graft 190. The distal end 324 of the Y connector 322 comprises two open ends which extend from the body of the Y connector 322 in a substantially Y-shaped configuration. The two open ends of the distal end 324 of the Y connector 322 thereby divide the at least one lumen 326 into two separate channels and thus the blood flowing through the at least one lumen 326 is yet again bifurcated. The proximal end 152 of the second catheter 150 is coupled with one of the two open ends of the distal end 324 of the Y connector 322, thereby receiving a portion of the blood flow that flows through the at least one lumen 326 of the Y-connector. Similarly, the proximal end 352 of the third catheter 350 is coupled with the other open end of the distal end 324 of the Y connector 322 and, thus, the third catheter receives a portion of the blood flow that flows through the at least one lumen 326 of the Y-connector. In this manner, the SSA system 300 can be used to simultaneously retroperfuse more than one ischemic area of the body.

Figure 6:
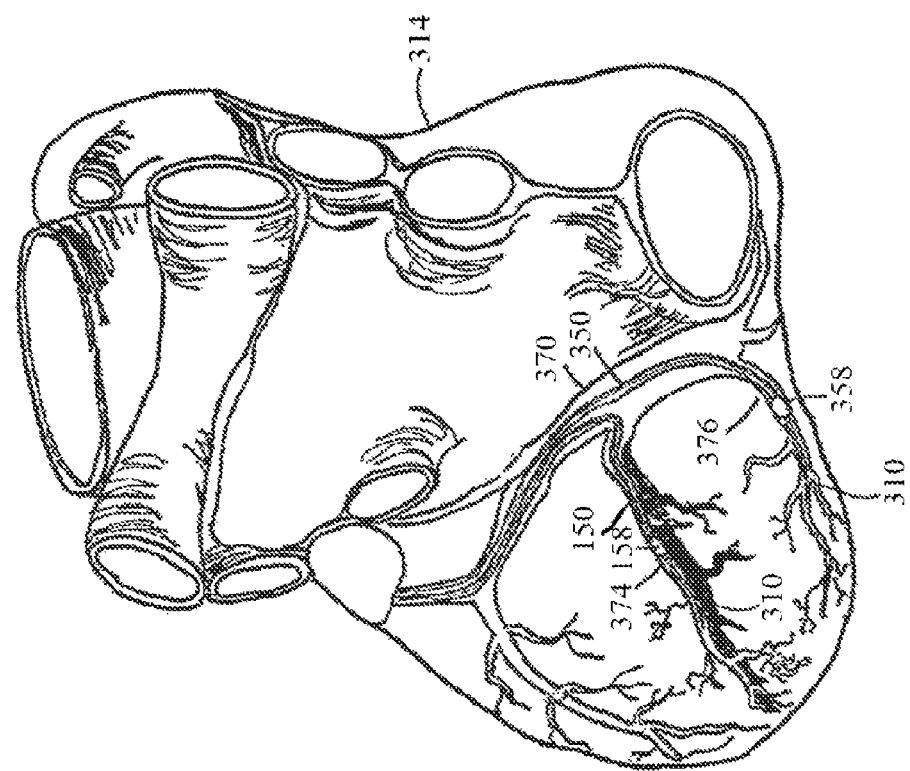
FIG. 6 shows a view of the base and diaphragmatic surface of a heart with the distal ends of two components of the autoretroperfusion system of FIG. 5 positioned therein such that the autoretroperfusion system can deliver simultaneous selective autoretroperfusion therapy thereto, according to at least one embodiment of the present disclosure.

In application, the second catheter 150 and the third catheter 350 are positioned adjacent to each other within the venous vessel wall 114 as shown in FIG. 5. Furthermore, the distal ends 154, 354 of the second and third catheters 150, 350, respectively, may be placed within different veins such that the arterial blood is delivered to selective portions of ischemic tissue. For example, as shown in FIG. 6, in at least one embodiment the SSA system 300 can be applied to a heart 314 to provide an arterial blood supply to two separate coronary veins, or sub-branches, simultaneously. In this at least one embodiment, the distal ends 154, 354 of the second and third catheters 150, 350 are both advanced through the coronary sinus 370. As the diameter of the coronary sinus 370 ranges from about 10 to about 20 millimeters, cannulating the coronary sinus 370 with both the second and third catheters 150, 350 does not occlude the normal antegrade flow of the blood therethrough. Upon reaching the veins or sub-branches of interest, the distal ends 154, 354 of the second and third catheters 150, 350 are each independently positioned within the veins of interest. In the example shown in FIG. 6, the second catheter 150 is positioned within the interventricular vein 374 and the distal end 354 of the third catheter 350 is positioned within the middle cardiac vein 376. As with autoretroperfusion system 100, the expandable balloons 158, 358 are inflated through balloon ports 162, 362, respectively (shown in FIG. 5), such that the distal ends 154, 354 of the second and third catheters 150, 350 are securely anchored in the desired location within the veins of interest. In this manner, the SSA system 300 can deliver controlled arterial blood flow to, and thus arterialize, two areas of the heart 314 simultaneously.

Figure 7:
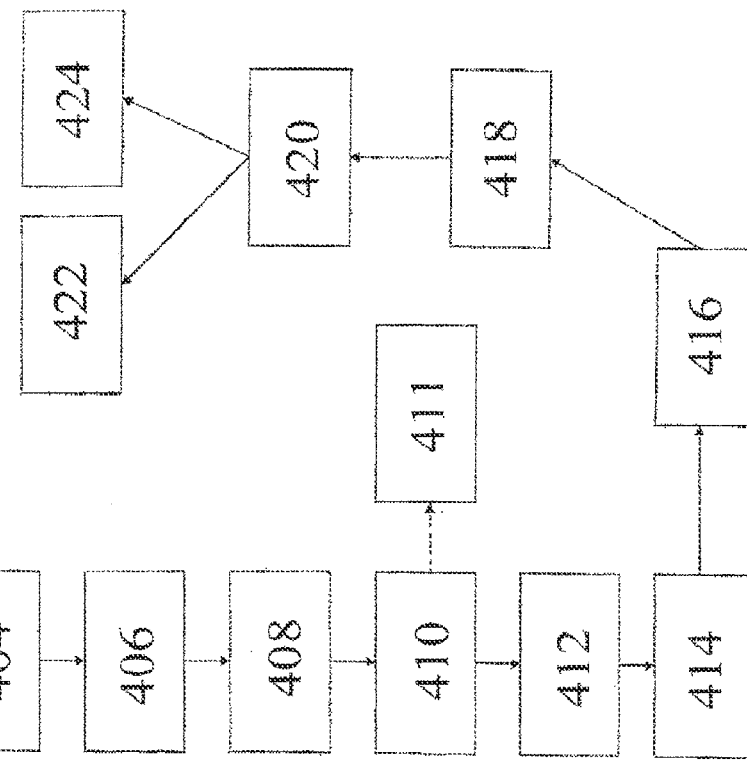
FIG. 7 shows a flow chart of a method for delivering autoretroperfusion therapy, according to at least one embodiment of the present disclosure.

In at least one embodiment of the SSA system 300, the components of the system 300 are available in a package. Here, the package may also contain sterile syringes with the fluids to be injected into the balloon ports 162, 362 to inflate the expandable balloons 158, 358, respectively. Furthermore, the package may also contain devices to facilitate delivery of the SSA system 300 such as arterial and venous access devices, a delivery catheter, at least two guidewires (configured as described in connection with the delivery of autoretroperfusion system 100), an introducer to maintain the catheter 10 in the collapsed position during delivery and, in those embodiments where a coil is used to arterialize the vein of interest, a pusher bar as is known in the art. Now referring to FIG. 7, a flow chart of a method 400 for performing automatic retroperfusion using the system 100 is shown. While the method 400 is described herein in connection with treating a heart through catheterization of the coronary sinus, it will be understood that the method 400 may be used to perform autoretroperfusion on any organ or tissue in need of retroperfusion treatment and/or other areas near the coronary sinus, such as the great cardiac vein, for example. Method 400, and the embodiments thereof, can be performed under local anesthesia and do not require any arterial sutures. Further, once implanted, the system 100 can deliver chronic treatment to the patient as the system 100 is capable of remaining within a patient's vascular system for an extended period of time. In this manner, the system 100 and method 400 can be used to treat no-option patients and greatly enhance their quality of life. As shown in FIG. 7, in one approach to the method 400, at step 402 an artery 502 of interest is percutaneously punctured under local anesthesia with a conventional artery access device or as otherwise known in the art. For example and without limitation, in at least one embodiment, an 18 gauge needle is inserted into the femoral or subclavian artery. At step 404, the catheter 10 housed in a collapsed position within an introducer 504 (see FIG. 8A) is inserted into the artery 502 of interest. After the distal end 14 of the catheter 10 is positioned in the desired location within the artery 502, the introducer 504 is proximally withdrawn from the artery 502 as shown in FIG. 8B, leaving the catheter 10 positioned therein.

In at least one embodiment, the projection cannula 16 is configured such that when the introducer 504 is withdrawn in a proximal direction, the proximal end 12 of the catheter 10 is released from the introducer 504 before the proximal end 20 of the projection cannula 16 is released from the introducer 504. In this manner, the proximal end 12 of the catheter 10 is delivered within the interior of the arterial wall 502, while the projection cannula 16 remains housed within the interior of the introducer 504 as shown in FIG. 8C. Furthermore, because the introducer 504 no longer applies downward pressure to the projection cannula 16 relative to the proximal end 12 of the catheter 10, the projection cannula 16 is allowed to shift from the collapsed position to the expanded position and therefore extends in a direction that is not parallel with the artery 502 or the body of the catheter 10. In this manner, as shown in FIGS. 8C and 8D, the proximal end 20 of the projection cannula 16 is directed through the opening formed in the arterial wall 502 by the introducer 504. Accordingly, when the catheter 10 is positioned within the artery 502, the antegrade blood arterial blood flow is allowed to continue through the artery 502 through the proximal end 12 of the catheter 10, while only a portion of the arterial blood is rerouted through the projection cannula 16 and into the veins 506 of interest. In this manner, the normal blood flow through the artery 502 is not inhibited by operation of the autoretroperfusion system 100. Furthermore, in addition to bifurcating the blood flowing through the artery 502, the projection cannula 16 traversing the arterial wall 502 further functions to anchor the catheter 10 in the desired position within the artery 502.

In the embodiment where the catheter 10 further comprises the expandable balloon 58 (see FIG. 1), step 404 may further comprise inflating the expandable balloon 58 to the desired size by injecting fluid into the balloon port 62. In this manner, the expandable balloon 58 functions to further anchor the catheter 10 in the desired location within the artery 502 and seal the opening in the artery 502 through which the projection cannula 16 projects (see FIG. 8E). At step 406, a vein 506 of interest is percutaneously punctured under local anesthesia with a conventional venous access device or as otherwise known in the art. For example and without limitation, in at least one embodiment, an 18 gauge needle is inserted into the femoral or subclavian vein. At step 408, a delivery catheter 508 is inserted into and advanced through the vein 506 to catheterize the coronary sinus ostium. A guidewire 510 is then inserted at step 410 into the delivery catheter 510 and advanced into the lumen of the vein 506 through the distal end of the delivery catheter 510. Furthermore, the guidewire 510 is advanced into the region of interest by use of x-ray (i.e. fluoroscopy), direct vision, transesophageal echocardiogram, or other suitable means or visualization techniques.

Figure 9:
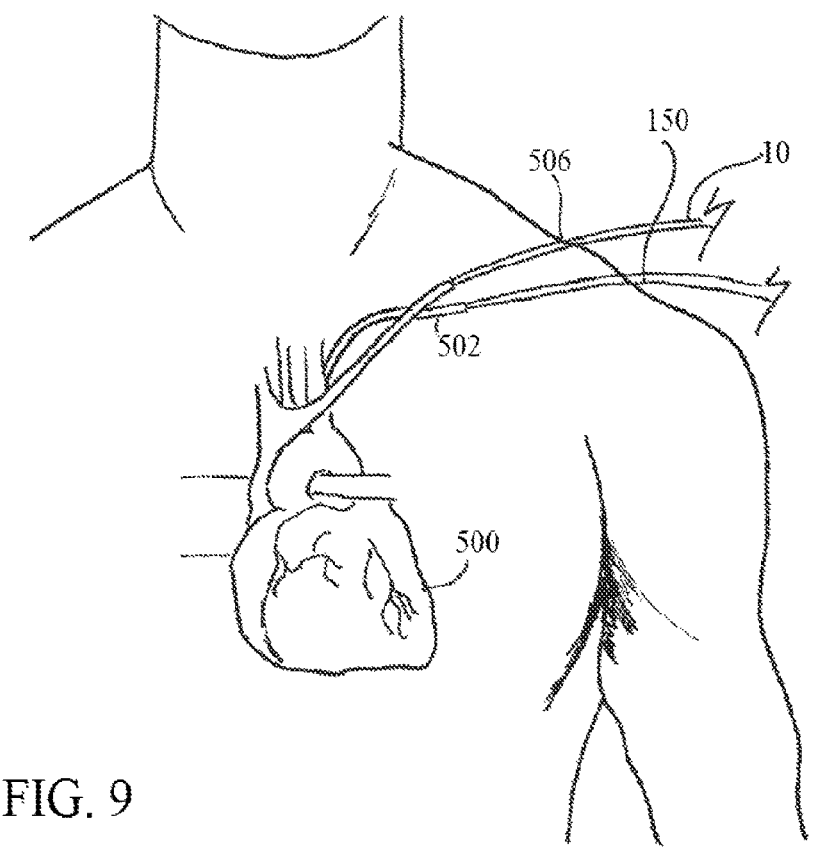
FIG. 9 shows a schematic view of the autoretroperfusion system of FIG. 5 as applied to a heart, according to at least one embodiment of the present disclosure.
Figure 10:
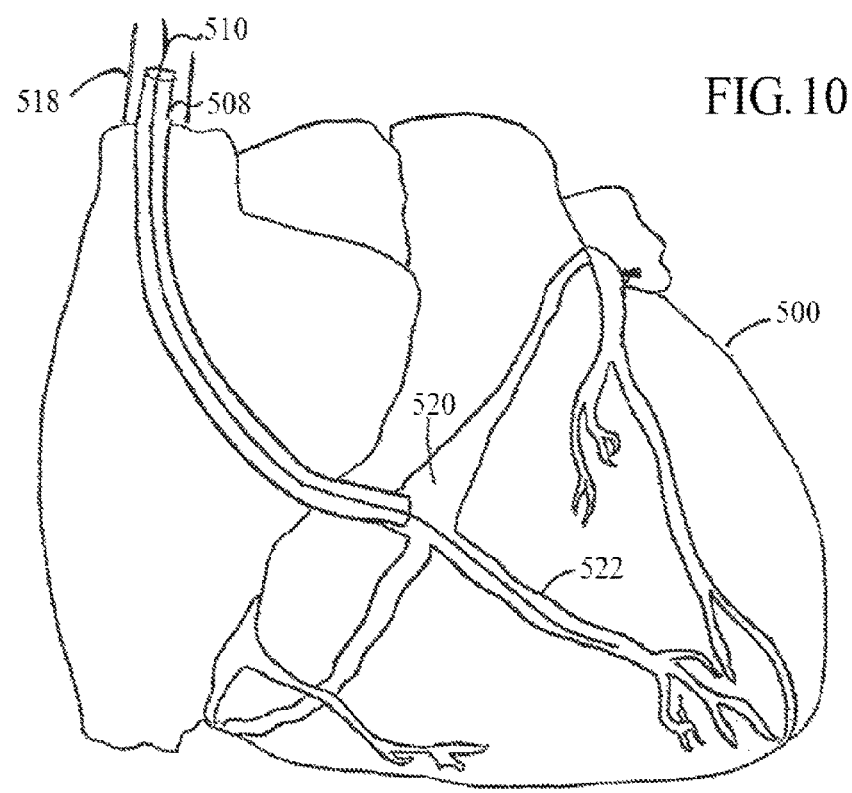
FIG. 10 shows a schematic view of the autoretroperfusion system of FIG. 5 as applied to a heart, according to at least one embodiment of the present disclosure.

FIGS. 9 and 10 show schematic views of the method 400 as applied to a heart 500. Specifically, in this at least one embodiment, at steps 402 and 404 the artery 502, which in FIG. 9 comprises the subclavian artery, is punctured and the catheter 10 is inserted and positioned therein. Further, at step 406 the vein 506, which in FIG. 9 comprises the subclavian vein, is punctured and at step 408 the delivery catheter 508 is advanced through the superior vena cava 518 and into the coronary ostium of the coronary sinus 520. As shown in FIG. 10, at step 410, the guidewire 510 is advanced through the coronary sinus 520 and into the vein of interest, which, in this at least one embodiment, comprises the posterior vein 522 of the heart 500.

Figure 11:
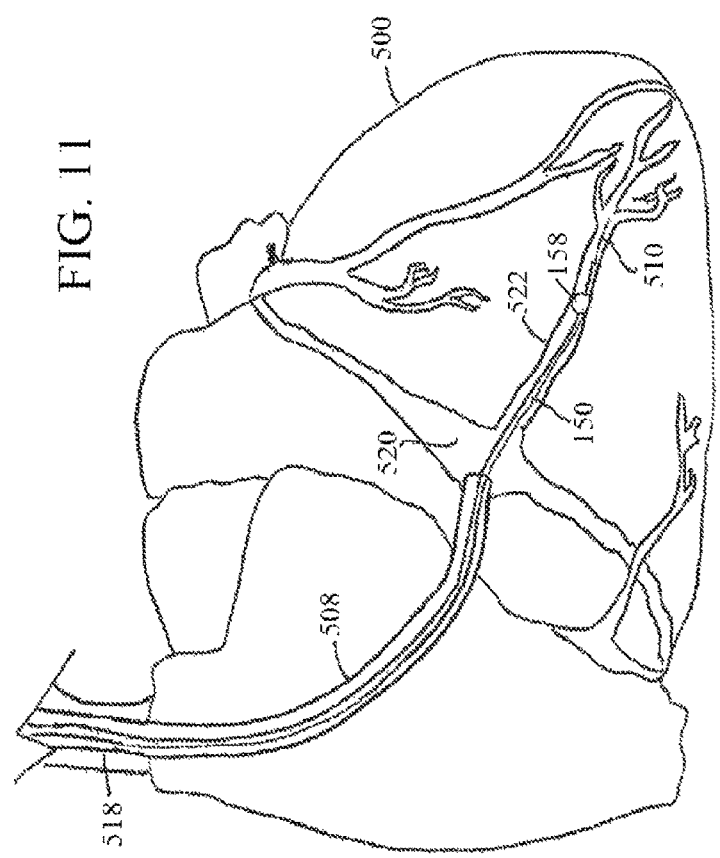
FIG. 11 shows a schematic view of a step of the method of FIG. 7 as the method is applied to a heart, according to at least one embodiment of the present disclosure.

Now referring back to FIG. 7, the guidewire 510 inserted into the vein 506 at step 410 may further comprise a plurality of impedance electrodes as previously described herein. In this approach, the guidewire 510 may be used at optional step 411 to determine the size of the vessel of interest through use of the plurality of impedance electrodes disposed thereon. In this manner, a clinician can use the measurements generated by the impedance electrodes to select a properly sized expandable balloon 158 for use in connection with the second catheter 150. By using a precisely sized expandable balloon 158 and inflation volume, the clinician can ensure that the distal end 154 of the second catheter 150 is securely anchored within the vessel of interest without imposing an undue force on the venous vessel walls. After the guidewire 510 has been advanced into the vessel of interest at step 410 and, optionally, the dimensions of the vessel of interest have been measured at step 411, the method 400 advances to step 412. At step 412, the distal end 154 of the second catheter 150 is inserted into the delivery catheter 508 over the guidewire 510. Accordingly, the guidewire 510 is slidably received by the at least one lumen 156 of the second catheter 150. The distal end 154 of the second catheter 150 is then advanced over the guidewire 510 to the region of interest and the expandable balloon 158 of the second catheter 150 is inflated to anchor the distal end 154 within the targeted vessel. FIG. 11 shows a schematic view of the method 400, as applied to the heart 500, after step 412 has been completed. It will be understood that at any point after the distal end 154 of the second catheter 150 is positioned and anchored within the desired location in the targeted vessel, the delivery catheter 508 and the guidewire 510 may be withdrawn from the vein of interest. After the distal end 154 of the second catheter 150 is secured within the targeted vessel, at step 414 the anastomosis between the vein 506 and the artery 502 is formed. Specifically, in at least one approach, the proximal end 20 of the projection cannula 16 of the catheter 10 is coupled with the proximal end 152 of the second catheter 150 by way of the connector 170. In the at least one embodiment of the system 100 comprising the first graft 185 and the second graft 190, the connector 170 may be coupled with the catheter 10 and the second catheter 150 via the first graft 185 and the second graft 190 to form an elongated anastomosis. Alternatively, in yet another approach, the connector 185 may be coupled with the catheter 10 via the proximal end 20 of the projection cannula 16 and the second catheter 150 via only the second graft 190. It will be understood that any combination of the catheter 10, the second catheter 150 and the first and second grafts 185, 190 may be used in connection with the connector 170 to form the desired anastomosis between the vein 506 and the artery 502.

After the anastomosis is formed and the arterial blood is allowed to flow through the anastomosis and thereby through the connector 170, at step 416 the connector 170 measures the flow rate, pressure and any other desired data of the arterial blood flow. The connector 170 transmits the collected data to the remote module 180 either through intravascularly placed leads or wirelessly, through telemetry or other means. In this manner, a clinician may easily view the blood flow data on the remote module 180 and assess the degree of pressure drop that will be required to preserve and gradually arterialize the vein 506. At step 418, the pressure of the arterial blood flow through the system 100 is modified to transmit the desired pressure to the venous system. In this step 418 the pressure modification can be achieved through a clinician modifying the means of regulating the blood flow of the connector 170 through remote means or, in at least one embodiment of the system 100, inflating the internal expandable balloon of the second catheter 150 using the internal balloon port in order to partially occlude the flow of arterial blood through the at least one lumen 156 of the second catheter 150. Furthermore, in at least one alternative embodiment of the system 100, a clinician may deliver a resorbable stenosis configured to achieve the necessary pressure drop into the at least one lumen 156 of the second catheter 150 through means known in the art. Alternatively, as previously described in connection with autoretroperfusion system 100, the remote module 180 may further comprise a computer or other processing means capable of being programmed to automatically analyze the data received from the connector 170 and, based on such data, determine the proper degree of adjustment required in the blood pressure flowing through the anastomosis. In this embodiment, at step 418, the remote module 180 automatically adjusts the means of regulating the blood flow of the connector 170 to achieve the desired pressure drop. In this manner, the desired pressure drop between the arterial system and the venous system is immediately achieved and the risk of venous rupture is significantly reduced. In step 420 the method 400 allows the arterial blood having a modified pressure to irrigate the vein 506 for a period of time such that the vein 506 properly arterializes. For example, and without limitation, the patient's venous system may be subjected to the reduced arterial pressure for about fourteen days to allow the vein 506 to adapt to the elevated blood pressure flowing therethrough.

After arterialization of the vein 506 is achieved, at step 422 the patient may optionally undergo a coronary venous bypass graft surgery and the components of the autoretroperfusion system 100 may be removed. However, as previously discussed, even with a properly arterialized vein 506, many patients that require retroperfusion therapy may still not be candidates for a coronary vein bypass graft surgery. In the event that the patient is unable to tolerate such a procedure, after the vein 506 has arterialized at step 420, the method 400 can progress directly to step 424. At step 424, the pressure modification of the arterial blood flowing through the second catheter 150 is ceased. Accordingly, pre-arterialized veins 506 are subjected to the full arterial pressure of the blood flowing through the anastomosis and second catheter 150. In at least one embodiment, a clinician can cease the pressure modification by adjusting the controller 170. Alternatively, in the at least one embodiment where the controller 170 can be automatically adjusted by the remote module 180, the remote module 180 can automatically adjust the controller 170 after the veins 506 have pre-arterialized. Further, where the pressure drop is achieved through the use of an internal expandable balloon positioned within the at least one lumen 156 of the second catheter, the clinician may deflate the internal expandable balloon through the internal balloon port and thereafter withdraw the deflated internal expandable balloon through the tertiary lumen of the second catheter and the internal balloon port. In yet another embodiment where a resorbable stenosis is used to achieve the pressure drop in the arterial blood as it flows through the second catheter 150, the resorbable stenosis can be configured to dissolve after the desired period of time, thereby gradually decreasing the influence the resorbable stenosis has on the pressure of the blood flowing through the at least one lumen 156 of the second catheter over a period of time. Accordingly, the autoretroperfusion system 100 can remain chronically implanted within the patient to deliver oxygen-rich blood to a targeted area of tissue over an extended period of time.

Figure 12:
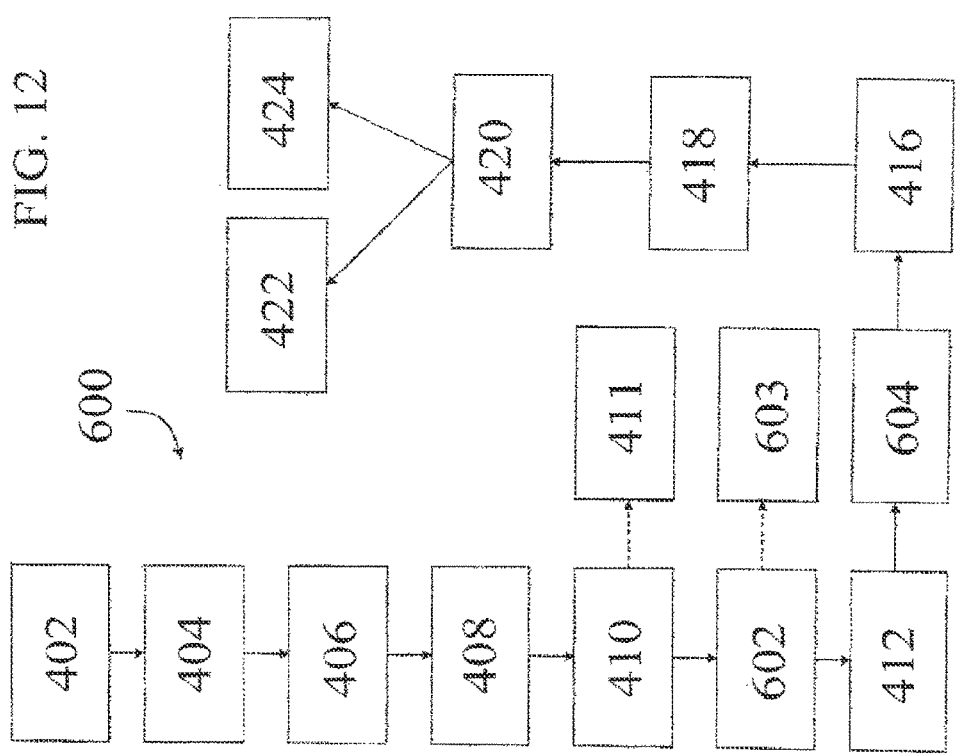
FIG. 12 shows a flow chart of a method for delivering simultaneously selective autoretroperfusion therapy, according to at least one embodiment of the present disclosure.

Now referring to FIG. 12, a flow chart of a method 600 for performing simultaneous selective retroperfusion using the SSA system 300 is shown. While the method 600 is described herein in connection with treating a heart 500 through catheterization of the coronary sinus 520, it will be understood that the method 600 may be used to perform autoretroperfusion on any organ or tissue in need of retroperfusion treatment. The reference numerals used to identify the steps of method 600 that are included in the description of method 400 designate like steps between the two methods 400, 600. As such, like steps between the two methods 400, 600 will not be discussed in detail with respect to the method 600 and it will be understood that such description can be obtained through the description of the method 400. Method 600, and the embodiments thereof, can be performed under local anesthesia and does not require arterial sutures. Further, once implanted, the SSA system 300 can deliver simultaneous chronic treatment to multiple ischemic locations as the system 300 is capable of remaining within a patient's vascular system for an extended period of time and selectively retroperfusion more than one sub-branch of a vein 506. The method 600 progresses through steps 402 through 410 as previously described in connection with the method 400. After the guidewire 510 is advanced through the coronary sinus 520 and into the first vein of interest, a second guidewire 610 is inserted at step 602 into the delivery catheter 508 adjacent to the guidewire 510, and advanced into the lumen of the vein 506 through the distal end of the delivery catheter 510. The second guidewire 610 is then advanced into a second region of interest by use of x-ray (i.e. fluoroscopy), direct vision, transesophageal echocardiogram, or other suitable means or visualization techniques. The second guidewire 610 is configured similar to the guidewire 510 and is capable of functioning the in the same manner.

Figure 13:
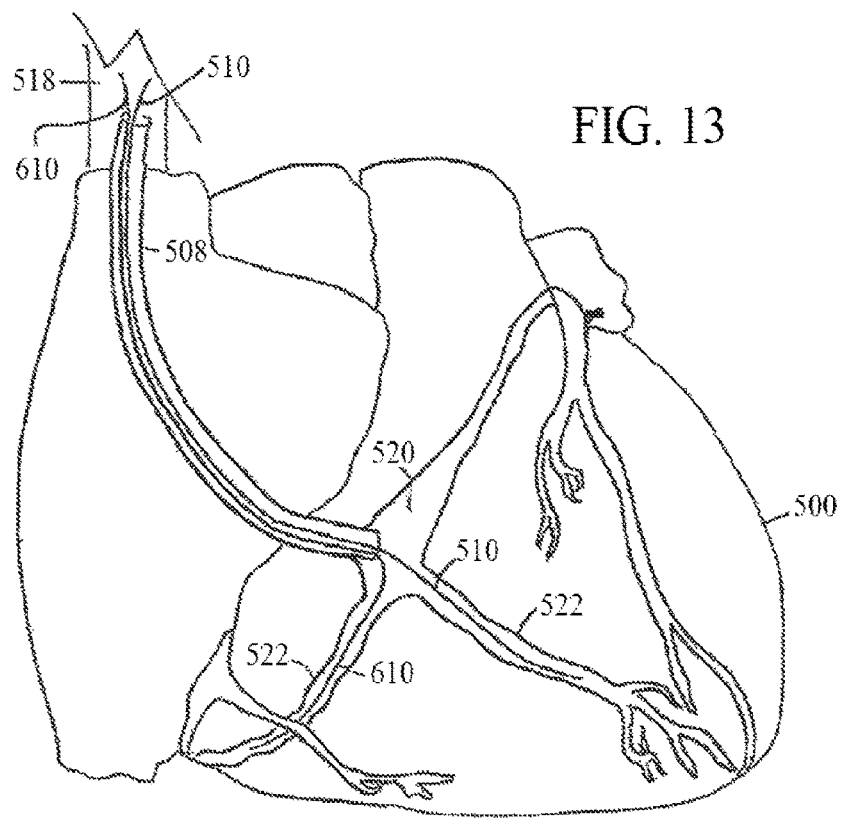
FIG. 13 shows a schematic view of a step of the method of FIG. 12 as the method is applied to a heart, according to at least one embodiment of the present disclosure.
Figure 14:
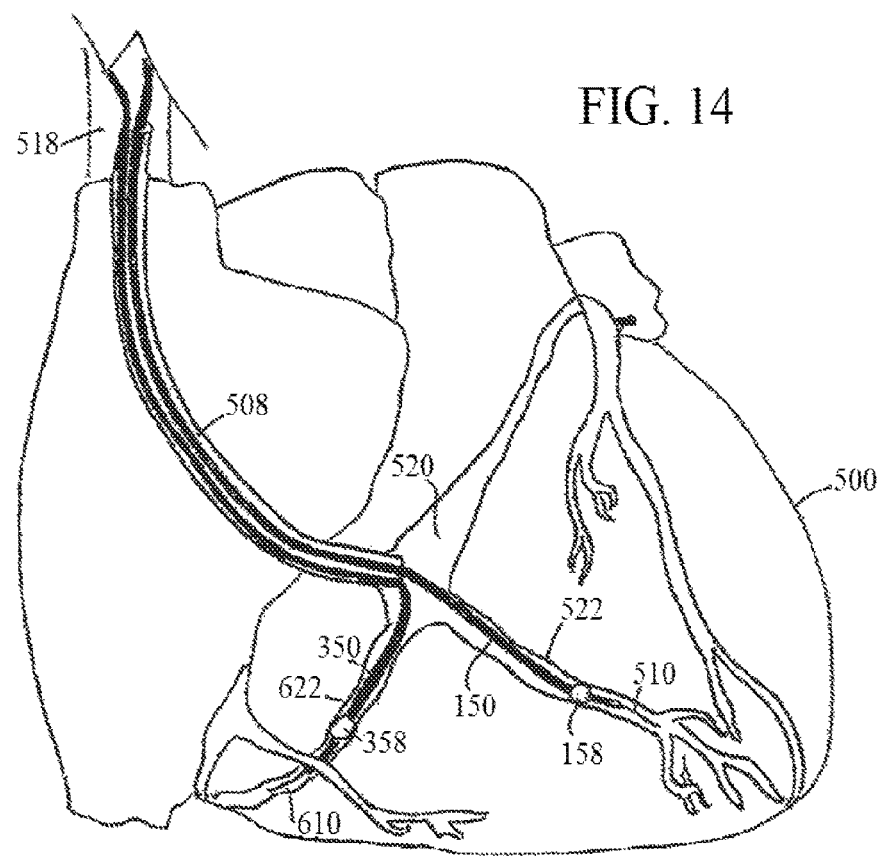
FIG. 14 shows a schematic view of a step of the method of FIG. 12 as the method is applied to a heart, according to at least one embodiment of the present disclosure.

FIG. 13 shows a schematic view of the method 600 as applied to a heart 500. Specifically, in this at least one embodiment, FIG. 13 shows the method 600 at step 602 wherein the guidewire 510 is inserted a first vein of interest, which comprises the posterior vein 522 of the heart 500, and the second guidewire 610 is inserted into a second vein of interest, which comprises the interventricular vein 622 of the heart 500. Now referring back to FIG. 12, the guidewire 610 inserted into the second vein of interest in step 602 may further comprise a plurality of impedance electrodes as previously described with respect to the guidewire 510. In this embodiment, the guidewire 610 may be used at optional step 603 to determine the size of the second vessel of interest through use of the plurality of impedance electrodes disposed thereon. In this manner, a clinician can use the measurements generated by the impedance electrodes to select a properly sized expandable balloon 358 for use in connection with the third catheter 350. By using a precisely sized expandable balloon 358 and inflation volume, a clinician can ensure that the distal end 354 of the third catheter 350 is securely anchored within the second vessel of interest without imposing an undue force on the venous vessel walls. After the guidewire 610 has been advanced into the second vessel of interest at step 602 and, optionally, the dimensions of the second vessel of interest have been measured at step 603, the method 600 advances to step 412 wherein the second catheter 150 is inserted over the guidewire 510 as described in connection with method 400. At step 604, the distal end 354 of the third catheter 350 is inserted into the delivery catheter 508 over the second guidewire 610. Accordingly, the second guidewire 610 is slidably received by the at least one lumen 356 of the third catheter 350. The distal end 354 of the third catheter 350 is then advanced over the second guidewire 610 to the second region of interest and the expandable balloon 358 of the third catheter 350 is inflated to anchor the distal end 354 within the targeted vessel. FIG. 14 shows a schematic view of the method 600 at step 604 as applied to the heart 500. It will be understood that at any point after the distal ends 154, 354 of the second and third catheters 150, 350 are positioned and anchored in the desired locations within the targeted vessels, the delivery catheter 508 and the guidewires 510, 610 may be withdrawn from the vein 506.

After both the distal end 154 of the second catheter 150 and the distal end 354 of the third catheter 350 are secured within the targeted vessels, the method 600 proceeds to step 414 where the anastomosis is formed between the vein 506 and the artery 502 as described in connection with method 400. Thereafter, the method 600 advances through steps 416 through 424 as described in connection with the method 400. Furthermore, at step 418, it will be recognized that a clinician can independently adjust the pressure drop through the second and third catheters 150, 350 in the event that an internal expandable balloon is used in either or both catheters 150, 350 or resorbable stenosis are employed within the at least one lumens 156, 356 of the second and third catheters 150, 350. Alternatively, in the at least one embodiment where the controller 170 comprises a means for regulating the blood flow through the anastomosis, the pressure of the arterial blood flowing through both the second and third catheters 150, 350 may be substantially the same. As described herein, the method 600 may be used to simultaneously and immediately treat two different ischemic areas of a tissue through the use of one minimally to non-invasive procedure. Furthermore, the method 600 can provide no-option patients with a viable treatment option that is not associated with contraindications for congestive heart failure, diabetes, or drug treatment.

Figure 15:
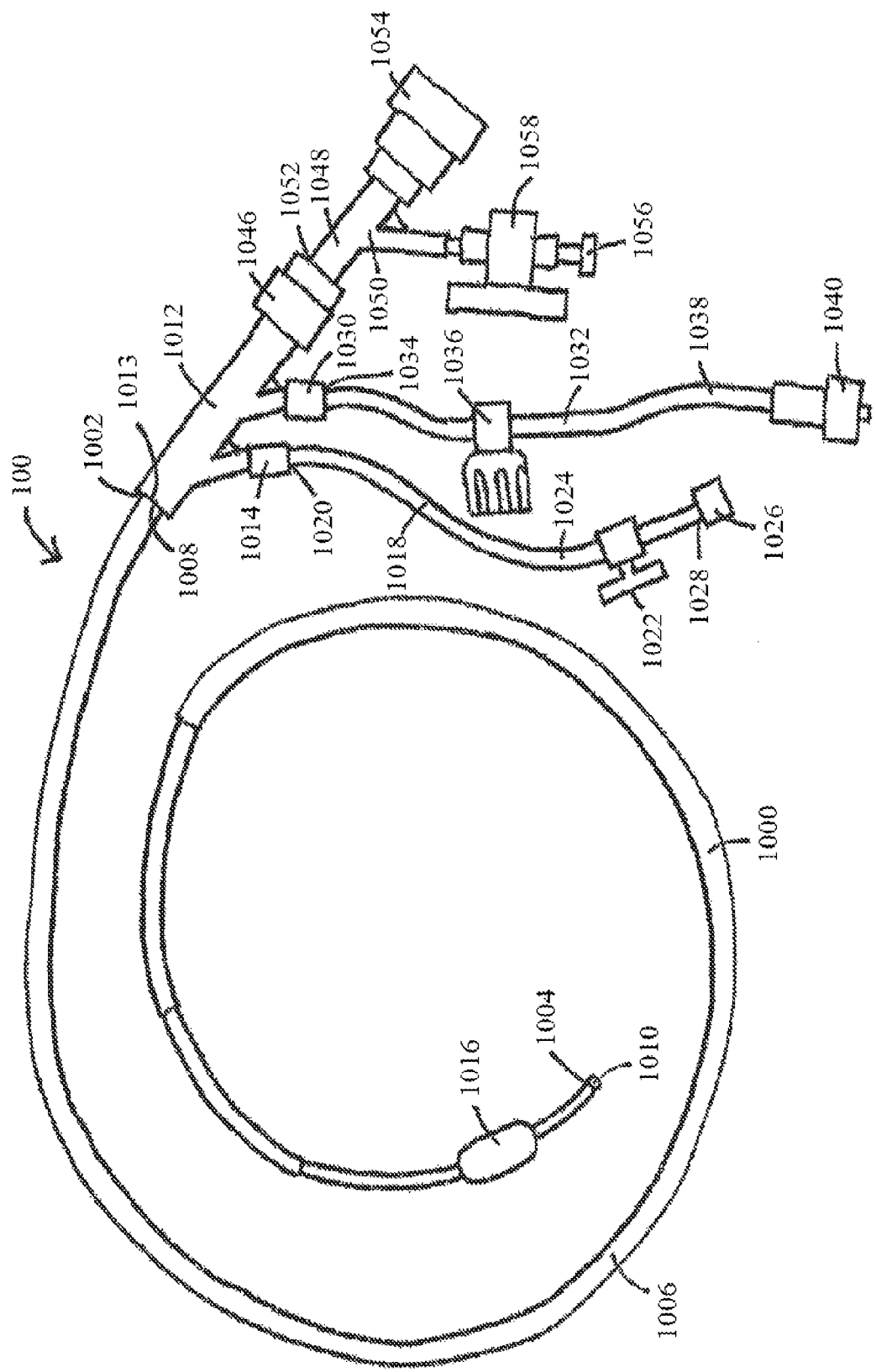
FIG. 15 shows an exemplary retroperfusion system, according to at least one embodiment of the present disclosure.
Figure 16:
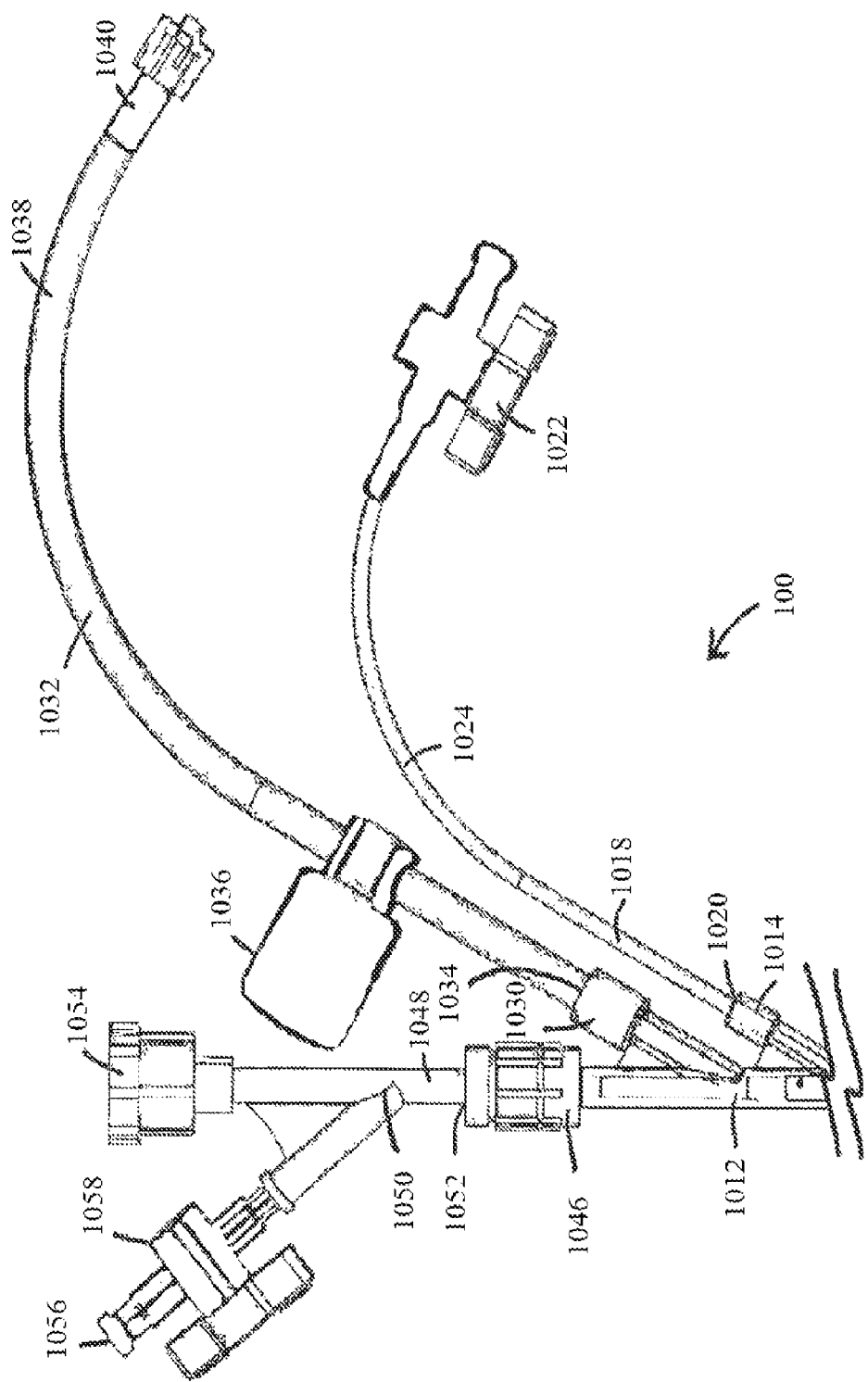
FIG. 16 shows a portion of an exemplary retroperfusion system, according to at least one embodiment of the present disclosure.

An additional embodiment of a perfusion system 100 of the present disclosure is shown in FIG. 15. As shown in FIG. 15, system 100 comprises a first catheter 1000 having a distal end 1002, a proximal end 1004, and defining a lumen 1006 therethrough, wherein at least a portion of first catheter 1000 is configured for insertion into a body of a patient, such as into a patient's heart or a patient's vein, for example. First catheter 1000, after insertion into a patient's vein or heart, for example, is capable of providing arterial blood (which is relatively rich in oxygen and other nutrients) thereto by way of transfer of arterial blood from, for example, a patient's artery, as described below, into a proximal catheter opening 1008, through lumen 1006, and out of distal catheter opening 1010. In such a fashion, for example, a system 100 can be referred to as an autoretroperfusion system 100, noting that no outside pumps are necessary (as the patient's own heart serves as the pump), and due to the retrograde nature of the perfusion with respect to such a use. Exemplary uses, as provided in detail herein, are to provide arterial blood, using system 100, to a patient's femoral vein, internal jugular vein, subclavian vein, and/or brachial cephalic vein. In an exemplary embodiment, first catheter 1000 may be tapered toward distal end 1002 to facilitate insertion into a patient. In at least one embodiment of system 100, and as shown in FIGS. 15 and 16, system 100 comprises a coupler 1012 having an outlet port 1013 and one or more additional ports to facilitate connection outside of the patient's body. For example, and as shown in FIGS. 15 and 16, coupler 1012 comprises an inflation port 1014, whereby fluid and/or gas introduced into inflation port 1014 can be used to inflate an expandable balloon 1016 positioned along first catheter 1000 at or near the distal end 1004 of first catheter 1000. As shown in the figures, and in at least one embodiment, an inflation tube 1018 may be coupled to inflation port 1014 at a distal end 1020 of inflation tube 1018, whereby inflation tube 1018 may also have an optional flow regulator 1022 positioned relative thereto to regulate the flow and/or pressure of fluid and/or gas in and out of a lumen 1024 of inflation tube 1018 to inflate and deflate expandable balloon 1016. Inflation tube 1018 may further comprise a proximal connector 1026 configured to receive fluid and/or gas from a fluid/gas source (not shown), whereby proximal connector 1026 can be positioned at or near a proximal end 1028 of inflation tube 1018, for example. Inflation of expandable balloon 1016, for example, can be used to anchor first catheter 1000 to a desired position within a luminal organ of a patient. An exemplary coupler 1012 of the present disclosure further comprises an arterial blood port 1030 configured to receive arterial/oxygenated blood from, for example, an arterial blood tube 1032 coupled thereto at or near a distal end 1034 of arterial blood tube 1032. As shown in FIGS. 15 and 16, a blood flow regulator 1036 may be positioned relative to arterial blood tube 1032 and operate to regulate the flow and/or pressure of arterial/oxygenated blood flow therethrough. In at least one embodiment, blood flow regulator 1036 comprises a rotatable dial capable of rotation to apply and/or remove pressure to/from arterial blood tube 1032 to regulate the flow and/or pressure of blood through a lumen 1038 of arterial blood tube 1032 and/or to adjust pressure therein based upon identified blood pressure measurements. Such a blood flow regulator 1036, for example, can be used to control blood pressure to limit injury to the patient's luminal organs (such as the patient's venous system and/or myocardium) and/or to minimize potential edema with respect to the same luminal organs. Arterial blood tube 1032 may further comprise a proximal connector 1040 configured to receive arterial/oxygenated blood from a blood supply, whereby proximal connector can be positioned at or near a proximal end 1040 of arterial blood tube 1032, for example. A coupler catheter 1042, as shown in the component block diagram of system 100 shown in FIG. 17, may be used to couple arterial blood tube 1032 to a blood supply 1044, which, as described herein, could be a patient's own artery using the patient's heart as a pump, or could be an external supply that provides blood to arterial blood tube 1032, which may then be used in connection with an apparatus to remove blood from the patient as well.

Figure 17:
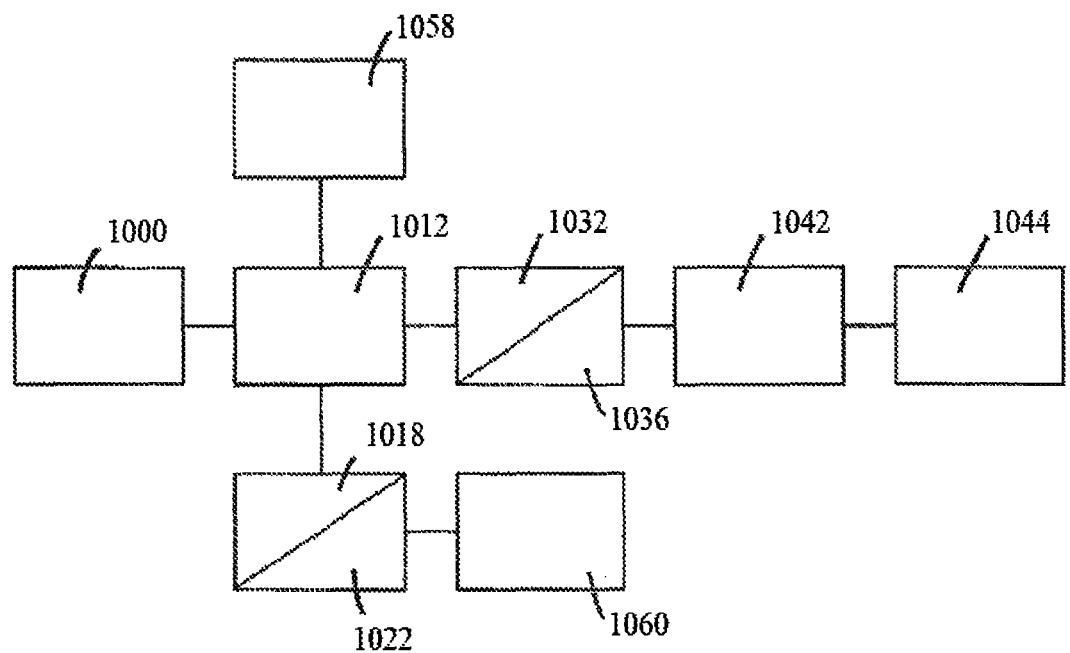
FIG. 17 shows a block diagram of components of an exemplary retroperfusion system coupled to a blood supply, according to at least one embodiment of the present disclosure.

Furthermore, and in at least one embodiment, an exemplary coupler 1012 of the present disclosure further comprises a medicament port 1046 configured to receive a medicament, saline, and/or the like, so that the same can enter the patient by way of first catheter 1000. Medicament port 1046, as shown in FIGS. 15 and 16, may receive a medicament tube 1048 defining a lumen 1050 therethrough, whereby a distal end 1052 of medicament tube 1048 can couple to medicament port 1046 so that a medicament, saline, and/or the like can be introduced from a medicament source (not shown) coupled to medicament tube 1052 at or near a proximal end 1054 of medicament tube 1048. Exemplary medicaments may include, but are not limited to, fibrinolitic drugs, cardiotonic drugs, antirrhytmic drugs, scavengers, cells or angiogenic growth factors, for example, through the coronary vein or another luminal organ. In at least one embodiment, and as shown in FIGS. 15 and 16, medicament tube 1048 can be branched, whereby a second proximal end 1056 of medicament tube 1048 can receive a medicament and control the flow of medicament therethrough, for example, by way of a medicament regulator 1058 positioned relative to medicament tube 1048, for example. Furthermore, one or more of proximal end 1054 and second proximal end 1056 may be configured to receive a wire therein, such as, for example, a 0.035" guidewire and/or a 0.014" pressure wire. As generally referenced herein, any blood, air, fluid, medicament, wire, etc. that enters coupler 1012 by way of inflation port 1014, arterial blood port 1030, and/or medicament port 1046 and eventually enters a lumen of first catheter 1000 will enter one or more of said ports of coupler 1012 and exit outlet port 1013 at the time of entry into first catheter 1000. FIG. 17, as referenced above, is a block diagram of various components of an exemplary system 100 of the present disclosure. As shown therein, an exemplary embodiment of a system 100 of the present disclosure comprises a first catheter 1000, a coupler 1012, an arterial blood tube 1032 with a blood flow regulator 1036, and a coupler catheter 1042 configured to for connection to a blood supply 1044, wherein the blood supply may or may not be considered as part of a formal system 100. In addition, an exemplary system 100 may comprise an inflation tube 1018 with a flow regulator 1022, whereby an end of inflation tube 1018 is configured for connection to a gas/liquid source 1060. Various embodiments of systems 100 of the present disclosure may have more or less components than shown in FIG. 17, and exemplary embodiments of systems 100 of the present disclosure may be configured to engage various embodiments of catheters 10 as referenced herein.

In use, for example, first catheter 1000 of system 100 may be positioned within a luminal organ of a patient within the patient's venous system. Inflation of expandable balloon 1016 to secure first catheter 1000 can not only provide oxygenated arterial blood to the patient's venous system, but can also continue to allow coronary venous return to continue due to the selective autoretroperfusion nature of an exemplary embodiment of system 100 and use thereof and due to the redundancy of the patient's venous system. In the event that an increased pressure, edema, or other undesired condition may occur at or near the site of inflated expandable balloon 1016, a user of system 100 could, if desired, temporarily deflate expandable balloon 1016 to allow the increased pressure and or edema to alleviate itself. For example, system 100 could be used for a relatively long period of time (an hour, by way of example), and expandable balloon 1016 could be deflated for a relatively short period of time (seconds, for example), to alleviate a high pressure or edema occurrence, and then expandable balloon 1016 could be re-inflated to again secure first catheter 1000 at a desired location within the patient. The type of patients for whom the device will be utilized in the acute application may fall into various categories, including, but not limited to, S-T segment Elevated Myocardial Infarction (STEMI) patients, cardiogenic shock patients, and high risk Percutaneous Coronary Intervention (PCI) patients (such as those undergoing PCI of the left main coronary artery). STEMI is the traditional "emergent" patient who presents with classic heart attack symptoms, and when diagnosed in a hospital emergency room for example, the patient would traditionally be immediately moved to a Cath Lab to receive PCI to open an occluded coronary artery and restore blood flow to the myocardium. These patients are hemodynamically unstable and need support for the left ventricle.

In such a use, for example, an exemplary system 100 of the present disclosure could be used to, for example: (i) provide cardiac support to a patient who does not have immediate access to the Cath Lab and PCI. These patients may present in rural or community hospitals that do not have Cath Labs. They will need some type of temporary support while being transferred to an appropriate facility. These patients might also present at a hospital with a Cath Lab, but the Cath Lab is either understaffed to treat the patient, or does not have an available room to treat. In these cases, the system 100 of the present disclosure operates as a bridge to provide support until definitive treatment (primary PCI) is available; and/or (ii) provide cardiac support before, during, and after primary PCI. Many patients enter the Cath Lab in an unstable condition, and the insertion of balloons and stents adds to hemodynamic instability. An exemplary system 100 can provide cardiac support and improve hemodynamics such that the physician can operate in a more stable/controlled environment. It is also believed that by reperfusing ischemic myocardium before/during/and after primary PCI, one may reduce the amount of myocardium that is damaged by the ischemic event. This is clinically referred to as a "reduction in infarct size." Initial animal studies (as referenced in further detail herein) have suggested that the use of SARP in support of STEMI patients could cause a reduction in infarct size, which would have a significant impact on the outcomes for the patient in both the near and long term. Reduction in infarct size would slow the progression of any subsequent heart failure and reduce long term hospitalization and costs for this group of patients.

Cardiogenic shock is marked by a significant lowering of blood pressure and cardiac output that if not reversed, will ultimately lead to multisystem organ failure and death. Cardiogenic shock patients have a mortality exceeding 60%. In many cases, cardiogenic shock patients are too unstable to undergo surgery or PCI. Pharmacologics are used to increase pressure and cardiac output. Intra Aortic Balloon Pumps (IABP) and other LVAD type products are also employed to improve hemodynamics in an attempt to reverse the downward cycle of cardiogenic shock patients Exemplary embodiments of systems 100 of the present disclosure could be used in much the same fashion. High Risk PCI is typically defined as patients who have disease of the left main coronary artery, are diabetic, have multivessel disease, are above 75 years of age, have a prior history of MI, have renal insufficiency, etc. These are very sick patients, who are considered at high risk of adverse events before, during, and after undergoing PCI. Mortality rates and Major Adverse Cardiac Event (MACE) rates are much higher in this patient population. IABP's are commonly used in this patient population. In this population, systems 100 of the present disclosure may be used to provide cardiac support for a high risk PCI patient who is, at the time of the procedure, found to be hemodynamically unstable. It is evident to the operator that cardiac support is and will be needed during the procedure, and an exemplary system 100 of the present disclosure would be deployed from the outset. The patient's hemodynamics improve and the operator feels more comfortable working in the coronary system. IABP use is common in these patients.

Systems 100 of the present disclosure may also be used in this high risk population when it is anticipated that cardiac support may be needed during the procedure. In this case, an exemplary system 100 is deployed prior to the case, in order to provide support when and if it is needed. The patient is hemodynamically stable at the outset, and remains so throughout. IABP's are currently used in this fashion. This is commonly referred to as prophylactic use of cardiac support.

Acute Applications:

In this setting, exemplary systems 100 of the present disclosure will be used for cardiac support and to protect myocardium for a period of time that will generally be less than 24 hours. The clinical condition that precipitated the need for SARP will have typically been resolved in that 24 hour period, and the system 100 would be removed. However, use of systems 100 of the present disclosure are not limited to a 24 hour period, as in some cases, IABPs and other short term cardiac support devices are left in for periods exceeding 24 hours. Typically, the longest period of time that a short term device might be left in place is 4-6 days, at which point the clinician would begin to consider longer term implanted Left Ventricular Assist Devices (LVADs), which can support a patient for an extended period of time (weeks), and are often used as a bridge to heart transplant.

Clinical conditions that would require the acute application of an exemplary system 100 of the present disclosure include, but are not limited to: (i) Emergent treatment of STEMI and/or other Acute Myocardial Infarction (AMI) patients; (ii) Cardiogenic shock; (iii) High Risk PCI; (iv) Failed or aborted PCI where severe hemodynamic instability presents after initiation of the procedure. These patients are often transferred to immediate cardiac surgery, and require cardiac support while waiting for the surgical intervention; and/or (v) Weaning from a cardiopulmonary bypass machine in cardiac surgery. Some cardiac surgery patients have difficulty returning to normal cardiac condition when the cardiopulmonary bypass machine is turned off and the heart is restarted after successful revascularization in cardiac surgery. Exemplary systems 100 of the present disclosure could be used to support the heart until normal cardiac parameters return. Insertion could occur in the surgical suite, and the device would be left in place while the patient was transferred to a Cardiac Critical Care Unit (CCU). These exemplary clinical conditions cover the majority of potential applications for an acute embodiment of a system 100 of the present disclosure. Currently, more than 95% of all IABP and other short term support devices are used for these applications. In such applications, the goal of using an exemplary system 100 of the present disclosure is to deliver arterial (oxygenated) blood to the myocardium, in a retrograde manner using the venous system, in order to create hemodynamic stability for the patient and to protect and preserve myocardial tissue until the clinical event resolves or primary intervention (PCI or CABG) and revascularization can occur.

Chronic Applications:

In this setting it is intended that an exemplary embodiment of a system 100 of the present disclosure be implanted for 2 weeks or longer, for example, noting that ultimate implantation may be somewhat shorter in duration. Initial animal studies suggest that within 2 weeks, arterialization of the venous system is achieved, such that the venous system can become the conduit for a constant flow of arterial blood at arterial pressure. A clinical condition where the chronic application of a system 100 would be utilized is often referred to as "no option" patients, that is, patients for which there are no options available through which their clinical condition can be resolved. More specifically, these are patients with diffuse coronary artery disease (CAD) or refractory angina, where PCI and/or Coronary Artery Bypass Graft Surgery (CABG) is not an option. Patients that are diabetic, or have other co-morbidities, and are not candidates for interventions, would be candidates for a chronic application of a system 100 of the present disclosure. As previously referenced herein, the chronic application will generally require 10-14 days of retroperfusion in order to allow arterialization of the venous system. In certain instances, retroperfusion could be required for a longer period (such as 2-3 weeks, for example), or a lesser period, such as less than 10 days, for example. These patients, dependent upon their complete clinical situation, may be hospitalized for that period, or they may reside outside of the hospital. When residing outside of the hospital, the device utilized may be a catheter 10 embodiment with a branched implantable portion, such as shown in FIG. 1, for example. The catheter 10, including method of pressure regulation, would be implanted in the patient.

For those chronic patients, who must remain in the hospital for one of the aforementioned time periods, an acute embodiment of a system 100, for example, may be applicable. In such an embodiment, for example, system 100 may be percutaneously inserted and utilized during that time frame. Once arterialization occurs, a more permanent conduit may be constructed percutaneously or surgically to provide the permanent arterial blood source. When using an exemplary system 100 of the present disclosure, standard guide catheters can be used by the clinician to locate the coronary sinus and/or the great cardiac vein, for example. An 0.035" guidewire can be inserted to further establish access to the coronary sinus or the great cardiac vein. An exemplary system 100 can then be inserted over the 0.035" guidewire and advanced to the coronary sinus or the great cardiac vein, for example, via one of the ports as referenced herein. The distal end 1004 of the first catheter 1000 is intended to be located at the left main vein. The operator may advance the tip (distal end 1014) of first catheter 1000 to other vein sites dependent on clinical need. A balloon 1016, which in at least one embodiment may be located approximately 2 cm back from the distal end 1004, would then be inflated to secure the position of first catheter 1000 within the coronary sinus or the great cardiac vein, for example, allowing for the distal end 1004 of first catheter 1000 to locate at the left main vein. The inflated balloon 1016 will also work to ensure that arterial blood will flow in the retrograde fashion. Once the distal balloon 1016 is inflated, the 0.035" guidewire can be exchanged for an 0.014" pressure measurement wire, which will be used to measure the pressure at the distal end 1004 of first catheter 1000, to ensure that the portions of system 100 are not over pressurizing the vein, and to tell the operator how much pressure change will be required from the external pressure regulator. The proximal end of the pressure wire will be connected to its appropriate monitor.

When the catheter is located in the coronary sinus or the great cardiac vein, for example, the operator can now make the external (outside the body) connection to the arterial blood supply 1044. This is typically, but not limited to, the femoral or radial arteries. The physician will have previously inserted a standard procedural sheath into the arterial source in order to gain access to the source. This arterial sheath can also be used to provide access for catheters, guidewires, balloons, stents, or other devices that might be utilized while treating the patient. That arterial sheath will have a connector which can connect to the arterial supply cannula (with regulator) on the acute device (an embodiment of system 100). Once the connection is established and flow commences, the pressure wire will indicate the distal pressure measurement and the regulator can be adjusted to the proper setting (not to exceed 60 mmhg, for example). Monitoring of the distal pressure will be on-going throughout the period of time that the device is in-vivo. The regulator allows the operator to provide the correct distal pressures and to adjust those pressures, dependent on changes in the patient's pressure. With the pressure set and monitored, the patient is now receiving oxygenated blood to the myocardium in a retrograde fashion thru the coronary venous system. Such an operation (namely to retrogradly provide oxygenated blood) can be used to save a significant amount of ischemic tissue at the level of the border zone. In at least one embodiment, such a system 100 is used to perfuse the left anterior descending vein to supply oxygenated blood to the LAD artery occluded territory. Depending upon patient need and circumstance, the acute device (an embodiment of system 100) will be removed typically within the first 24 hours of insertion. The physician will make that determination. The insertion site will be closed per hospital protocol.

Validation of Methodology

As referenced in detail herein, coronary artery disease (CAD) is the number one cause of morbidity and mortality in the U.S. and worldwide. Even today, with percutaneous transluminal coronary angioplasty (PTCA) and coronary artery bypass grafting (CABG), optimal and timely treatment is still not available for all patients. Bridge therapies to complement existing gold standards of reperfusion therapy would be of significant value to a large number of patients. Because the coronary venous system rarely develops atherosclerosis, the use of the venous system for delivery of oxygenated blood has been well explored. Synchronized retrograde perfusion (SRP) and pressure-controlled intermittent coronary sinus occlusion (PICSO) are two retroperfusion methods for acute treatment of myocardial ischemia through the coronary venous system. PICSO and SRP have been used in conjunction with a balloon-tipped catheter positioned just beyond the orifice of the coronary sinus connected to a pneumatic pump, and either passively redirect coronary sinus blood (PICSO) or actively pump arterial blood during diastole (SRP) to the ischemic myocardium. These techniques have been shown to decrease ischemic changes, infarct size, myocardial hemorrhage, and no-reflow phenomenon, and improve left ventricular (LV) function when coronary blood flow is reinstituted after an acute occlusion. Wide application of these techniques, however, has been limited by concerns over their safety and complexity, and in particular, the need for repeated occlusion of the coronary sinus with a balloon. High pressure (SRP and PICSO) and flow (SRP) can cause damage to the coronary sinus with thrombosis and chronic myocardial edema.

We have validated in animal studies both the acute and chronic application of the methodologies referenced herein. In a recent acute study, we showed that preservation of the contractile function of the ischemic myocardium can be accomplished with selective autoretroperfusion (SARP) without the use of an external pump during acute LAD artery ligation. The hypothesis that SARP can preserve myocardial function at regulated pressures without hemorrhage of vessels or damage of myocytes was verified. In connection with this animal work, a bolus of Heparin was given before instrumentation and was then supplemented as needed to keep an activated clotting time (ACT) over 200 seconds. The right femoral artery was cannulated with a 7 Fr catheter and connected to a pressure transducer (TSD104A—Biopac Systems, Inc) for monitoring of arterial pressure. Before the sternotomy, the right carotid artery was cannulated with a 10 Fr polyethylene catheter through a ventrolateral incision on the neck to reach the brachiocephalic artery to supply the LAD vein during retroperfusion. The catheter had a roller clamp that was used to control the arterial pressure transmitted to the LAD vein. The right jugular vein was cannulated with an 8 Fr catheter for administration of drugs and fluids. Lidocaine hydrochloride was infused at a rate of 60 µg/kg/min before opening the chest and during the rest of the procedure. Magnesium sulfate (10 mg/min IV) along with lidocain was also used to treat extrasystole in the case of the control group. A vasopressor (Levophed®, Norepinephrine Bitartrate Injection, Minneapolis, Minn., 2-6 µg/min IV) was used during the procedure, and was adjusted accordingly to maintain a constant arterial blood pressure (70.0±8.9 mmHg, mean) in both the experimental and the control groups. Finally, heparin and nitroglycerine were diluted in 60 mL of 0.9% sodium chloride and infused using a syringe pump at a rate of 1 ml/min. The chest was opened through a midsternal thoracotomy, and an incision was made in the pericardium with the creation of a sling to support the heart with pericardial stay sutures.

Figure 18:
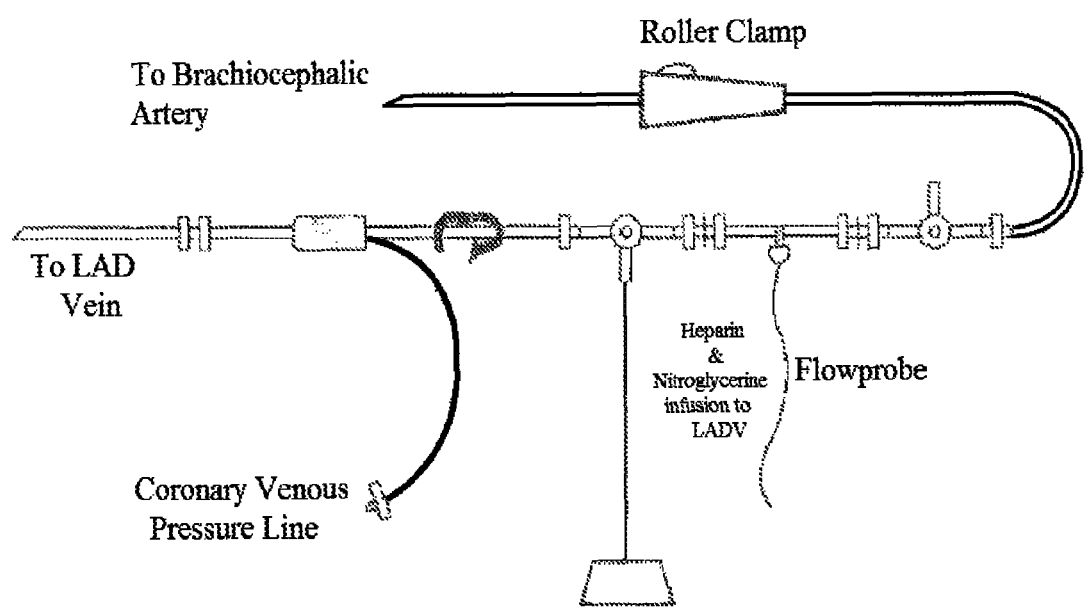
FIG. 18 shows a schematic of the retroperfusion system showing the arterial and retroperfusion catheters, according to a study in connection with the present disclosure.

A pair of piezoelectric ultrasonic crystals (2 mm in diameter on 34 gauge copper wire—Sonometrics Corporation) were implanted through small stab incisions in the anterior wall of the LV (area at risk) distal to the planned site (below first diagonal branch in the SARP group, and second diagonal branch in the control group) of LAD artery ligation, for assessment of regional myocardial function through measurement of midwall segment length changes. An additional pair of crystals was also implanted in the anterior wall of the LV within the normal perfusion bed (control area) of the proximal portion of the LAD artery. FIG. 18 shows a schematic of the retroperfusion system showing the arterial and retroperfusion catheters. Each pair of crystals were positioned in the midmyocardium (about 7 mm from the epicardium) approximately 10-15 mm apart and oriented parallel to the minor axis of the heart. The acoustical signal of the crystals was verified by an oscilloscope. In the SARP group (ligation+retroperfusion) the LAD artery was dissected free from the surrounding tissue distal to the first diagonal branch for subsequent ligation. A 2.5 mm flow probe was placed around the LAD artery and connected to a flow meter (T403—Transonic Systems, Inc). The LAD vein was also dissected close to the junction with the great cardiac vein, and the proximal portion ligated with 2-0 silk suture in order to prevent runoff to the coronary sinus. The LAD vein was then cannulated below the ligation with a 10 Fr cannula that was attached to the brachiocephalic catheter through one of two four-way stopcocks. A flow probe was placed between the stopcocks for measurement of coronary venous flow. Venous pressure was recorded through the pressure monitoring line from the retroperfusion cannula (as shown in FIG. 18). Retroperfusion was initiated immediately after ligation of the LAD artery and was maintained for a period of 3 hours. Arterial blood samples were taken at baseline and at the end of the first, second and third hours of ligation+retroperfusion for monitoring of pH, hematocrit, electrolytes, activated clotting time, and cardiac troponin I. Coronary venous SARP may be an effective method of protecting the myocardium during acute ischemia before definitive treatment is established as referenced herein regarding various catheter 10 and system 100 embodiments of the present disclosure. SARP may not only offer protection to the ischemic myocardium through retrograde perfusion of oxygenated blood but may also serve as a route for administration of thrombolytics, antiarrhythmics, and cell and gene therapy to the jeopardized myocardium before PTCA or CABG can be implemented in patients eligible for these procedures.

In addition to the foregoing, various devices and systems of the present disclosure can be used to perform methods for retroperfusion of various bodily organs to treat many different types of conditions. As referenced above, providing blood from one bodily vessel to another bodily vessel can be performed using devices and systems of the present disclosure, but in accordance with the following, said devices and systems can also be used to perform the following novel methods and procedures.

As generally referenced above, the concept of using veins to deliver oxygenated nutrient-filled blood (arterial blood) is predicated on the fact that despite any extent of the coronary arterial disease, the corresponding venous counterpart is atherosclerosis-free. An additional fact is that the upper body arterial system has much less predilection for atherosclerosis than the lower body. As such, the present disclosure identifies that the upper body can generally serve as the source of arterial blood to the venous systems of organs with arterial disease, and that devices and systems of the present disclosure can also be used in that regard. An additional characteristic of the venous system necessary to facilitate SARP (as referenced herein) is the existence of a redundancy of the venous system (namely multiple veins per artery as well as interconnections between venous vessels) to ensure proper venous drainage when portion of the system is used for SARP.

In view of the foregoing, a number of embodiments for retroperfusion of various organs or bodily regions that identify arterial blood donor and organ (venous system) are identified with the present disclosure, including, but not limited to, the following:

(i). Peripheral vessels. Embodiments of devices and systems of the present disclosure can be used to provide oxygenated blood from the femoral artery, the internal femoral artery, or the iliac artery, for example, to the distal saphenous vein or to deep muscle veins for arterialization in diabetic patients (a diffuse disease) to treat, for example a leg pre-amputation or a necrotic or gangrenous foot ulcer. This venous system has valves (typically larger than 1-1.5 mm in diameter) which can be overcome (inverted) through catheterization (namely the insertion of guidewire and SARP catheter, with guidewire dimensions down to 0.35 mm for 0.014" standard guidewire) to facilitate said peripheral vessel treatment.

(ii). Kidney-Renal Vein. Embodiments of devices and systems of the present disclosure can also be used to facilitate arterialization of the renal vein, which can be partial (polar vein) or total (left or right main veins) by way of the femoral or iliac arteries (if disease free), or from the axillary, brachial, or subclavian arteries of the upper body, if desired. Said procedure could be performed to, for example, treat acute or chronic renal ischemia due to diffuse atherosclerosis, severe intima hyperplasia, and to treat the kidney in connection with various collagen-vascular diseases.

(iii). Intestine (Bowel). A number of arterial sources, such as the femoral, iliac, axiallary, brachial, subclavian, or epigastric arteries, can be used with devices and systems of the present disclosure to facilitate regional arterialization following vein anastomosis (at the vein arch) to treat mesenteric arterial ischemia. In at least one embodiment, said arterialization is performed to treat an acute embolic or thrombotic mesenteric artery occlusion in patients with a severe bowel ischemia.

(iv). Spine. The first of the two main divisions of the spinal system, namely the intracranial veins, includes the cortical veins, the dural sinuses, the cavernous sinuses, and the ophthalmic veins. The second main division, namely the vertebral venous system (VVS), includes the vertebral venous plexuses which course along the entire length of the spine. The intracranial veins richly anastomose with the VVS in the suboccipital region, and caudally, the cerebrospinal venous system (CSVS) freely communicates with the sacral and pelvic veins and the prostatic venous plexus. The CSVS constitutes a unique, large-capacity, valve-less venous network in which flow is bidirectional. The CSVS plays important roles in the regulation of intracranial pressure with changes in posture, and in venous outflow from the brain. In addition, the CSVS provides a direct vascular route for the spread of a tumor, an infection, or an emboli among its different components in either direction. Various embodiments of devices and systems of the present disclosure can be used to provide oxygenated blood from the external carotid artery, the brachial artery, or the axiallary artery, directly to the jugular vein to treat any number of potential spinal injuries or conditions, including spinal cord ischemia.

(v). Penis. Various embodiments of devices and systems of the present disclosure can also be used to provide arterial blood from the epigastric artery to the penile dorsal vein to the cavernous system of the penis to treat erectile dysfunction.

Figure 19:
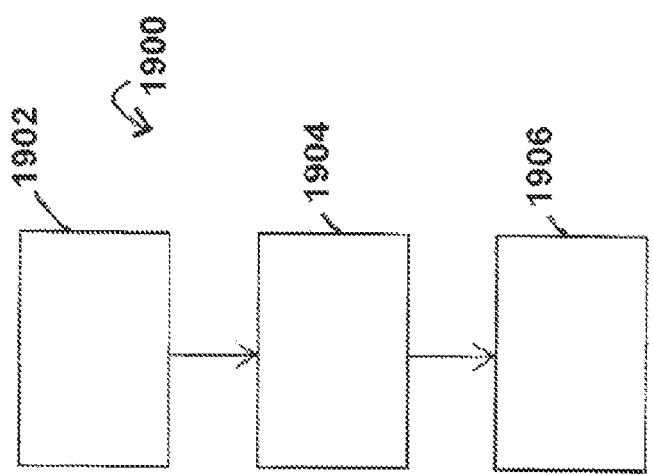
FIG. 19 shows a diagram of steps of an exemplary method of organ perfusion, according to at least one embodiment of the present disclosure.

The foregoing examples of organ-specific perfusion protocols are not intended to be exhaustive, but merely exemplary of various novel uses of perfusion devices and systems of the present disclosure. Accordingly, the present disclosure includes various methods for treating organ-related diseases, various methods of providing arterial (oxygenated) blood to veins at or near various organs, and various methods of potentially arterializing veins at or near various bodily organs using devices and systems of the present disclosure. For example, and as shown in FIG. 19, an exemplary method of organ perfusion of the present disclosure is provided. Method 1900, in at least one embodiment, comprises the steps of positioning at least a portion of a device into a patient's artery (an exemplary artery positioning step 1902), positioning at least a portion of the same or a different device into a patient's vein at or near a target organ (an exemplary vein positioning step 1904), and facilitating operation of the positioned portions to allow blood to flow from the artery to the vein to treat a condition or disease of the target organ (an exemplary operation step 1906). By way of example, an exemplary artery positioning step 1902 could be performed by positioning at least part of a first catheter 10 having a cannula 16 within an artery of a patient, the first catheter 10 configured to permit arterial blood to flow therethrough and further configured to permit a portion of the arterial blood to flow through the cannula 16, and an exemplary vein positioning step 1904 could be performed by positioning at least part of a second catheter 150 within a vein of the patient at or near a target organ, the second catheter 150 configured to receive some or all of the portion of the arterial blood. In such an embodiment, which may be referred to as a chronic treatment using catheter 10 and catheter 150, an exemplary operation step 1906 involves connecting the cannula 16 of the first catheter 10 to a portion of the second catheter 150 so that some or all of the portion of the arterial blood flowing through the cannula 16 is provided into the vein to treat a condition or disease of the target organ. Further, and by way of another example, an exemplary artery positioning step 1902 could be performed by positioning at least a portion of an arterial tube 1032 of a perfusion system 100 within an artery of a patient, the arterial tube 1032 configured to permit arterial blood to flow therethrough, and an exemplary vein positioning step 1904 could be performed by positioning at least a portion of a first catheter 1000 of the perfusion system 100 into a vein of the patient at or near a target organ, the first catheter 1000 configured to receive some or all of the arterial blood from the arterial tube 1032. In such an embodiment, which may be referred to as an acute treatment using system 100 of the present disclosure, an exemplary operation step 1906 involves operating a first flow regulator 1036 of the perfusion system 100 so that some or all of the arterial blood flowing through the arterial tube 1032 is provided into the vein to treat a condition or disease of the target organ.

In addition to the foregoing, and in various embodiments of devices (such as catheters 10 and/or cannulas 16), systems 100, and/or SSA systems 300, for example, of the present disclosure, such catheters 10, cannulas 16, and/or systems 100 may optionally comprise a regional hypothermia system 4000 configured in accordance with the following. Various regional hypothermia systems 4000 of the present disclosure, as shown in component block diagram of FIG. 20 and as referenced in further detail herein, are configured for use to cool (reduce the temperature of) blood and/or other fluids within the body for targeted delivery to a location within the body. Such cooling can be from, for example, at or about 0.5° C. to as much as 10° C. cooler, for example, than the native temperature of blood within the mammalian body. In some embodiments, localized blood cooling of greater than 10° C. may be desired and accomplished using one or more regional hypothermia systems 4000 of the present disclosure. In various embodiments, regional hypothermia systems 4000 are configured for use within a mammalian body even at tissues that are relatively difficult to reach due to, for example, potential occlusion of one or more coronary and/or cerebral arteries. Such regional hypothermia systems 4000 of the present disclosure may be useful in connection with the reduction of perfusion injuries by cooling the region of risk, whether it be at, near, or in the heart and/or brain, may be critical to reduce reperfusion injury and to decrease infarct size, for example, prior to opening an artery in the heart or brain. Retroperfusion, as referenced generally herein, provides an ideal mechanism to deliver blood at a target location, and the use of a regional hypothermia system 4000 of the present disclosure in connection with one or more catheters 10, cannulas 16, systems 100, and/or SSA systems 300 of the present disclosure can effectively deliver blood at a desired/targeted temperature by way of delivery through open veins, for example, to the region at risk, such as a heart or brain. In general, such catheters 10, cannulas 16, systems 100, and/or SSA systems 300, in connection with the use of one or more regional hypothermia systems 4000 of the present disclosure, can allow perfusion/retroperfusion of oxygenated blood, control blood perfusion pressure within a vessel, condition a blood vessel to operate under higher blood pressure (such as arterialization of a vein), increase flow of oxygenated blood to ischemic myocardium, and/or decrease the acute ischemic area during a myocardial infarct event, all at a relatively colder temperature than would otherwise be allowed without the use of a regional hypothermia system.

Figure 20:
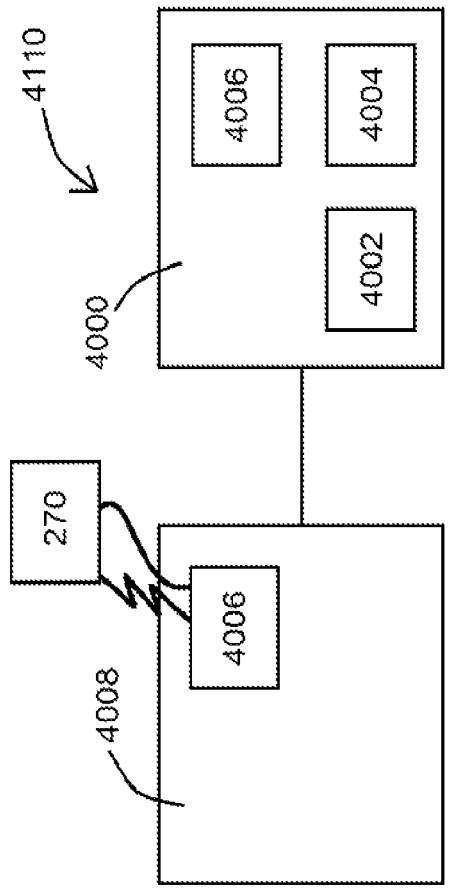
FIG. 20 shows a block diagram of a regional hypothermia system and kit used in connection with an exemplary device or system of the present disclosure.

In at least one embodiment of a regional hypothermia system 4000 of the present disclosure, and as shown in FIG. 20, regional hypothermia system 4000 comprises a heat exchanger 4002 coupled to one or more components of catheters 10, cannulas 16, systems 100, and/or SSA systems 300 of the present disclosure, such as, for example, catheter 10, cannula 16, second catheter 150, connector 170, first graft 185, second graft 190, Y connector 320, third catheter 350, first catheter 1000, arterial blood tube 1032, coupler catheter 1042, and/or other components referenced herein. Heat exchanger 4002, in various embodiments, is configured to reduce the temperature of blood passing through one or more components of catheters 10, cannulas 16, systems 100, and/or SSA systems 300, so that the blood that is ultimately delivered to the targeted area of interest, such as being at, near, or in the heart and/or brain, is at a lower temperature than normal (or without the use of a regional hypothermia system 4000). For example, and in at least one embodiment, regional hypothermia system 4000 is used to reduce the temperature of blood delivered at, near, or in the heart and/or brain by or about 3° C. to 4° C. via the general blood circuit created using various catheters 10, cannulas 16, systems 100, and/or SSA systems 300. Heat exchanger 4002, as referenced herein, can utilize one or more cooling products 4004, such as perfluorocarbon, liquid carbon dioxide, helium, another cooled gas, and/or another refrigerant or refrigeration mechanism known in the art, that facilitates the cooling of blood, and ultimately tissues at or near the cooled blood, through components of catheters 10, cannulas 16, systems 100, and/or SSA systems 300 of the present disclosure. Furthermore, one or more temperature sensors 4006 can be coupled to various components of catheters 10, cannulas 16, systems 100, and/or SSA systems 300 of the present disclosure, catheter 10, cannula 16, second catheter 150, connector 170, first graft 185, second graft 190, Y connector 320, third catheter 350, first catheter 1000, arterial blood tube 1032, coupler catheter 1042, and/or other components referenced herein, so that blood and/or tissue temperature(s) (including temperatures at, near, or in the heart and/or brain, depending on the type of catheters 10, cannulas 16, systems 100, and/or SSA systems 300 used) can be detected by temperature sensors 4006 and transmitted (via wire or wirelessly) to a remote module 270 and/or another data acquisition and processing system/mechanism so that a user of regional hypothermia system 4000 can regulate localized temperature (at, near, or in the heart or brain, for example), as desired. A generic device 4008 is shown in FIG. 20 as being operably coupled to an exemplary regional hypothermia system 4000 of the present disclosure, whereby generic device 4008 may comprise one or more catheters 10, cannulas 16, systems 100, SSA systems 300, other devices and/or systems of the present disclosure, and/or individual components thereof. An exemplary kit 4010 of the present disclosure, as shown in the figures, comprises an exemplary regional hypothermia system 4000 operably coupled to an exemplary generic device 4008 of the present disclosure.

Further, and in various embodiments, heat exchanger 4004 can be at the level of an arterial-venous connector, a double-lumen catheter, and/or another component of one or more catheters 10, cannulas 16, systems 100, and/or SSA systems 300 of the present disclosure. For the heart, this can be particularly important for patients with a door-to-balloon time of greater than two hours, for patients with ST segment elevation myocardial infarction (STEMI) that are at high risk for reperfusion injury, and/or patients with hemodynamics instability. There are several advantages to using a regional hypothermia system 400 of the present disclosure, including but not limited to rapid percutaneous insertion and rapid cooling of the myocardial area before opening the culprit artery to avoid the cascade of inflammatory reactions responsible for reperfusion injury. As referenced generally above, various regional hypothermia systems 4000 of the present disclosure are configured and operable to introduce mild hypothermia to reduce cardiac infarct size and general severity of the same. Such systems 4000, in connection with various catheters 10, cannulas 16, systems 100, and/or SSA systems 300 of the present disclosure, can treat chronic and acute heart failure, as needed, and generally reduce the severity of an injury and/or reduce inflammation as referenced herein, by way of regionally reducing blood temperature.

The disclosure of the present application also relates to a potential goal of translating the efficacy of a currently invasive open surgery that requires destruction of vein valves and induces edema due to the transmission of arterial blood pressure to the veins to a mini-surgical/percutaneous procedure that is much less invasive, takes less time and does not require removal of valves and damps the pressure to the veins to reduce the edema. In lower extremities with total or near complete obstruction of arterial blood flow, the perfusion of the limb in a retrograde manner through the venous system with arterial blood using various devices of the present disclosure will provide adequate oxygen and nutrient supply/demand matching to salvage limb function. Accordingly, the present disclosure includes methods of using venous circulation as an alternative method of limb salvage to deliver arterial blood in a retrograde manner to the ischemic extremity through a novel retroperfusion devices that will transform a lengthy surgical procedure into a simpler surgical/percutaneous hybrid procedure. In the absence of substantial forward native arterial pressure in the capillaries, arterial blood fed into the venous system at higher pressure than the native venous pressure will stimulate the development of significant collateral network between the native arteries and newly arterialized veins to supply nutritive flow and adequate oxygenation to the ischemic tissue and thus salvage the limb (to avoid amputation).

Figure 21:
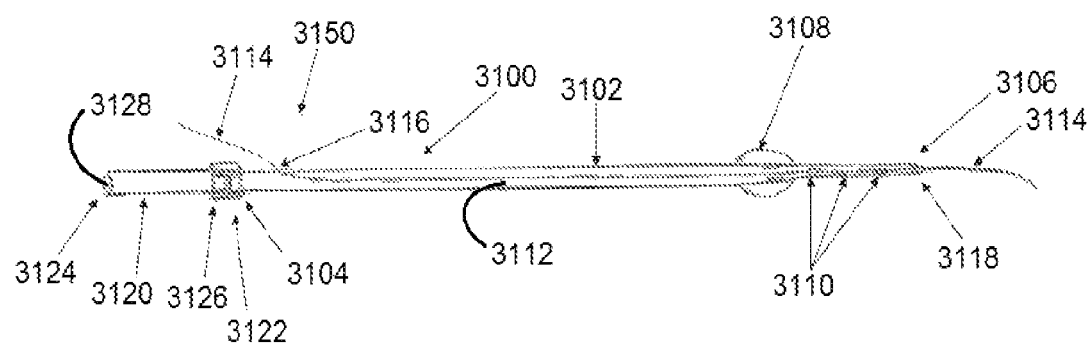
FIG. 21 shows an intravenous arterialization catheter, according to an exemplary embodiment of the present disclosure.

An exemplary catheter for facilitating intravenous arterialization of the present disclosure is shown in FIG. 21. Catheter 3100, as shown in FIG. 21, is configured as a hybrid endovascular catheter and comprises an elongated body 3102 having a proximal end 3104 and a distal end 3106. A balloon 3108 (which may be any number of inflatable members used in the catheter arts), in at least one embodiment, is positioned along elongated body 3102 and may be located closer to distal end 3106 than proximal end 3104. Balloon 3108, in various embodiments, may either be expandable (inflatable) as desired, using a gas and/or a liquid for example, or may be inflated automatically using a gas and/or a liquid, the latter referred to herein as being "auto-expandable." As shown in FIG. 21, exemplary catheters 3100 of the present disclosure have a plurality of apertures 3110 defined through elongated body 3102 at or near distal end 3106. Apertures 3110 are configured to allow fluid, such as oxygenated arterial blood, to flow from within a catheter lumen 3112 defined along a longitudinal length of elongated body 3102 out of apertures 3110 and into a luminal organ of interest, such as to an ischemic venous blood vessel. Apertures 3110, in certain other embodiments, may extend either an entire, substantial, or partial length of catheter 3110, and the number, concentration, and/or size of apertures 3110 can vary, as can the dimensions (such as internal diameter or cross-sectional area of catheter 3100) so to control the pressure by way of a pressure drop so that oxygenated arterial blood flowing through catheter 3100 and out of apertures 3110 is at a pressure or pressure range that the venous system can handle. Accordingly, various catheter 3100 features (such as length and diameter) can be tested to ensure proper pressure/flow relationships for the types of resistances that will be experienced in-vivo.

To facilitate proper guidance and positioning within a luminal organ of interest, various catheter 3100 embodiments of the present disclosure are configured to receive a guidewire 3114 therein (such as within lumen 3112 of catheter 3100), whereby guidewire 3114 could be positioned within catheter 3100 between a proximal opening 3116 (also referred to as a "lateral entrance") and a distal opening 3118 of catheter 3100 as shown in FIG. 21, for example. In addition, and in at least one embodiment of a catheter 3100 of the present disclosure, the proximal end 3104 of catheter 3100 is configured to attach to a graft 3120 (which may also be referred to herein as a "prosthesis"), with said connection by way of an optional connector 3122 (also referred to herein as a "quick connector") in some embodiments. In embodiments using one or more connectors 3122, proximal end 3104 of catheter 3100 may be configured with a "female" end or using a connector 3122 with a male or female end, and graft 3120 may be configured with a "male" end or using a connector 3122 with a male or female end. In other embodiments, opposing gender connections may appear on said components. As referenced herein, a general system 3150, as identified in FIG. 21, may comprise an exemplary catheter 3100 of the present disclosure and one or more additional elements, such as, for example, an exemplary graft 312, and exemplary guidewire 3114, and/or an exemplary dilator 3402, as shown in FIG. 24B and referenced in further detail herein.

Graft 3120, as shown in FIG. 21, can be used to effectively anastomose an artery of interest to a vein of interest. For example, and as shown in FIG. 23B, a proximal end 3124 of graft 3120 can be positioned within an artery 3220 (such as a femoral artery, as shown in FIG. 23B), and a distal end 3126 of graft 3120 can be positioned within a vein 3222 (such as a saphenous vein, also shown in FIG. 23B) so that oxygenated blood from artery 3220 can flow through a lumen 3128 of graft 3120 and into catheter 3100 coupled thereto, either directly or via the use of a connector 3122. Desired dimensions of graft 3120 would be such that the risk of lumen 3128 closing off (via thrombosis) would be reduced or eliminated. As shown in FIG. 3B, graft 3120 would be positioned within artery 3220 at a location proximal to an area of artery 3220 having diffuse disease (such as atherosclerotic plaques 3224 as shown in the figure), so that the user placing graft 3120 has a level of confidence that sufficient oxygenated arterial blood flow will exist at that location of artery 3220. If properly placed and connected, blood can flow from artery 3220, through graft 3120, into lumen 3112 of catheter 3100, and out of apertures 3110 so to introduce oxygenated blood to the peripheral/collateral veins 3206 at or near the distal end 3106 of catheter 3100 within vein 3222. In various embodiments of catheters 3100 of the present disclosure, shown in FIG. 21 or otherwise and/or as referenced herein, catheters 3100 may comprise one or more biologically compatible materials, such as polyurethane and/or other synthetic polymers. Grafts 3120 and/or catheters 3100 of the present disclosure may comprise the same or different materials, such as polytetrafluoroethylene ("PTFE"), polyethylene terephthalate (such as Dacron®, and/or other synthetic polymers. In addition, at least one embodiment of a catheter 3100 of the present disclosure is at least partially coated with an anticoagulant and/or an antithrombotic material, such as heparin, for example. An exemplary catheter 3100 and an exemplary graft 3120 of the present disclosure may couple to one another by way of their inherent coupling characteristics and/or using one or more connectors 3122 for anastomosis of graft 3120. The use of graft 3120 with catheter 3100, in at least one embodiment, allows for a controlled flow of oxygenated blood from an artery into a venous area of interest. Arterialization of a vein, as generally referenced herein, should preferably occur in a controlled or gradual fashion, as a rapid increase in blood flow and pressure to a vein can cause significant swelling, localized blood accumulation, and potential venous rupture. Graft 3120, in various embodiments, can be sutured to the artery and/or vein so to prevent unintended or undesired migration so to stabilize the same. Furthermore, the dimensions of graft 3120 (length, inner diameter or cross-sectional area, etc.) can be varied so to provide an initial controlled measure (flow or pressure) of blood therethrough upon implantation. By controlling the dimensions of graft 3120 and/or catheter 3100, as referenced above, side effects such as edema can be controlled/minimized by reducing the pressure of blood flowing into the vein or veins of interest Implantation of graft 3120, as referenced in further detail herein, can be performed percutaneously.

Figure 22:
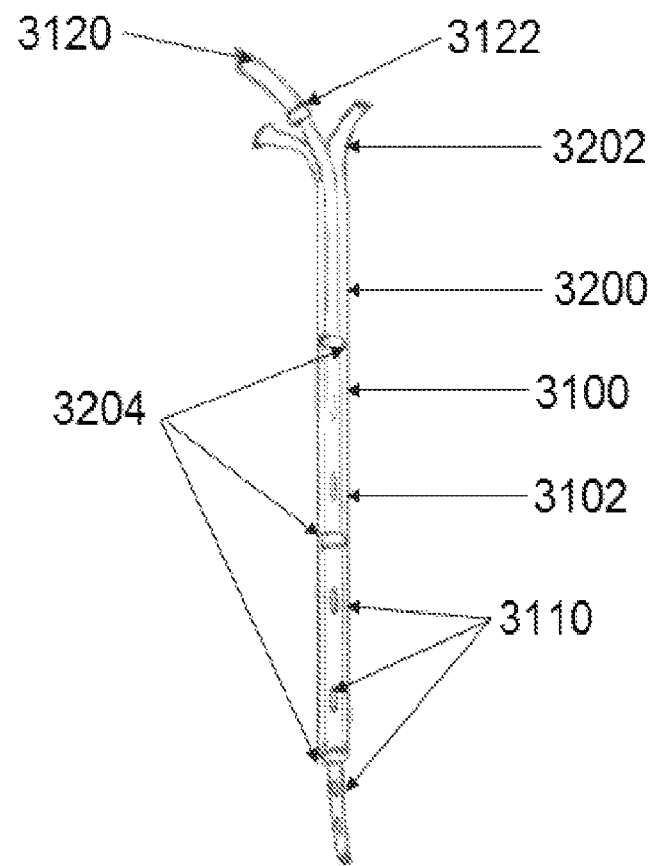
FIG. 22 shows a biodegradable intravenous arterialization catheter, according to an exemplary embodiment of the present disclosure.

An additional catheter 3100 embodiment of the present disclosure is shown in FIG. 2. As shown in FIG. 22, catheter 3100 is configured to fit within an external shaft 3200, with external shaft 3200 being split at its proximal end 3202. Catheter 3100, in such an embodiment, also defines a plurality of apertures 3110 within elongated body 3102 so that fluid can flow through a lumen 3112 of elongated body 3102 and out of apertures 3110. Exemplary catheters 3100 of the present disclosure, such as shown in FIG. 22, are partially or completely biodegradable and/or bioabsorbable. Various polymers, such as poly(lactic-co-glycolic acid) ("PLGA"), may be used within various catheter 3100 components, such as nodes 3204 shown in FIG. 22. Nodes 3204, as shown therein, would be located on the external wall of catheter 3100 (such as on elongated body 3102) for segmental occlusion at different levels of a luminal organ, such as the saphein vein. Exemplary nodes 3204 can resorb at different times, such as in one or more days, weeks, or months, and differing resorption rates can allow oxygenated blood to be introduced into other areas of the vein proximal to the initial introduction over time to facilitate gradual arterialization of the vein proximal to the initial introduction location. External shaft 3200, in various embodiments, is used/configured to cover apertures 3110, so that if it is desired to arterialize different locations within the vein, external shaft 3200 can be retracted so that additional apertures 3110 proximal to the originally exposed aperture(s) 3100 are exposed to irrigate oxygenated blood to the additional targeted vein area(s). External shaft 3200, in various embodiments, is used/configured to cover nodes 3204, whereby retraction of external shaft 3200 to expose nodes 3204 to blood flow would start/facilitate the process of resorption of nodes 3204. An exemplary biodegradable and/or bioabsorbable catheter 3100, such as shown in FIG. 22, may have additional features such as those shown in FIG. 21 or as otherwise shown or described herein, such as, for example, a connector 3122.

Figure 23A:
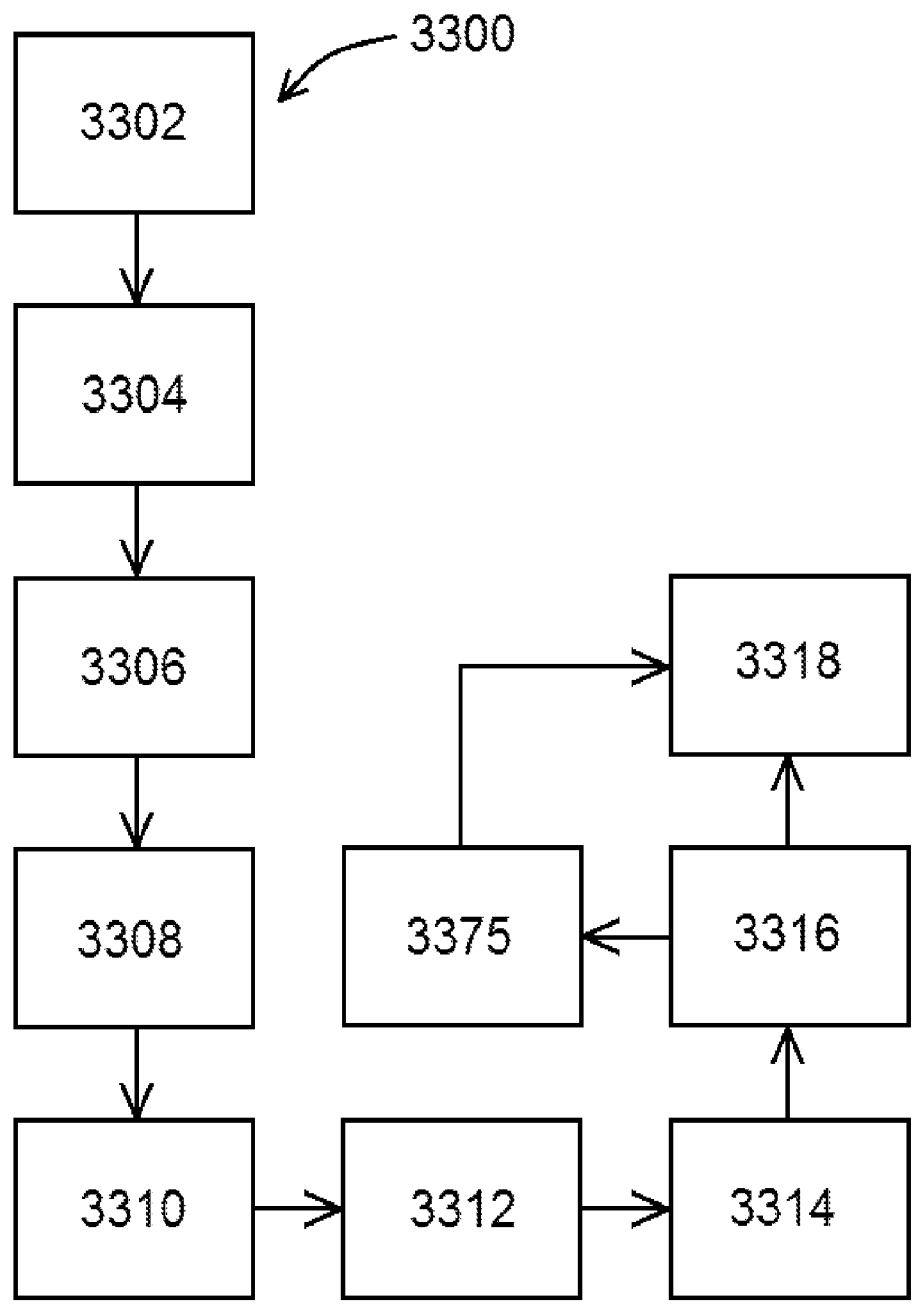
FIG. 23A shows steps of a method of using an intravenous arterialization catheter, according to an exemplary embodiment of the present disclosure.
Figure 23B:
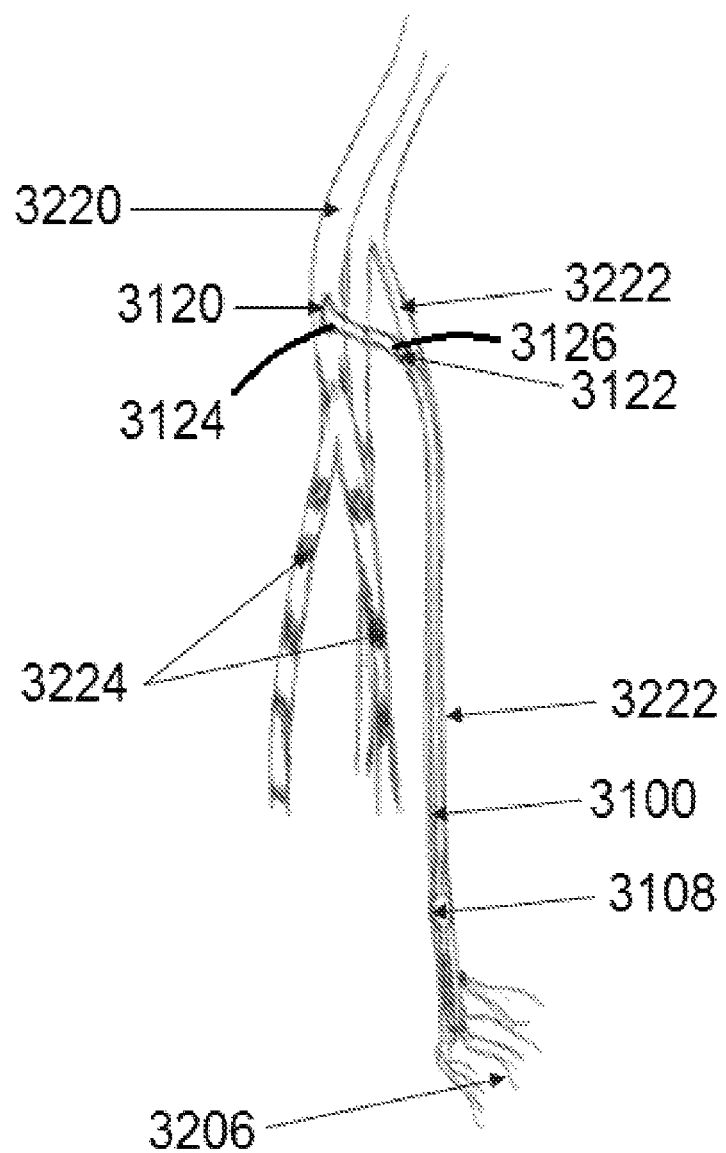
FIG. 23B shows an embodiment of a catheter positioned within a vein and connected to a graft in communication with an artery, according to an exemplary embodiment of the present disclosure.

Exemplary catheters 3100 of the present disclosure may be used in accordance with the following methods, as depicted in step format in FIG. 23A with mammalian body placement shown in FIG. 23B. In an exemplary method 3300 of the present disclosure, a small incision is made at the level of the peripheral artery source, such as the iliac, femoral, or popliteal artery (an exemplary arterial incision step 3302), and the proximal end 3124 of graft 3120 is positioned into the artery and the distal end 3126 of graft 3120 is positioned into the vein of interest, such as the saphenous vein, to anastomose the same (an exemplary graft anastomosis step 3304). Method 3300, in at least one embodiment, further comprises one or more of the steps of puncturing the vein of interest (such as the saphenous vein, for example) (an exemplary venous puncture step 3306), introducing at least part of a guidewire 3114 into the vein through the puncture aperture (an exemplary guidewire insertion step 3308), and the distal advancement (progression) of guidewire 3114 to a location at or near the portion of the vein of interest (such as, for example, the malleolus saphenous vein segment), while avoiding any venous valves along the way if possible (an exemplary guidewire advancement step 3310). Various methods 3300 of the present disclosure further comprise the steps of advancing (progressing) catheter 3100 over guidewire 3114 so that the distal end 3106 of guidewire 3100 is located within the vein at the region of interest (an exemplary catheter advancement step 3312), and connecting catheter 3100 (at, for example, the proximal end 3104 of catheter 3100) to the graft 3120 (at, for example, the distal end 3126 of graft 3120), either directly or using connector 3122, releasing the oxygenated arterial blood and allowing it to flow from the artery into lumen 3112 of catheter 3100 and out of apertures 3110 (an exemplary catheter-graft connection step 3314). Such a mini-surgical procedure, namely the performance of catheter-graft step 3314, will create a graft anastomosis with an artery, such as the femoral artery. This would complete the procedure to allow arterial oxygenated blood to flow from the artery to the vein via graft 3120 and catheter 3100 to various extremities, including the lower extremities. Steps 3310 and/or 3312, or other method 3300 steps of the present disclosure, may be performed using fluoroscopy, intravascular ultrasound ("IVUS"), a surface ultrasound, or other scanning methods so that the user of guidewire 3114 and/or catheter 3100 is aware of the locations of portions of said devices within the patient's vasculature. To avoid or reduce retrograde flow and/or to secure a portion of catheter 3100 within the vein of interest, an exemplary method 3300 of the present disclosure may further comprise the step of inflating balloon 3108 (by way of manually or automatically operating an inflation source operably coupled to balloon 3108) (an exemplary balloon inflation step 3316). Balloon 3108, which in at least one embodiment may be positioned approximately 1-2 cm from the distal end 3106 of catheter 3100, will be inflated to ensure selective retroperfusion of the region of interest (minimize edema) and to prevent antegrade flow of the blood once retroperfusion is established. Steps of methods 3300, as referenced above, may be performed in a different order than described above. For example, step 3304 may be performed after steps 3310 and 3312.

Over time, such as after two to four weeks for example after use of catheter 3100 within the patient, the venous vessels in the area at or distal to the distal end 3106 of catheter 3100 will arterialize, and over a period of approximately four to six weeks, the native arterial system will form collaterals with the newly arterialized venous vessels to revascularize the limb, such as the leg or portions thereof, such as the foot. After arterialization has been achieved, catheter 3100 can be removed from the patient (an exemplary catheter removal step 3318). However, and prior to catheter 3100 removal, catheter removal step 3318 may further comprise the additional step of connecting the vein to the artery so to provide oxygenated blood to the distal arterialized venous area. Such a step may also include the step of occluding the vein by way of a tying and/or clipping the proximal portion of the vein. In general, removal of catheter 3100 would discontinue the supply of oxygenated blood to the venous region of interest, and connecting the artery to the vein would allow oxygenated blood to continue to flow through the vein. The tying and/or clipping of the vein proximal to the region of interest, using a tie and/or a cutting tool, for example, would eliminate undesired retrograde blood flow through the vein. The above-referenced exemplary methods 3300, or other methods whereby some of all of an exemplary catheter 3100 of the present disclosure is positioned within a patient's vasculature, would allow the patient to resume or pursue certain mobility, such as walking and sitting if catheter 3100 is positioned within the patient's leg. In such embodiments, catheter 3100 may comprise malleable and non-collapsible biologically-compatible material(s) so to improve overall comfort. However, certain patient's either may not wish to have the majority or all of catheter 3100 positioned within their vasculature, or the treating physician/interventionalist may determine that using catheter 3100 in a different fashion, or a different catheter 3100 embodiment, may be preferred.

Accordingly, at least one additional method 3300 of the present disclosure is depicted in step format in FIG. 23C and described as follows. In at least one additional method 3300 of the present disclosure, method 3300 comprises the steps of implanting catheter 3300 within the patient through a subcutaneous tunnel 3400 parallel or substantially parallel to the length of the vein of interest (such as the saphenous vein), reaching the desired area of interest (such as the malleolus saphein vein segment) (an exemplary catheter implantation step 3350), and making an incision in the skin and isolating the distal end 3106 of catheter 3100 at the level of the malleolus saphein vein segment, for example (an exemplary skin incision step 3352). Step 3350 may be performed via skin puncture as well, using an optional guidewire 3114 and/or an optional dilator 3402, as shown in FIG. 24B if desired. Dilator 3402, in at least one embodiment, comprises an elongated body having a cross-section larger than a cross-section of catheter 3100, so that when dilator 3402 is advanced subcutaneously, catheter 3100 can be positioned within the subcutaneous tunnel created using dilator 3402. In at least another embodiment, and as shown in FIG. 24B, dilator comprises a dilator lumen 3404 defined therethrough along a longitudinal length of dilator 3402, terminating at or near one end with a distal dilator aperture 3406, whereby a guidewire 3114 can be positioned within dilator lumen 3404, and/or whereby device 3100 can be positioned within dilator lumen 3404. In view of the same, catheter implantation step 3350 may be performed in various manners. For example, catheter implantation step 3350 can be performed by creating a subcutaneous tunnel using dilator 3402, and advancing at least a portion of catheter 3100 within the subcutaneous tunnel. In another embodiment, catheter implantation step 3350 may be performed by introducing and subcutaneously advancing guidewire 3114 into the mammalian patient and advancing at least a portion of catheter 3100 over guidewire 3114. In yet an additional embodiment, catheter implantation step 3350 can be performed by introducing and subcutaneously advancing a guidewire into the mammalian patient, advancing a dilator over the guidewire to create a subcutaneous tunnel, and advancing at least a portion of the catheter within the dilator. In another embodiment, catheter implantation step 3350 can be performed by introducing and subcutaneously advancing a dilator having a dilator lumen defined therein and a guidewire positioned within the guidewire lumen into the mammalian patient to create a subcutaneous tunnel, removing the dilator, and advancing at least a portion of the catheter within over the guidewire. In yet another embodiment, catheter implantation step 3350 can be performed by introducing and subcutaneously advancing a dilator having a dilator lumen defined therein and a guidewire positioned within the guidewire lumen into the mammalian patient to create a subcutaneous tunnel, removing the dilator, and advancing at least a portion of the catheter within over the guidewire.

Exemplary methods 3300 may further comprise the steps of puncturing the vein of interest (such as the saphenous vein) via traditional venous puncture or incision so to form a venous entrance 3408 (an exemplary venous puncture step 3306), and introducing the distal end 3106 of catheter 3100 into the vein of interest (such as the distal malleolus saphenous vein segment) (an exemplary catheter introduction step 3354). Various methods 3300 further comprise the steps of implanting an exemplary graft 3120 (such as by performing arterial incision step 3302) so that the proximal end 3124 of graft 3120 is positioned into the artery and the distal end 3126 of graft 3120 is available to be connected to catheter 3100 at, for example, the proximal end 3104 of catheter 3100, and connecting catheter 3100 (at, for example, the proximal end 3104 of catheter 3100) to the graft 3120 (at, for example, the distal end 3126 of graft 3120), either directly or using connector 3122, releasing the oxygenated arterial blood and allowing it to flow from the artery into lumen 3112 of catheter 3100 and out of apertures 3110 (an exemplary catheter-graft connection step 3314). Over time, such as after two to four weeks for example, the venous vessels in the area at or distal to the distal end 3106 of catheter 3100 will become fully arterialized, and over a period of approximately four to six weeks, the native arterial system will form collaterals with the newly arterialized venous vessels to revascularize the limb, such as the leg. After arterialization has been achieved, catheter 3100, or remaining non-biodegradable portions thereof, can be removed from the patient (an exemplary catheter removal step 3318). If the entire catheter 3100 is biodegradable or bioresorbable, catheter removal step 3318 may not be required. The term "collaterals", as referenced herein, refers generally to the phenomenon that occurs during and after initial arterialization. Arteries and veins tend to run generally parallel to one another, with the veins forming a general drainage system that allows blood to flow back to the heart. By performing one or more methods 3300 as referenced herein, oxygenated blood flows to a vein, for which the increased blood pressure and increased overall blood nutrients facilitates arterializations. Arteries generally do not collateralize with veins, as veins generally have nothing to offer with respect to oxygenated blood or other blood nutrients. Arteries having oxygen-deficient or nutrient-deficient blood flowing therethrough will want to connect with arteries having oxygen and/or nutrient rich blood flowing therethrough, but that process is generally limited naturally as arteries would need to be adjacent to one another to facilitate the collateralization process. As arteries and veins overlap one another, various methods 3300 of the present disclosure effectively turn portions of veins into arteries, and the newly-formed arteries can then collateralize with other adjacent arteries and potentially adjacent veins. Various additional methods 3300 of the present disclosure may further comprise the step of moving catheter 3100 to another location within the vein of interest, or moving catheter 3100 to another vein of interest, so to facilitate arterialization of a second region within the patient's venous vasculature (an exemplary second region arterialization step 3375, such as shown in FIGS. 23A and 23C). For example, catheter-graft connection step 3314, as referenced above, may be performed at a first location, and, after a desired amount of time has elapsed, catheter 3100 can be moved to a second location within the patient's body, allowing for additional localized arterialization to take place via step 3375.

Figure 23C:
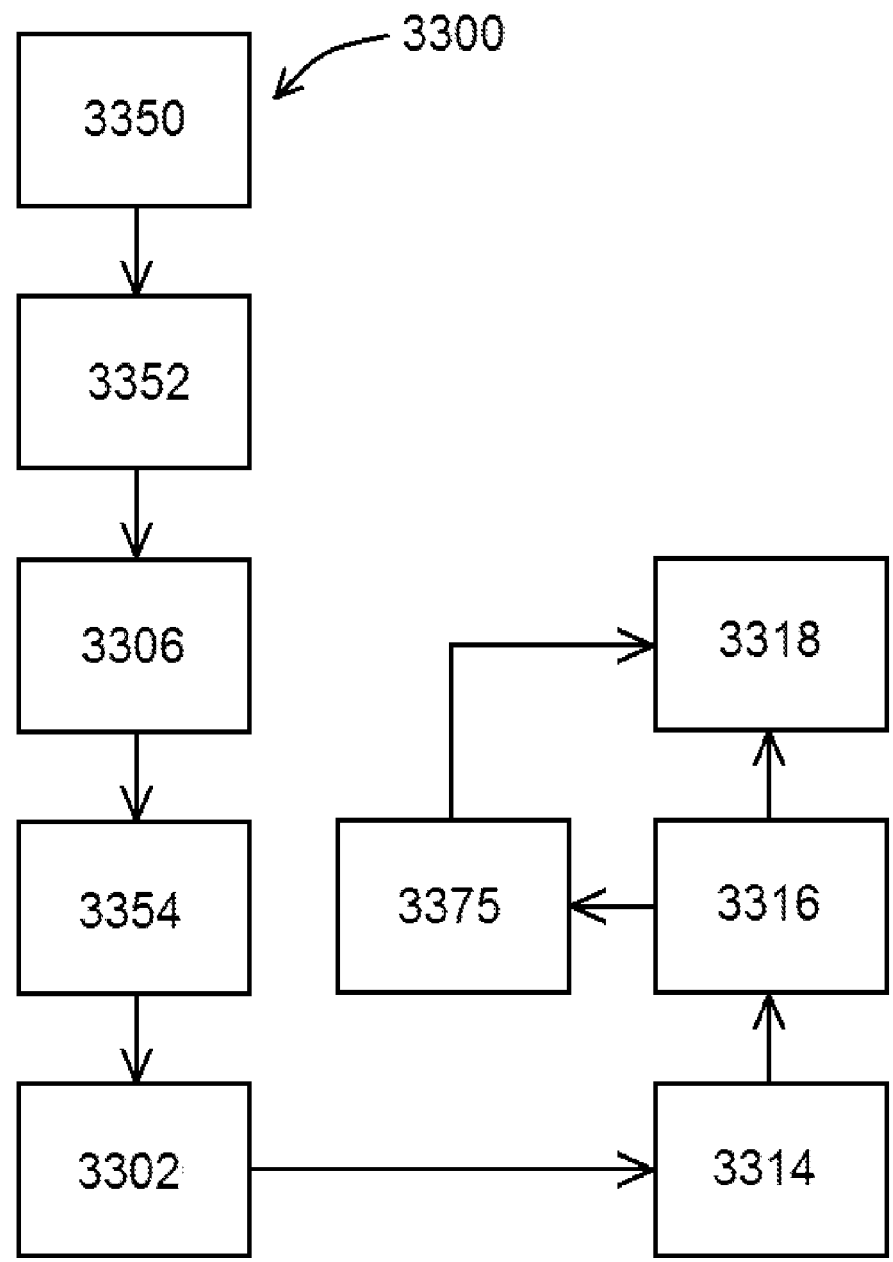
FIG. 23C shows steps of another method of using an intravenous arterialization catheter, according to an exemplary embodiment of the present disclosure.
Figure 26A:
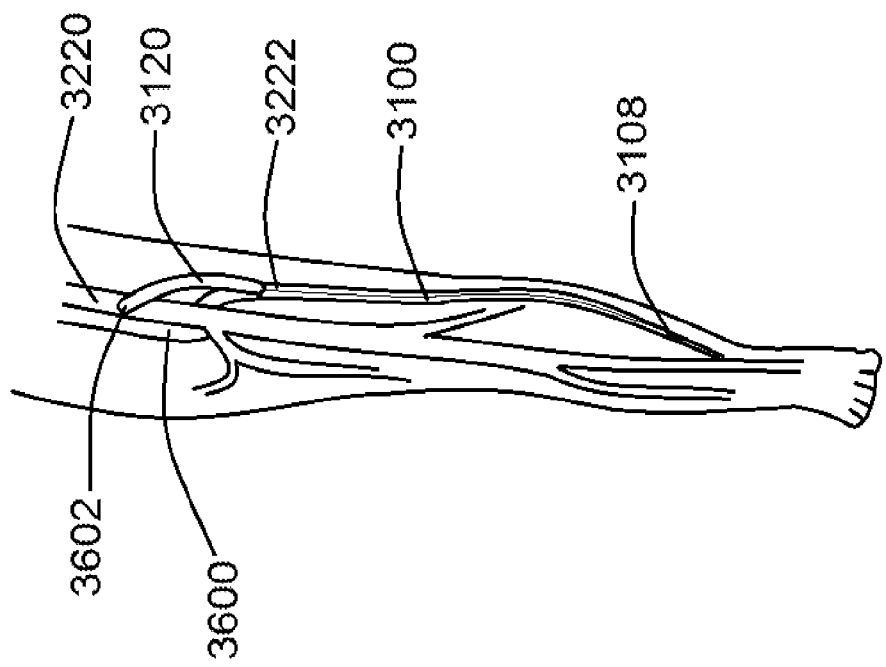
FIGS. 26A and 26B show embodiments of catheters positioned into a human and animal vein, respectively, according to exemplary embodiments of the present disclosure.
Figure 25:
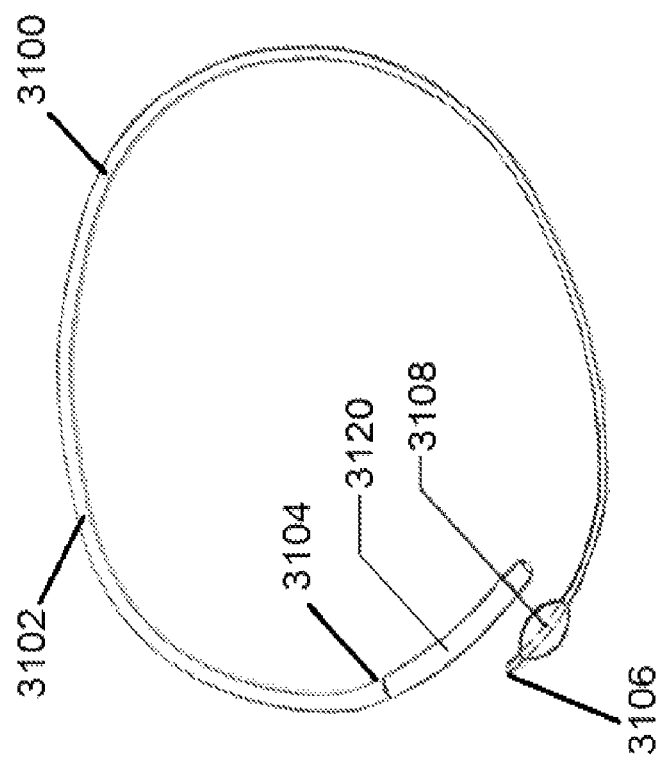
FIG. 25 shows an intravenous arterialization catheter, according to an exemplary embodiment of the present disclosure.
Figure 26B:
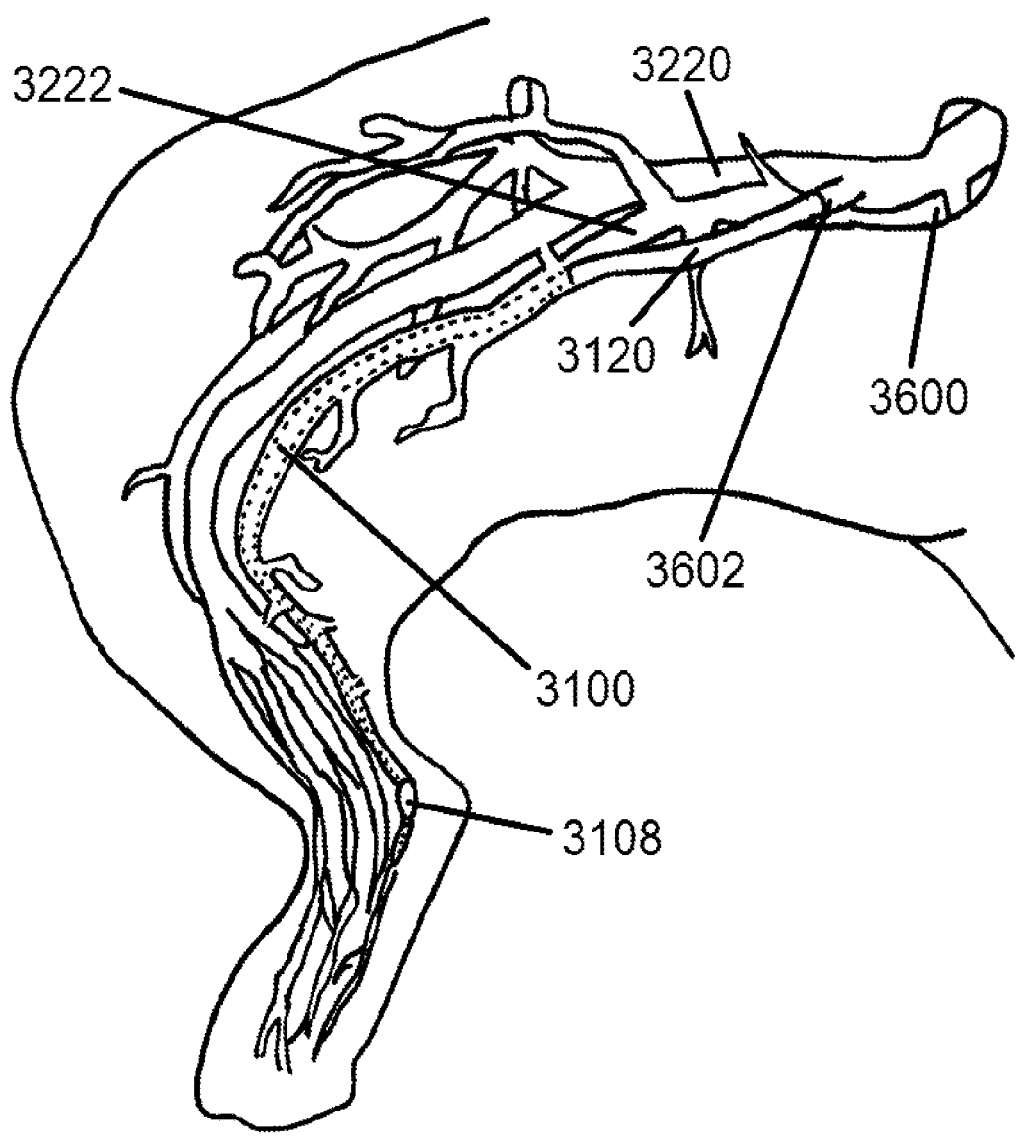

FIG. 24A shows selected components of an exemplary catheter 3100 of the present disclosure useful in connection with method 3300 as depicted in FIG. 23C and referenced above. As shown in FIG. 24A, exemplary catheter 3100 comprises an elongated body 3102, an autoexpandable balloon 3108 and a plurality of apertures 3110 at or near distal end 3106 of elongated body 3102, and a quick connector 3122 at proximal end 3104 of elongated body to connect graft 3120 to elongated body 3102 of catheter 3100. FIG. 24B shows placement of an exemplary catheter 3100 of the present disclosure in connection with one or more above-referenced methods 3300 whereby catheter 3100 is positioned subcutaneously through a subcutaneous tunnel 3400. As shown therein, the distal end 3106 of catheter 3100 is positioned through a venous entrance 3408 so that arterial (oxygenated) blood can flow through graft 3120, through lumen 3112 of catheter 3100, and out of apertures 3110 into vein 3222 so to arterialize peripheral/collateral veins 3206. FIG. 25 shows an exemplary catheter 3100 of the present disclosure with certain identified components. As shown therein, catheter 3100 comprises an elongated body 3102 having a proximal end 3104 and a distal end 3106, a balloon 3108 positioned at or near distal end 3106, and a graft 3120 coupled to catheter 3100 at or near proximal end 3104 of catheter 3100. FIGS. 26A and 26B show embodiments of catheters 3100 of the present disclosure positioned within a veins 3222 of a mammalian circulatory system. As shown therein (human leg in FIG. 26A, animal leg in FIG. 26B), catheter 3100 is positioned within the great saphenous vein (vein 3222), distal to the femoral vein 3600, while an anastomosis 3602 is present between graft 3120 and the femoral artery 3220. Balloon 3108 is shown in its inflated stated, potentially to anchor catheter 3100 within vein 3222 and to prevent retrograde flow of arterial blood through the great saphenous vein 3222 proximal to balloon 3108.

In addition, the use of a graft 3120 and a catheter 3100 of the present disclosure can not only control pressure and flow of blood therethrough to a vein of interest, catheter 3100 can be used in a way to preserve (not destroy) any valves present in the vein where catheter 3100 is implanted. For example, advancement of a guidewire 3114 through lumen 3112 of catheter 3100 and out of distal opening 3118, as shown in FIG. 21, can facilitate advancement of catheter 3100 within the vein of interest, allowing any valves passed by catheter 3100 to resume operation upon withdrawal or bioabsorption of catheter 3100. In addition to the foregoing, catheter 3100 and/or graft 3120 can be implanted percutaneously, which may be a preferred implantation method for high risk or otherwise compromised patient conditions. For example, graft 3120 can be inserted percutaneously by puncture of the targeted arterial site (identified using echodoppler, angiography, or another scanning method), and catheter 3100 can be inserted percutaneously into the vein (such as the saphein vein, identified using echodoppler, angiography, or another scanning method). Furthermore, connecting catheter 3100 and graft 3120 using a quick connector 3122 percutaneously can also facilitate the movement of catheter 3100 to a second location within the patient or removal out of the patient altogether. As generally referenced above, exemplary methods 3300 of the present disclosure, and potentially other uses of exemplary catheters 3100 of the present disclosure, have a number of advantages over current invasive surgical procedures. For example, certain traditional surgical procedures not only take several hours to perform, but also are invasive open surgeries where most, if not all, branches off of the vein of interest are ligated, and certain other surgeries actually remove the vein of interest itself, reverse it, and reconnect it, creating additional potential complications. Uses of catheters 3100 of the present disclosure are far less invasive, do not require complicated open surgical procedures, and can be used to treat inoperable lower limbs via gradual and selective retroperfusion/revascularization. Furthermore, and as referenced above, destruction of venous valves is avoided using catheters 3100 of the present disclosure, while certain surgical procedures either intentionally or intentionally destroy or reduce the functionality of said valves. In addition to the foregoing, various methods 3300 of the present disclosure may be used to direct blood to and arterialize other areas of the mammalian body, not just the peripheral venous system of a patient's leg or foot. For example, other areas of a patient, such as the patient's hands, arms, torso, and other areas, may be targeted as locations to receive arterialized blood using one or more catheters 3100 of the present disclosure.

The present disclosure also includes disclosure of various perfusion and/or retroperfusion devices and systems and methods of using the same, configured for use in connection with various coronary, peripheral, and other retroperfusion methods/procedures and/or to treat various ischemic conditions. Various devices and systems of the present disclosure are configured to facilitate blood flow in a retrograde direction, from a patient's artery to the patient's vein, so that a supply of oxygenated blood can reach parts of the patient's body that can benefit from that blood. Various devices and systems of the present disclosure can also be used to generally facilitate arterialization of a venous vessel over time at or by way of a gradual increase in pressure, so that the arterialized vessel can ultimately withstand full or substantially full blood pressures that otherwise exist within a patient's arterial system. Furthermore, various devices and systems of the present disclosure can be used to generally regulate blood pressures therethrough.

Figure 28:
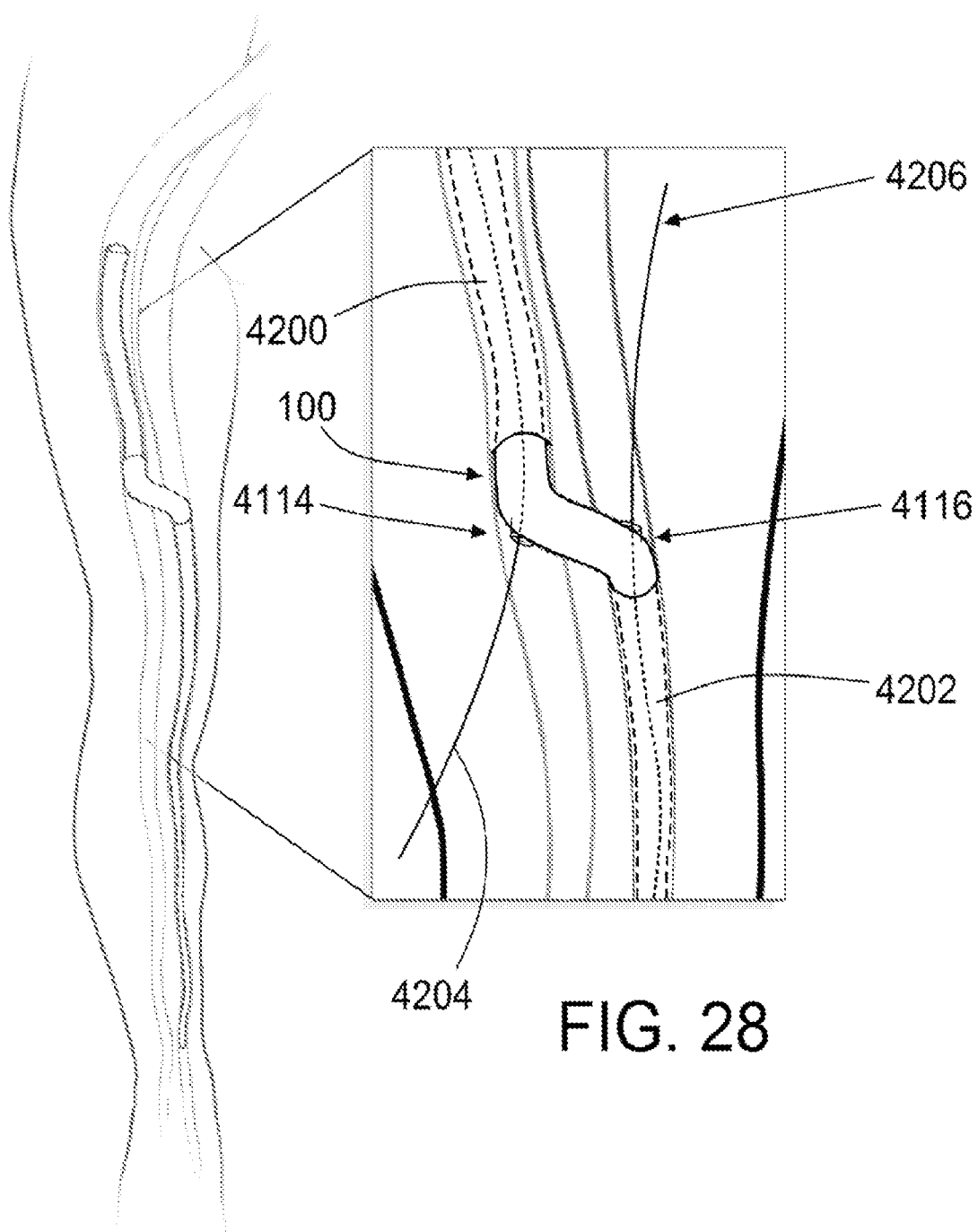
FIG. 28 shows a retroperfusion device positioned at least partially within a mammalian vasculature, according to an exemplary embodiment of the present disclosure.

An exemplary perfusion/retroperfusion device of the present disclosure is shown in FIG. 27A. As shown therein, device 100 comprises a unitary body 4100 having a wall 4102, a first portion 4104 terminating at a first end 4106 and configured for at least partial placement within a mammalian artery 4200 (as shown in FIG. 28), and a second portion 4108 terminating at a second end 4110 and configured for at least partial placement within a mammalian vein 4202 (also as shown in FIG. 28). As shown in FIG. 27A, device 100 has a lumen 4112 defined therethrough inside of wall 4102. Devices 100, as referenced herein, may also generally be referred to as "catheters" or "catheter devices" given that they have some sort of lumen defined therethrough. At least one advantage of unitary body 4100 over other retroperfusion devices 100 known in the art is that unitary body 4100 is a single continuous component, and does not comprises at least two components that must be coupled to one another. Such a unitary body 4100 therefore eliminates all risk of the two or more components becoming disconnected while in use. In at least one embodiment, and as shown in FIG. 27A, first portion 4104 of device 100 is relatively shorter than second portion 4108 of device 100. Phrased differently, and as shown in the figure, first portion 4104 has a first length ($L_1$), and second portion 4108 has a second length ($L_2$), whereby $L_1$ is less than $L_2$. For example, and in certain device 100 embodiments, $L_1$ can range from or about 5-10 cm, while $L_2$ can range from or about 50-70 cm. Other embodiments, such as devices 100 where $L_1$ is under 5 cm or over 10 cm, and/or where $L_2$ is under 50 cm or over 70 cm, are also within the scope of the present disclosure. Such a configuration is indicative of the potential need to deliver the source of oxygenated blood to a peripheral area of a patient, such as to the patient's feet, and access to a suitable artery 4200 may be significantly away from that ultimate delivery location. The ability to deliver oxygenated blood to a peripheral area of a patient, such as to a patient's foot, may ultimately facilitate being able to prevent potential foot amputation. As such, a relatively longer second portion 4108 would allow blood to travel within device 100 a relatively longer distance in the second portion 4108 as compared to the first portion 4104. As such a longer portion would not be required within the patient's artery 4200, first portion 4104 can be somewhat shorter than second portion 4108, and in at least certain device 100 embodiments, it may be desirable to have a shorter first portion 4104.

An exemplary device 100 of the present disclosure, as shown in FIG. 27A, has a first one-way valve 4114 and a second one-way valve 4116. A segment 4118 may exist between first one-way valve 4114 and second one-way valve 4116, or first one-way valve 4114 and second one-way valve 4116 may be sized and shaped to be immediately adjacent to one another. First one-way valve 4114 is sized and shaped to receive at least part of a first guidewire 4204 (as shown in FIG. 28) therethrough, and second one-way valve 4116 is sized and shaped to receive at least part of a second guidewire 4206 (also shown in FIG. 28) therethrough. As shown in FIG. 27A, first one-way valve 4114 may be positioned at or near an end of first portion 4104 opposite first end 4106, and second one-way valve 4116 may be positioned at or near an end of second portion 4108 opposite second end 4110. Various retroperfusion devices 100 of the present disclosure can be used in connection with various coronary, peripheral, and other retroperfusion methods and/or to treat various conditions as referenced in the various patent applications incorporated herein by reference. For example, at least part of first portion 4104 of device 100 could be positioned within a subclavian or axiallary artery (exemplary arteries 4200), and at least part of second portion 4108 of device 100 could be positioned within a subclavian or an axillary vein (exemplary veins 4202) for use and/or treatment at or near the heart (such as, for example, coronary retroperfusion). Peripheral uses, for example, may include positioning at least part of first portion 4104 of device within an iliac artery (an exemplary artery 4200) and positioning at least part of a second portion 4108 of device 100 within a saphenous vein (an exemplary vein 4202), as shown in FIG. 28, for example. Various arteries 4200, such as the femoral artery, the iliac artery, and in potentially more extreme instances/circumstances, the aorta itself, can be used as potential sources of oxygenated blood for retrograde delivery to a patient's venous system.

Furthermore, various devices 100 of the present disclosure have a flexible body 4100/wall 4102, which is able to deform easily without collapsing (so that lumen 4112 remains open to allow blood to flow from first end 4106, through body 4100, and out of second end 4110). The entire body 4100, or portions thereof, can be flexible. Such an embodiment of body 4102 may comprise a coil-reinforced wall, whereby one or more coils 4150, as shown in FIG. 27B, are used in connection with an impermeable coating 4152. Use of an exemplary device 100 of the present disclosure may include the following steps/tasks. An exemplary device 100 is shown in FIG. 28 positioned in part within an artery 4200 and in part within a vein 4202 in a patient's arm. A second guidewire 4206 may be inserted into device 100 through one-way valve 4116 so to position at least part of the second portion 4108 within vein 4202. A first guidewire 4204 may be inserted into device 100 through one-way valve 4114 so to position at least part of the first portion 4104 within artery 4200. Upon positioning device 100 or portions thereof as desired, first guidewire 4204 and second guidewire 4206 can be removed, and one-way valves 4114, 4116 prevent blood from leaking out of device 100. An optional dilator 3402, as referenced in detail herein, can be used to facilitate a transition between the first guidewire 4204 and/or the second guidewire 4206 and the artery 4200 and/or vein 4202 of interest, so that the artery 4200 and/or vein 4202 is gradually expanded to receive portions of device 100 after use of dilator 3402. For example, one or more dilators 3402 may be advanced over first guidewire 4204 and/or second guidewire 4206 into artery 4200 and/or vein 4202, noting that dilators 3402 would have a larger outer perimeter than the guidewires 4204, 4206, and then portions of device 100 could be positioned into artery 4200 and/or vein 4202 over dilator(s) 3402. When such a device 100 is properly positioned, blood can flow from artery 4200 into device 100 and into vein 4202. As shown in FIG. 28, device 100 does not need to enter an artery 4200 and an adjacent vein 4202 within the same plane, and that such an angle (at or near 90° relative to artery 4200 and vein 4202) may not be preferred due to potential fluid shear with said angles. FIGS. 27A and 27C show exemplary angle $A_1$ and an exemplary angle $A_2$, whereby $A_1$ and $A_2$, as shown therein, are each greater than 90°, and said angles are also greater than 90° as shown in FIG. 28. Should angles $A_1$ and/or $A_2$ approach 90° (implying a device bend approaching 90°), be 90° (implying a device bend of 90°), or be less than 90° (implying a device bend of greater than 90°), blood flow would become disturbed given the sharp turn which would result in energy losses, which is generally not preferred. A larger angle $A_1$ also allows first portion 4104 of device 100 to be positioned in artery 4200 relatively higher up, for example, than second portion 4108 positioned within vein 4202, in at least one exemplary use, such as shown in FIG. 28. General deformability/flexibility of at least part of device 100 would allow a user not only to more easily position the various areas of device 100 within a patient's vasculature, but also would allow for desired angles (such as angle $A_1$ and/or $A_2$) to be achieved upon device 100 implantation. For example, device 100 could have a general s-shape when being positioned or ultimately positioned within a patient, such as shown in FIGS. 27A and 28.

Figure 29:
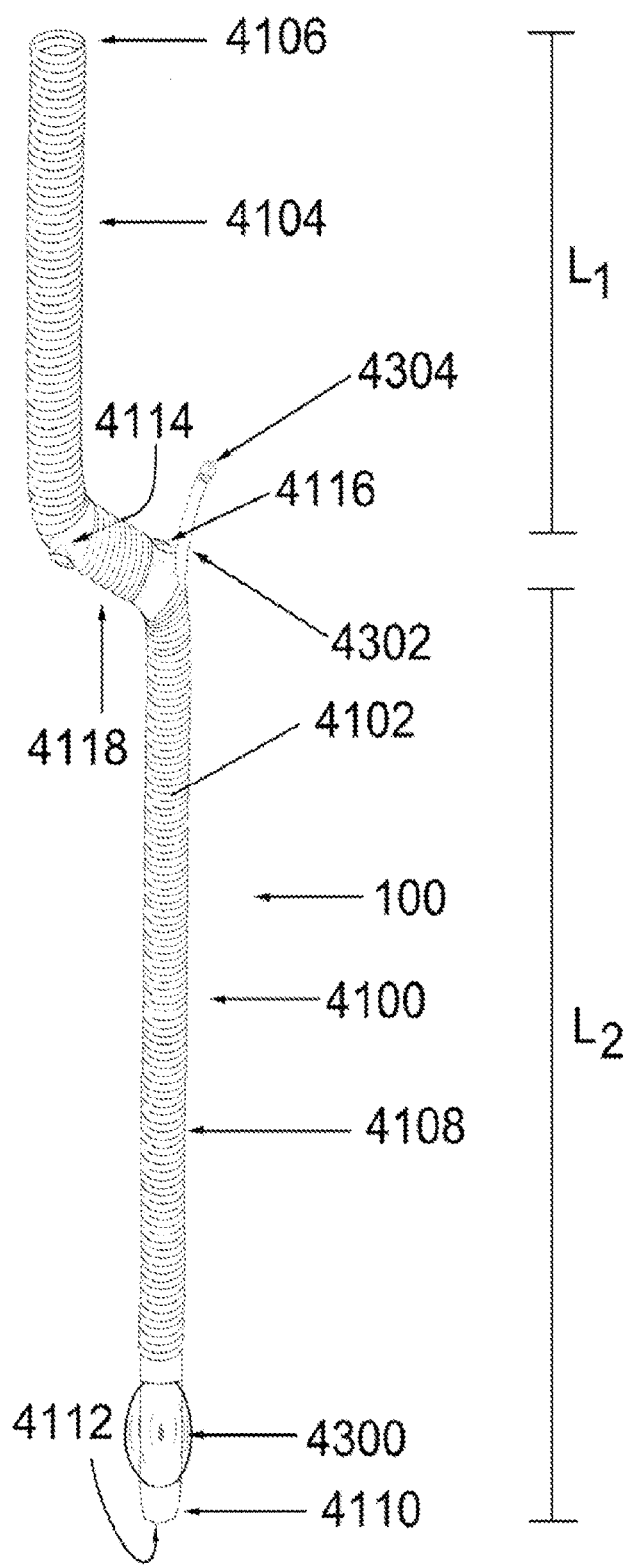
FIG. 29 shows a retroperfusion device, according to an exemplary embodiment of the present disclosure.
Figure 30:
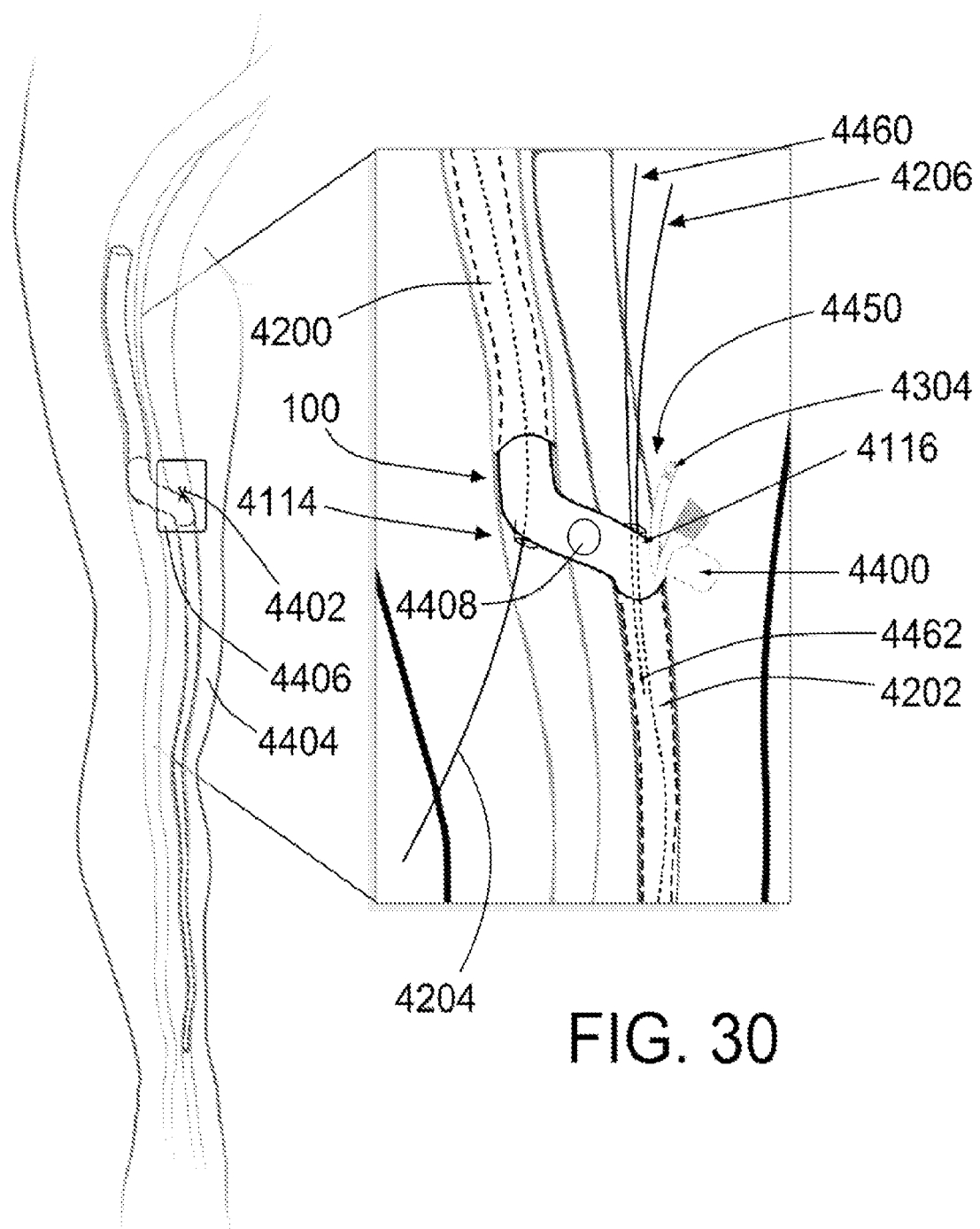
FIG. 30 shows a retroperfusion device positioned at least partially within a mammalian vasculature, according to an exemplary embodiment of the present disclosure.

FIG. 29 shows an additional embodiment of a device 100 of the present disclosure. As shown therein, device 100 comprises a balloon 4300 positioned within or coupled to second portion 4108 of device 100, with balloon 4300 in communication with a balloon inflation tube 4302 having a balloon port 4304. Introduction of a gas and/or a liquid into balloon port 4304 can be used to inflate balloon 4300, and removal of gas and/or a liquid via balloon port 4304 can be used to deflate balloon 4300. Balloon 4300, in at least one embodiment, is useful to hold/anchor a portion of device 100 in place within a patient's vasculature. Balloon 4300 may also, or alternatively, be used to ensure that blood flowing through device 100 flows in a retrograde direction, and that blood flowing therethrough flows at a desirable rate, which may be less than a full rate which would occur should no balloon 4300 be present. For example, inflation and/or deflation of balloon 4300 could be used to control blood flow through that portion of device 100, so that a desired flow rate, volume, and/or pressure of blood flows through device 100 to vein 4202, which can be determined using a pressure/ flow guidewire, for example. As such, devices 100 can effectively regulate blood pressures through device 100 and the amount (rate, volume, and/or pressure) of blood into vein 4202. In at least one embodiment, general dimensions (diameter(s) and/or length(s) of various regions of device 100) may be specified so that blood flow therethrough is at a desired rate, consistent with the general teachings of Pouiselle's law. Balloon 4300 can also be used to prevent the backflow of blood from vein 4202 into device 100. The entirety of device 100 does not need to be deformable, but in at least some embodiments, portions of first portion 4104 and/or second portion 4108 are deformable as referenced herein. FIG. 30 shows an embodiment of a device 100 of the present disclosure partially positioned within vein 4202, with such placement facilitated using a splittable introducer sheath 4400. Splittable introducer sheath 4400 can be positioned within an opening of vein 4202, and a portion of device 100 (such as second portion 4108) can be positioned inside of splittable introducer sheath, with such placement being facilitated using a second guide wire 4206, such as shown in FIG. 28. In at least one method (or step(s) of a method), splitttable introducer sheath 4400 can be positioned within an opening of an artery 4200 and/or a vein 4202 (noting that two splittable introducer sheaths can be used, one in artery 4200 and one in vein 4202, or only one splittable introducer sheath can be used in either artery 4200 or vein 4202), and using guidewire 4204 or 4206, a portion of device 100 can be advanced into artery 4200 and/or vein 4202. Guidewire 4206, for example, can be advance through various vein 4202 valves (such as in the middle/center of each valve), so that said valves remain functional after ultimate removal of guidewire 4206 (so not to destroy said valves). After placement of the portion of device 100 therein, splittable introducer sheath 4400 can be split so that it can be removed from vein 4202 while the portion of device 100 remains within vein. One or more optional sutures 4402, as shown in FIG. 30, can be used to secure device 100 to the patient's skin 4404, and/or one or more bandages 4406 can be used to cover the skin 4404 to potentially facilitate healing and/or maintain a relatively clean location. After a period of time, such as 4-6 weeks to allow vein 4202 to generally and locally arterialize due to the higher pressure of blood flowing therethrough from device 100, device 100 can be removed from the patient. Should it be desired to have device 100 positioned subcutaneously, instead of being exposed from the patient, an incision and/or other type of puncture can be made through skin 4404 to position the device subcutaneously. Procedurally, and in at least one method, second portion 4108 would be first positioned within vein 4202 prior to positioning first portion 4104 into artery 4200. In such a method, blood from artery 4200 would be routed through device 100 to vein 4202. However, should first portion 4104 be positioned into artery 4200 before second portion 4108 is positioned within vein 4202, blood from artery 4200 may exit device 100 outside of vein 4202, which would not be preferable.

In addition to the foregoing, at least one exemplary device 100 of the present disclosure may comprise a pressure controlling element 4408, such as shown in FIG. 30. Pressure controlling element 4408 would allow a user to control/regulate the general blood pressure through at least part of device 100, and may be positioned at various regions along device. Pressure controlling element 4408, in at least one embodiment, may be positioned at or near segment 4118, which, in various embodiments and/or uses, may be exposed outside of a patient when device 100 is implanted and in use. Pressure controlling element 4408, in at least one embodiment, is adjustable by a user of device 100 and/or a person positioning or otherwise maintaining device 100. For example, pressure controlling element 4408 may comprise an occluder (to partially occlude lumen 4112 at a location within device 100), a pressure/flow wire (operable to detect blood pressure within lumen 4112), or another device useful to obtain blood pressure/flow data and/or adjust a local dimension of device 100 as desired. There are several ways pressure can be controlled/regulated to avoid over-pressurization of veins, including the foregoing as well as, for example, use of an external constrictor (another exemplary pressure controlling element 4408), an internal stenosis that resorbs over time (poly(lactic-co-glycolic acid) (PLGA), another exemplary pressure controlling element 4408), and/or by design, to reduce the dimension of the arterial portion (first portion 4104) of device 100. As noted above, and based on Pouseulle's law, diameter and length can be selected of the arterial portion (first portion 4104) to obtain the desired pressure drop, which will, in at least one embodiment, involve a reduction of the diameter of (first portion 4104) of the catheter, which is desirable as it would imply a lower profile device 100 in the patient's arterial system. As shown in FIG. 30, an exemplary system 4450 of the present disclosure includes an exemplary device 100 of the present disclosure and at least one other item, such as, for example, one or more of a first guide wire 4204, a second guide wire 4206, a splittable introducer sheath 4400, and/or a data wire 4460.

Figure 31:
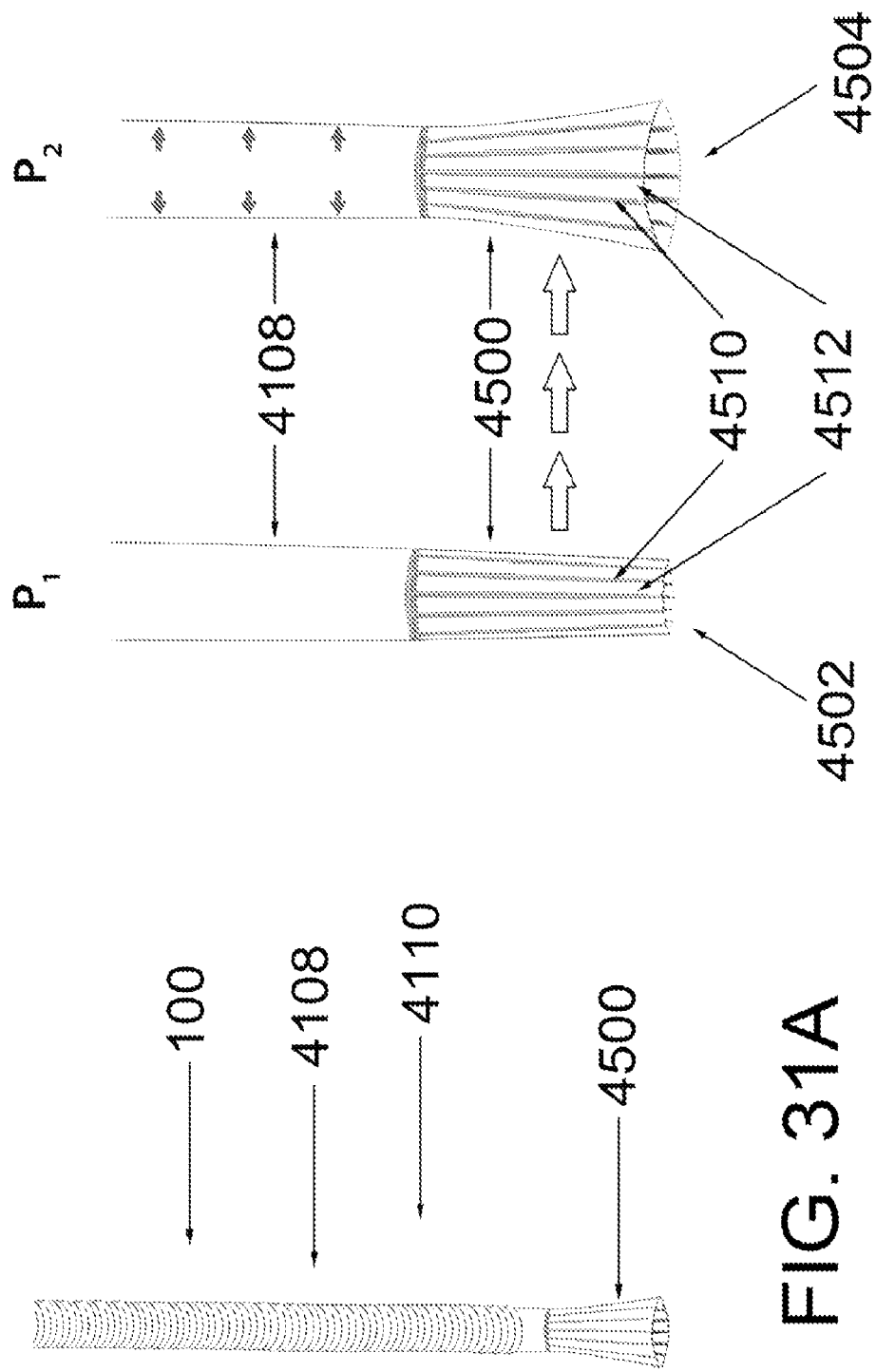
FIGS. 31A and 31B show a portion of a retroperfusion device having a flarable tip, according to an exemplary embodiment of the present disclosure.

An additional embodiment of a portion of an exemplary device 100 of the present disclosure is shown in FIGS. 31A and 31B. As shown in FIG. 31A, part of a second portion 4108 (of unitary body 4100) of an exemplary device 100 is shown therein, wherein distal end 4110 comprises, defines, and/or is coupled to a flarable tip 4500. Flarable tip 4500, as shown in FIG. 31A, can be coupled to second end 4110 of second portion 4108, or can be part of or defined at second end 4110. Flarable tip 4500, as shown in FIG. 31B and in various embodiments, is configured to shift from a first configuration 4502, which is generally tapered or unflared, to a second configuration 4504, which is generally flared, and back again. Phrased differently, flarable tip 4500, in various embodiments, is configured to shift from a first configuration 4502, which is not expanded, to a second configuration 4504, which is generally expanded, and back again. Said configurations, as referenced above, occur based upon pressures of fluid flowing therethrough when device 100 is positioned within a luminal organ having a fluid therein, as described in further detail below. For example, and as shown on the left side of FIG. 31B, if device 100 was positioned wholly within a vein 4202 and not susceptible to arterial blood pressures, flarable tip 4500 would be in a first configuration 4502 or relatively close to a first configuration 4502, as flarable tip 4500, configured consistent with the present disclosure, would not shift to a second configuration 4504 because venous blood pressure ($P_1$ in FIG. 31B) would not be high enough to cause flarable tip 4500 to shift to a second configuration 4504. However, for example and as shown on the right side of FIG. 31B, when device 100 is positioned within a vasculature as generally referenced herein (wherein a first portion 4104 of device 100 is positioned within an artery 4200 and a second portion 4108 of device 100 is positioned within a vein 4202), flarable tip 4500 would be in or shift to a second configuration 4504 or relatively close to a second configuration 4504, as flarable tip 4500, configured consistent with the present disclosure, would flare or generally expand due to higher arterial blood pressure ($P_2$ in FIG. 31B) as compared to the relatively lower venous blood pressure ($P_1$ in FIG. 31B). Flarable tip 4500, as referenced herein, is generally configured so that the second end 4110 of the second portion 4108 of device 100 distends to the size (luminal perimeter) of the portion of vein 4202 having second end 4110 positioned therein so that blood flow therethrough is retrograde. In such a configuration, flarable tip 4500 serves as a flow direction regulator. In at least one embodiment, and as shown in FIG. 31B, an exemplary flarable tip 4500 may comprise a membrane 4510 of one or more thin or relatively thin materials, such as polytetrafluoroethylene (PTFE), mammalian tissue, and/or one or more other biologically-compatible thin or relatively thin materials, reinforced by a number of struts 4512 (also referred to as structural fibers), which may comprise nitinol, stainless steel, and/or one or more other biologically-compatible rigid compositions, so that a general axial integrity of flarable tip 4500 exists whereby flarable tip 4500 does not crumple or fold over during insertion into vein 4202 when it is in its first configuration 4502. As noted above, second configuration 4504 of flarable tip 4500 can be induced by pressure, such as when device 100 is connected to arterial pressure as generally referenced herein, since membrane 4510 can be distended open. The converse occurs when the pressure is disconnected (the flarable tip 4500 collapses) for removal. Flarable tip 4500 deployment, as referenced herein, can also flare open (shift to second configuration 4504) based upon a memory aspect of one or more component materials, such as nitinol, whereby struts 4512 have a general memory that permits struts 4512 to flare open due to some sort of engagement or general touching of struts 4512 in one or more particular fashions.

Figure 32:
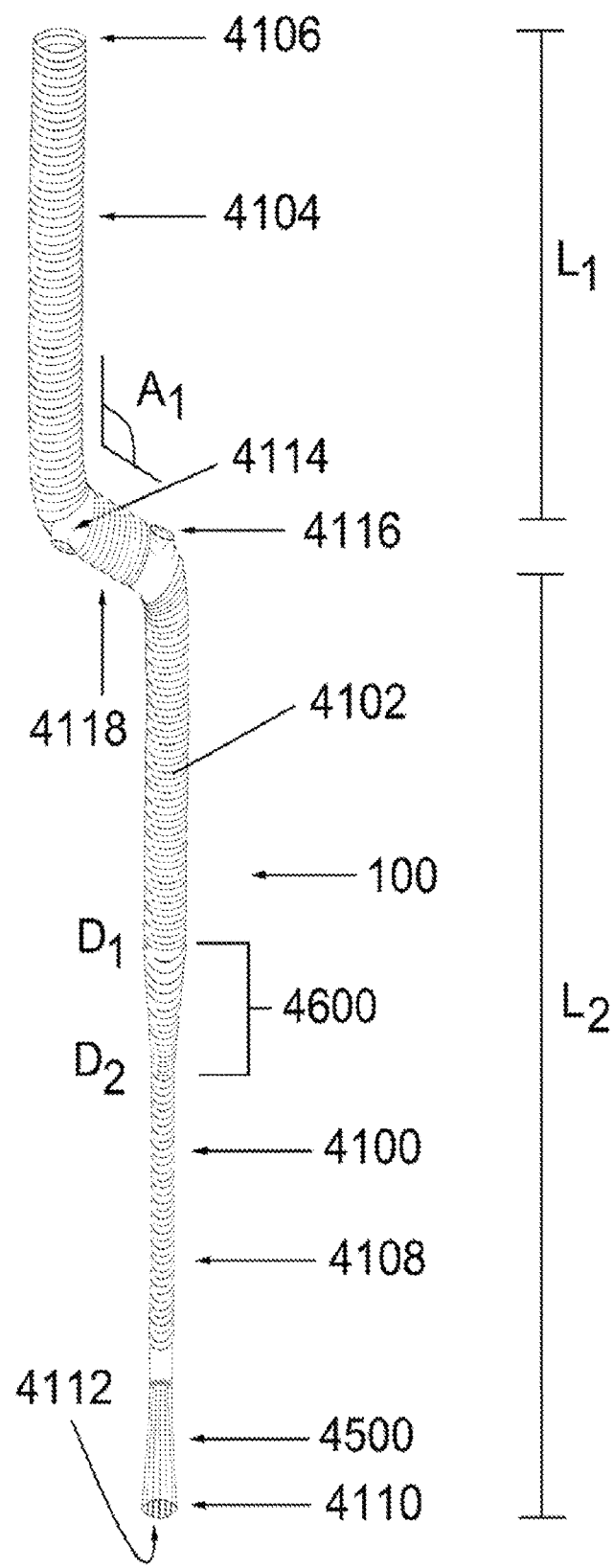
FIG. 32 shows a retroperfusion device with a tapered portion, according to an exemplary embodiment of the present disclosure.

An additional embodiment of a device 100 of the present disclosure is shown in FIG. 32. As shown in FIG. 32, device 100 comprises a number of components as shown in FIG. 27A as well as flarable tip 4500 as shown in FIGS. 31A and 31B. In addition, and in at least this embodiment, device 100 further comprises a tapered portion 4600, which comprises a portion of second portion 4108 (as shown in FIG. 32), or even all or substantially all of second portion 4108, extending from second one-way valve 4116 to flarable tip 4500, for example. As venous cross-sectional areas generally decrease toward the more peripheral areas of the body, such a device 100 embodiment may not only be easier to position within a patient, but also may provide more comfort to the patient upon implantation. In addition, a narrower or tapered second portion 4108 would reduce the risk of venous rupture during and after implantation, as such a device 100 would better conform to the patient's actual vein, such as a peripheral vein in a patient's leg. As shown in FIG. 32, tapered portion 4600 tapers distally from a first diameter (identified as D1 in the figure) to a second diameter (identified as D2 in the figure), whereby the first diameter is greater than the second diameter. Furthermore, one or more device embodiments of the present disclosure may have more than one tapered portion 4600 within second portion 4108 of device 100. The degree, number, and length of tapered portions 4600 can be selected to regulate the degree of pressure drop along the device 100 in order to reduce the transmission of arterial pressure to the venous system and to generally avoid overpressurization of the venous system. For example, if the arterial pressure into the first portion 4104 (the arterial portion of device 100) may be between 80 and 100 mmHg, it may be desirable to reduce this pressure, such as to between 40 and 60 mmHg, in the patient's venous system through a 40 mmHg (or other comparable) pressure drop along device 100. Such a determination of pressure drop can be implemented through a computational fluid dynamic simulation.

As referenced above, the present disclosure includes a novel approach for the reperfusion of a diseased peripheral artery, where an exemplary device 100 of the present disclosure can be used to connect a vein 4202 and an artery 4200 that run alongside one another. In this approach, the diseased vein 4202 is bypassed and 'retro-perfused' through the adjacent artery 4200 with arterial blood flow through a simple, flexible tube-type device 100. The diseased vein 4202 is not only provided with oxygen-rich blood immediately but, as referenced herein, may also be arterialized chronically (such as over a period of several weeks, for example). The pressure level and flow rate in the peripheral vein are usually much lower than in the artery 4200 at the corresponding level (e.g., femoral vein vs. femoral artery). As the vein 4202 is perfused by the blood flow from the artery 4200 through the device 100, the venous pressure may change depending on the relative flow conditions between the vein 4202 and the artery 4200. One factor, which may be a relatively important one, for the arterialization is how much the vein 4202 is pressurized by the arterial blood flow. Too much pressure would cause damage, while too little pressure would not have the desired effect. Hence, the right amount of pressure increased (such as approximately the average of arterial and venous pressure; i.e., ~40-60 mmHg as previously referenced herein) would be necessary. Device 100 embodiments of the present disclosure can regulate the pressure through the degree of articulation (bending) of said device 100. The pressure drop or energy loss in a circular pipe occurs to various degrees depending on the geometry of the device and the inlet and outlet boundary conditions. The geometric change is the primary determinant of pressure drop (e.g., sudden expansion or contraction of the lumen area). For an isodiametric circular tube, such as device 100 embodiments of the present disclosure, a simple but effective way of manipulating the pressure drop along the unitary body 4100 is to make a local curvature in the unitary body 4100 as referenced above and as shown in FIGS. 27A and 27C for example (with respect to the localized device 100 bending corresponding to angles $A_1$ and $A_2$).

Figure 33:
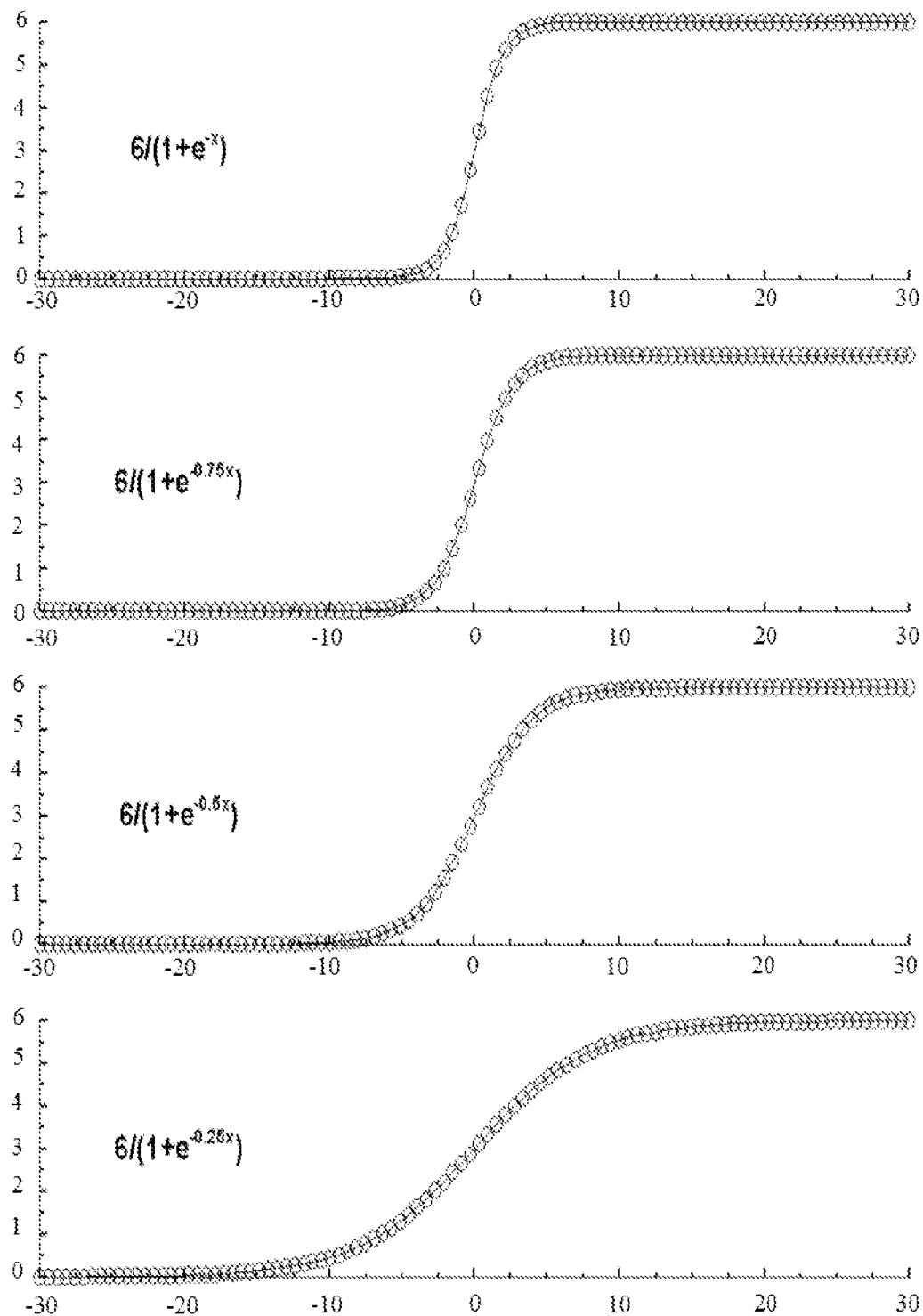
FIG. 33 shows several curvature profiles tied to mathematical functions, according to exemplary embodiments of the present disclosure.
Figure 34:
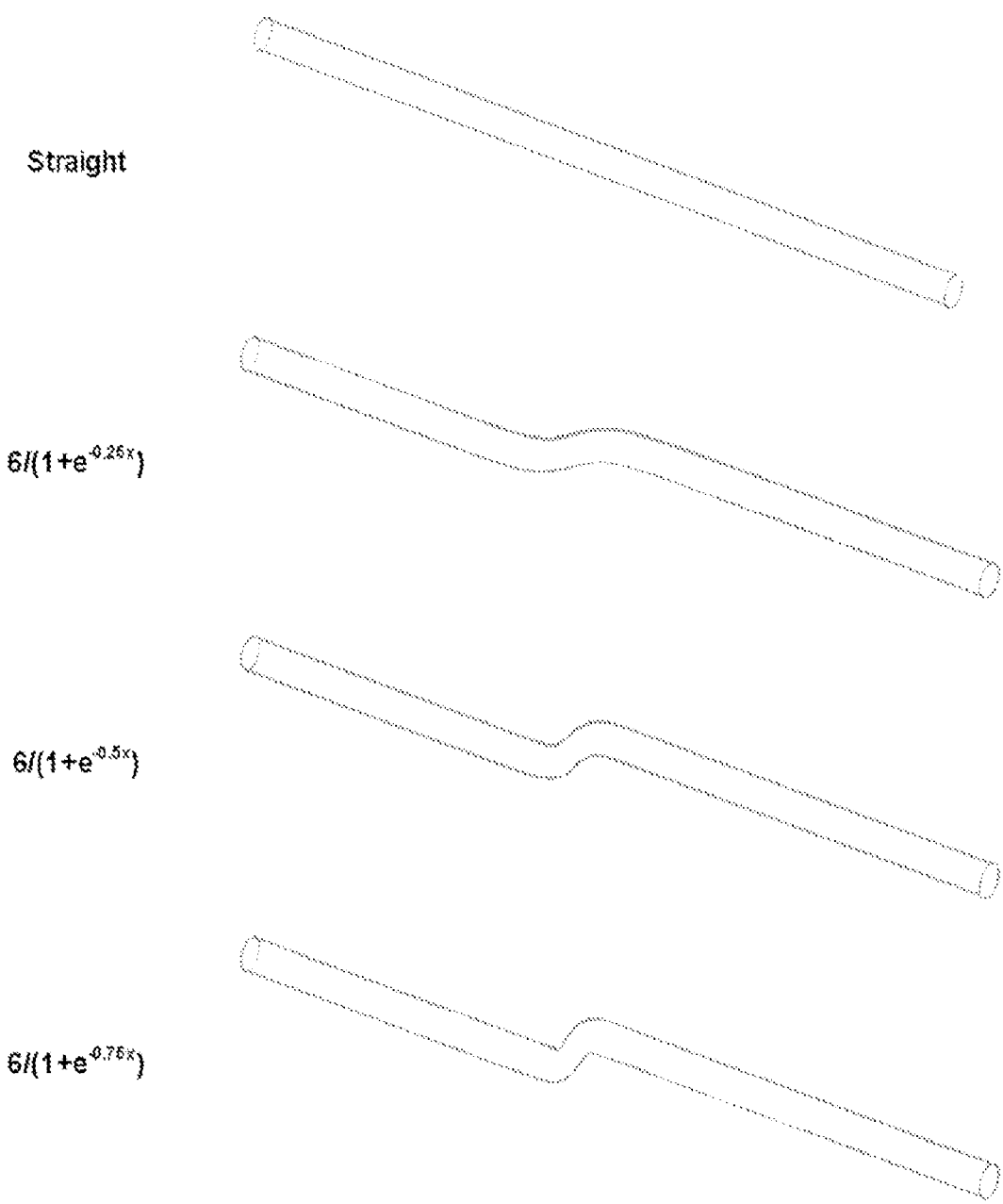
FIG. 34 shows various device configurations based upon sigmoidal functions, according to exemplary embodiments of the present disclosure.

The present disclosure also includes a determination of the relation between the degree of local bend in the device 100 and the pressure drop along the device 100 in connection with the local bend. To demonstrate the same, a sigmoidal function was adopted to model the local curvature of a circular tube since a wide range of profiles can be systematically generated by varying two arguments of the function according to the situations where the device is deployed. The adopted sigmoidal function has two primary arguments (A and B in Equation 1) that can be changed in the profile as follows:

$$f(x) = \frac{A}{(1 - e^{-Bx})} \quad [1]$$

where A and B are varied depending on the vein and artery size, the distance between two vessels alongside one another, and degree of local bending of the device. For the present testing, the diameter (D) and the distance between the inlet and outlet of the device (L) was assumed to be 4 and 60 mm, respectively, such as shown in the exemplary devices shown in FIG. 34. FIG. 33 shows that given the vein and artery dimension (i.e., A is determined by the vein and artery diameter and distance between two vessels alongside), a variety of local curvature profiles of the device are generated by changing the argument B. As the B value increases, the profile becomes steeper which may lead to the larger pressure drop across the device. FIG. 34 depicts the actual device configurations constructed from the sigmoidal function with various arguments (i.e., B varies from 0.25 to 0.75).

Figure 35:
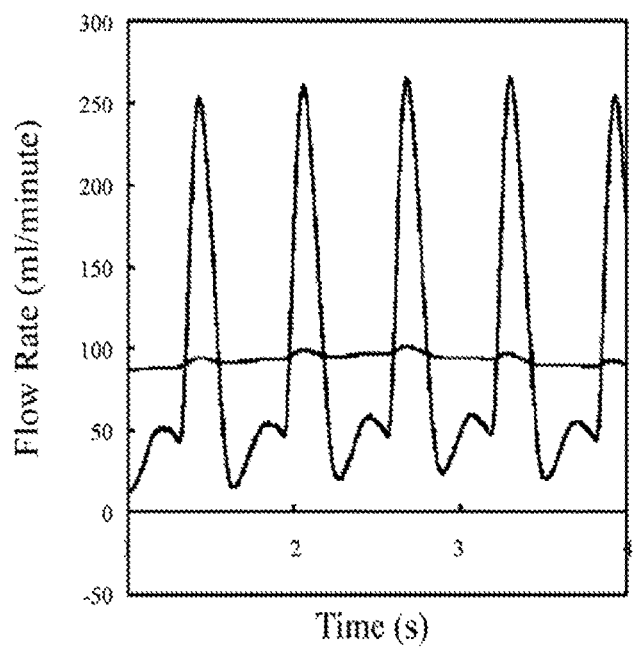
FIG. 35 shows in vivo wave forms obtained from a femoral artery.
Figure 36:
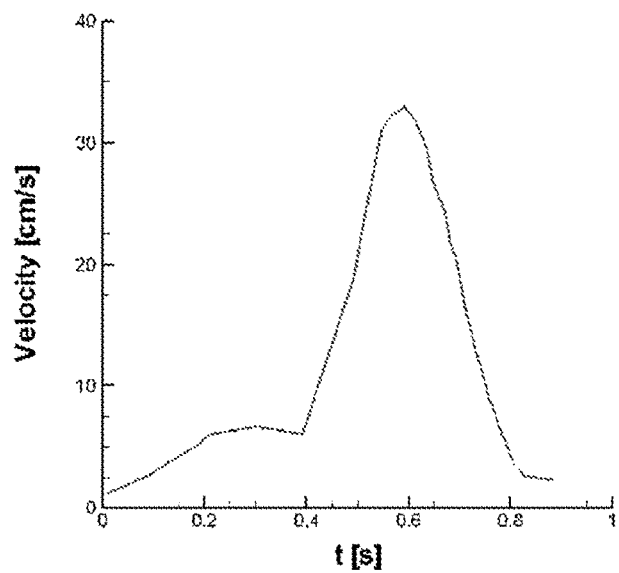
FIG. 36 shows a pulsatile inlet velocity profile, according to an exemplary embodiment of the present disclosure.

The ability of the device to adjust the pressure change along the device with various local geometric changes subject to in vivo flow conditions (such as shown in FIG. 35) was then determined. The temporal velocity profile at the device inlet (as shown in FIG. 36) was specified by digitizing in vivo flow wave form shown in FIG. 35 for flow modeling purposes. The flow field was then obtained by solving the Navier-Stoke Equation as follows:

Continuity:

$$\nabla \cdot \vec{V} = 0 \quad [2]$$

Momentum:

$$\rho \frac{\partial \vec{V}}{\partial t} + \rho (\vec{V} \cdot \nabla) \vec{V} = -\nabla p + \nabla \cdot \left( \mu \left( \nabla \vec{V} + (\nabla \vec{V})^T \right) \right) \quad [3]$$

where $\vec{V}$, p, μ, and r are pressure, dynamic viscosity of blood, and blood density, respectively. Blood was assumed as an incompressible and Newtonian viscous fluid with a constant density of 1060 kg/m³ and a constant dynamic viscosity of 0.0035 kg/m-s.

Regarding pressure regulation, the pressure drop across the device is a function of the device configuration modeled by the local curvature profile. In the laminar flow regime such as the present flow condition adopted (14≤Re≤400, $Re_{mean}$=147), the pressure drop along a straight circular tube with a specific length was established, for example:

$$\Delta p = f \cdot \frac{L}{D} \cdot \frac{\rho v^2}{2}, f = \frac{64}{Re}$$

where L, D, and f denote tube length, diameter, and flow friction factor, respectively. A pressure drop is also a general function of a relative flow condition between two vessels (such as artery 4200 and vein 4202), which are connected to one another using a device 100 as generally referenced herein. Such a flow condition could vary from patient to patient, and could also vary depending on the various positions device 100 would be positioned within artery 4200 and vein 4202. With respect to relative flow conditions, the medical personnel involved with selection and/or implantation of device 100 into a patient could, for example, refer to a table or other database of information that relate to various patient arterial blood pressures, a length of device 100 needed (such as L2, referenced herein) which would depend on the patient's height, and blood flow, which can be measured using one or more other devices, such as a data wire 4460 (which may include, but is not limited to, a pressure wire or catheter, a flow wire or catheter, or a combination pressure and flow wire or catheter, for example), having a sensor 4462 thereon or therein (such as a pressure sensor or flow sensor) so to identify flow and so that one or more devices angles and/or bends referenced herein can be adjusted to provide the desired pressure drop. Since the pressure drop varies with the curvature applied to a straight circular tube, the pressure drop of a curved circular tube was calculated relative to a straight pipe subject to an identical flow condition. This is an indicator of how much additional pressure drop is induced by the local geometric change of the device. Five different configurations of the curved tube were investigated (with results shown in Table 1), and the cycle-average relative pressure drop was calculated for each configuration.

TABLE 1

| | Cycle-average Relative Pressure Drop | | | | | |
|---|---|---|---|---|---|---|
| Config. | Straight | Case I $6/(1 + e^{-0.25x})$ | Case II $6/(1 + e^{-0.5x})$ | Case III $6/(1 + e^{-0.75x})$ | Case IV $6/(1 + e^{-x})$ | Case V 180° Bend |
| $\frac{\Delta p_{cu}}{\Delta p_{st}}$ | 1 | 1.09 | 1.19 | 1.28 | 1.37 | 2.34 |
| $\frac{(\Delta p_{cu}/L_{cu})}{(\Delta p_{st}/L_{st})}$ | 1 | 1.08 | 1.17 | 1.24 | 1.32 | 1.86 |
| Device bend (0° = straight) | 0 | 35 | 42.5 | 53.5 | 69.5 | 180 |

Figure 37:
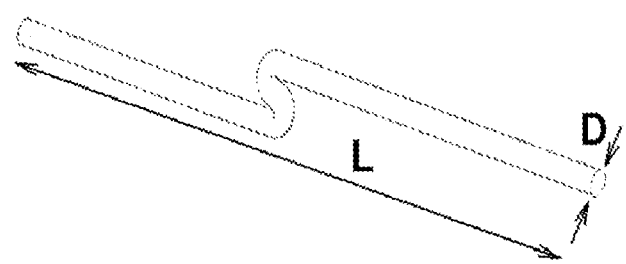
FIG. 37 shows a device having an extreme curvature (180° bend), according to an exemplary embodiment of the present disclosure.
Figure 38:
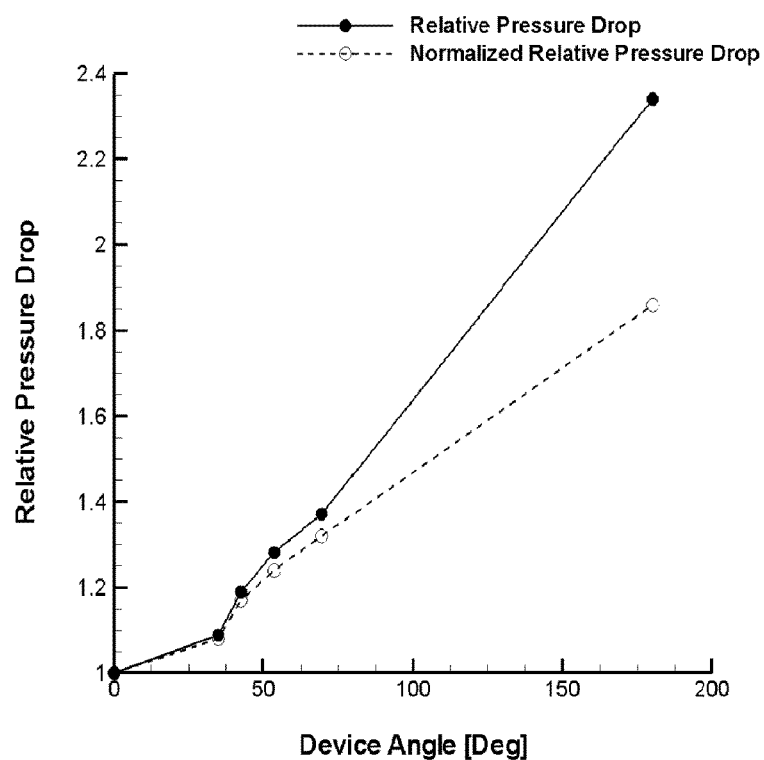
FIG. 38 shows a depiction of a relative pressure drop as compared to a relative pressure drop in view of device curvature angles, according to an exemplary embodiment of the present disclosure.
Figure 39:
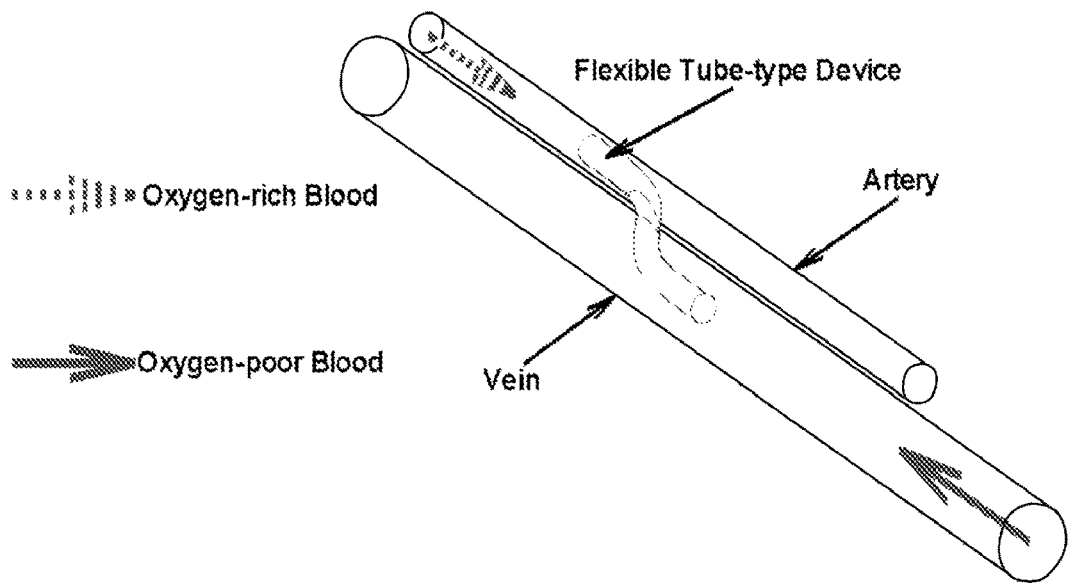
FIG. 39 shows a device positioned within a mammalian artery and vein, according to an exemplary embodiment of the present disclosure.

A circular tube with 180° bending (such as shown in FIG. 37) was examined as an extreme case. The results demonstrated that the relative pressure drop increases as the curvature becomes steeper (i.e., from Case I up to Case IV, as shown in Table 1 and depicted in FIG. 38). The increase in pressure drop shown in FIG. 38 relates the conditions shown in FIGS. 33-37, for example, and not under the circumstance depicted in FIG. 39. The angles referenced in FIG. 38 correspond to 180° minus $A_1$ or 180° minus $A_2$, as appropriate. Two different definitions of relative pressure drop were considered (i.e., $\Delta p_{cu}/\Delta p_{st}$ and $(\Delta p_{cu}/L_{cu})/(\Delta p_{st}/L_{st})$), demonstrating that they result in only slight difference for the sigmoidal function-based curved tubes (Case II-Case IV) while they can lead to a significant discrepancy for the extremely bent configuration (Case V). Although the distance between inlet and outlet of the device is identical for all the tube configurations considered (i.e., L remains same as 60 mm, as shown in FIG. 34), the length of flow path (i.e., $L_{cu}$) increases when the curvature is applied to a straight tube. Since the actual flow path length is a primary regulator of the pressure drop along the tube, the length needs to be taken into account to calculate the relative pressure drop. Thus, the normalized relative pressure drop or $(\Delta p_{cu}/L_{cu})/$ ($\Delta p_{st}/L_{st}$) seems to be a relevant indicator of the pressure drop in a circular tube with local curvature. As such, the results indicate that the approaches referenced herein are a useful and inventive tool to generate a wide range of variations in pressure drop across the device to pressurize the vein to different extents.

In summary, the devices and methods to regulate the degree of pressure drop through the change in catheter configuration (at the bend) at the junction between the arterial and venous portion of the device are disclosed herein. The pressure drop across the device can be regulated up to any number of percentages, such as 10%, 20%, 30%, 40%, or higher or lower, for practical changes in curvature or shape (as indicated below). These changes in curvature can be ensured, for example, through a suture anchor in the device and in the patient's tissue at the time of implant. In addition, and in various device 100 embodiments, the degree of pressure drop can be regulated based on one or more device diameters (such as $D_1$ and $D_2$ referenced herein and shown in FIG. 32), and on one or more device 100 lengths (such as $L_1$ and $L_2$ referenced herein and shown in FIG. 27A). For example, and in at least one embodiment, the degree of pressure drop through device 100 is based, in at least part, upon a device diameter, length, and device 100 bend/curvature. As noted above, and in at least the aforementioned embodiment or other embodiments, the degree of pressure drop through device 100 is based, in at least part, upon a device diameter, device length, and device 100, a flow friction factor, and a relative flow condition between two vessels (such as artery 4200 and vein 4202), which are connected to one another using a device 100 as generally referenced herein.

While various embodiments of retroperfusion devices and systems and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A perfusion device, comprising:
   a body having a wall and a lumen defined therethrough;
   a first portion terminating at a first end and configured for at least partial placement within a mammalian artery;
   a first one-way valve positioned at or near an end of the first portion opposite the first end and disposed in the wall and configured for placement within a mammalian artery;
   a second portion terminating at a second end and configured for at least partial placement within a mammalian vein; and
   a second one-way valve positioned at or near an end of the second portion opposite the second end.

2. The device of claim 1, wherein the first portion has a first length, wherein the second portion has a second length, and wherein the first length is less than the second length.

3. The device of claim 1, wherein in use at least part of the first portion is configured to be positioned within a subclavian artery or axillary artery, and wherein at least part of the second portion is configured to be positioned within a subclavian vein or an axillary vein for use and/or treatment at or near the heart.

4. The device of claim 1, wherein in use at least part of the first portion is configured to be positioned within an iliac artery, and wherein at least part of the second portion is configured to be positioned within a saphenous vein or a femoral vein.

5. The device of claim 1, wherein one or more portions of the body is/are flexible.

6. The device of claim 1, wherein the body is able to deform easily without collapsing so that the lumen remains open to allow blood to flow from the first end, through the body, and out of the second end when in use.

7. The device of claim 1, wherein the body comprises a coil-reinforced wall having one or more coils.

8. The device of claim 1, further comprising:
   a balloon positioned within or coupled to the second portion.

9. The device of claim 1, further comprising:
   a flarable tip defined at or coupled to the second end of the device.

10. The device of claim 9, wherein the second portion comprises one or more tapered portions.

11. The device of claim 1, wherein the second portion comprises a first tapered portion.

12. The device of claim 1, wherein the device is configured so that the second portion is sized and shaped to facilitate implantation within the mammalian vein.

13. The device of claim 1, wherein the device is configured so that the second portion is sized and shaped to reduce a risk of rupture of the mammalian vein.

14. The device of claim 1, wherein when the first portion is immediately adjacent to the second portion, the first portion meets the second portion at a central junction.

15. The device of claim 14, wherein part of the first portion adjacent to the central junction is flexible.

16. The device of claim 1, wherein when the device comprises a segment between the first one-way valve and the second one way-valve, the device is configured so that a first angle ranging from above 0° to 180° can be formed relative to the first portion and the segment and/or a second angle ranging from above 0° to 180° can be formed relative to the second portion and the segment.

17. The device of claim 1, forming part of a system, the system further comprising at least one other item selected from the group consisting of one or more of a first guide wire, a second guide wire, a splittable introducer sheath, and/or a data wire.

18. A method, comprising the step of positioning the device of claim 1 within a mammalian patient so that the first portion is positioned within an artery and so that the second portion is positioned within a vein.

19. The method of claim 18, wherein the positioning step is performed by positioning a first portion of a perfusion device within the artery, wherein a first guidewire is positioned through part of the first portion of the device into the artery, and positioning a second portion of a perfusion device within the vein, wherein a second guidewire is positioned through part of the second portion of the device into the vein.

20. The method of claim 19, wherein the positioning step is further performed by advancing a first dilator over the first guidewire before positioning the first portion of the perfusion device into the artery and by advancing a second dilator over the second guidewire before positioning the second portion of the perfusion device into the vein.

* * * * *